(12) United States Patent
Bannister et al.

(10) Patent No.: US 9,622,982 B2
(45) Date of Patent: Apr. 18, 2017

(54) CANCER DRUG AND USES

(71) Applicant: Health Clinics Limited, London (GB)

(72) Inventors: Robin M. Bannister, Essex (GB); John Brew, Hertfordshire (GB); Gregory A. Stoloff, London (GB)

(73) Assignee: HEALTH CLINICS LIMITED, London (GB)

( * ) Notice: Subject to any disclaimer, the term of this patent is extended or adjusted under 35 U.S.C. 154(b) by 99 days.

(21) Appl. No.: 14/155,320

(22) Filed: Jan. 14, 2014

(65) Prior Publication Data

US 2014/0199296 A1   Jul. 17, 2014

Related U.S. Application Data

(60) Provisional application No. 61/752,360, filed on Jan. 14, 2013, provisional application No. 61/782,585, filed on Mar. 14, 2013, provisional application No. 61/872,822, filed on Sep. 2, 2013.

(51) Int. Cl.

| | |
|---|---|
| *A61K 9/48* | (2006.01) |
| *A61K 31/05* | (2006.01) |
| *A61K 31/155* | (2006.01) |
| *A61K 31/19* | (2006.01) |
| *A61K 31/225* | (2006.01) |
| *A61K 31/353* | (2006.01) |
| *A61K 31/357* | (2006.01) |
| *A61K 31/366* | (2006.01) |
| *A61K 31/40* | (2006.01) |
| *A61K 31/4184* | (2006.01) |
| *A61K 31/517* | (2006.01) |
| *A61K 31/7068* | (2006.01) |
| *A61K 39/395* | (2006.01) |
| *A61K 31/352* | (2006.01) |
| *A23L 33/10* | (2016.01) |

(52) U.S. Cl.
CPC ............ *A61K 9/4858* (2013.01); *A23L 33/10* (2016.08); *A61K 31/05* (2013.01); *A61K 31/155* (2013.01); *A61K 31/19* (2013.01); *A61K 31/225* (2013.01); *A61K 31/352* (2013.01); *A61K 31/353* (2013.01); *A61K 31/357* (2013.01); *A61K 31/366* (2013.01); *A61K 31/40* (2013.01); *A61K 31/4184* (2013.01); *A61K 31/517* (2013.01); *A61K 31/7068* (2013.01); *A61K 39/39558* (2013.01)

(58) Field of Classification Search
None
See application file for complete search history.

(56) References Cited

U.S. PATENT DOCUMENTS

2005/0209292 A1* 9/2005 Chuang ............... A61K 31/225
514/369

FOREIGN PATENT DOCUMENTS

| CN | 1435167 A | 8/2003 |
|---|---|---|
| WO | 00027359 A1 | 5/2000 |

OTHER PUBLICATIONS

Mrowska et al (International Journal of Oncology, 2008, vol. 32, pp. 249-255).*
Yao et al (International Journal of Cancer, 2006, vol. 118, pp. 773-779).*
Babcook et al (Cancer Research, Apr. 15, 2013, vol. 73, No. 8, Suppl. 1, Abstract No. 3283).*
Tousoulis et al (International Journal of Cardiology, 2011, vol. 149, pp. 46-49).*
Lee, et al., "Outcomes with first-line platinum-based combination chemotherapy for malignant pleural mesothelioma: A review of practice in British Columbia,"(Jun. 2009), Lung Cancer, Elsevier, Amsterdam, NL, vol. 64, No. 3, pp. 308-311.
International Search Report PCT/EP2014/050635, mailed Jul. 17, 2014.

* cited by examiner

*Primary Examiner* — Karen Canella
(74) *Attorney, Agent, or Firm* — One3 IP Management, P.C.; Dean G. Stathakis; Peter D. Weinstein

(57) ABSTRACT

A pharmaceutical composition comprising a cancer therapeutic that is capable of inhibiting and/or reducing the ability of a cancer cell to take up and utilize glucose or other energy source, a lipid or other building block of a cell membrane or organelle, and/or cholesterol. The pharmaceutical composition can comprise one or more cancer therapeutics that can be administered individually or in combination to an individual.

23 Claims, 4 Drawing Sheets

CANCER DRUG AND USES

This application is a U.S. Non-Provisional application and claims priority pursuant to 35 U.S.C. 119(e) to U.S. Provisional Patent Application 61/752,360, filed Jan. 14, 2013, U.S. Provisional Patent Application 61/782,585, filed Mar. 14, 2013, and U.S. Provisional Patent Application 61/872,822, filed Sep. 2, 2013, each of which is hereby incorporated by reference in its entirety.

BACKGROUND

The majority of cancer treatments are selected to inhibit or reduce a cancer cells ability to survive and/or their ability to divide to form more cancer cells. While currently there are many cancer treatments that are prescribed to help an individual suffering from a cancer that have one or both of these abilities, it is worth noting that these same cancer treatments have several shortcomings. Among these are that an individual administered the treatment can suffer from a serious side effect. In addition, many treatments are cancer specific and only work on one type of cancer. Finally, their use is generally very costly and beyond the reach of a large number of individuals suffering from a cancer. What is needed is a treatment that has the ability to inhibit or reduce a cancer cells ability to survive and/or divide while at the same time the treatment: (1) is tolerated by an individual; (2) works against many different cancers; and, (3) is affordable so that all individuals suffering from a cancer can be administered the treatment.

Currently, there are whole classes of therapeutics that are administered to individuals who suffer from a genetic, metabolic or other disease or from a disease caused by a bacteria, virus or parasite (a "disease treating therapeutic") that treat the disease by inhibiting or reducing the ability of a cell to survive and/or divide. In particular, these disease therapeutics act by: (1) inhibiting or reducing the amount of lipids, other fats and/or cholesterol taken up by cells; and/or (2) inhibiting or reducing the ability of a cell to take up or utilize glucose or another energy source. While these disease treating therapeutics act in a manner that can treat a cancer, currently they are not prescribed to patients suffering from cancer.

Thus, it would be advantageous to use a disease treating therapeutic to treat cancer (hereinafter a "cancer therapeutic"). Such a cancer therapeutic can be administered to an individual either solely or in combination with one or more of additional cancer therapeutics to treat a cancer. Moreover, as these cancer therapeutics affect a cancer cells metabolism and ability to divide, they can be used against multiple different cancer types, and in some instances, all cancers.

Most cancer therapeutics are provided to a patient suffering from a cancer using a formulation that enables the therapeutic to dissolve in an aqueous solution that will mix with the patients plasma following transfusion. These formulations are more concerned with solubility and are not generally designed to enhance the effectiveness of the cancer therapeutic. One means of increasing the effectiveness of therapeutics that has been successful in the past is the use of lipid formulations. Lipid formulations have been shown to increase the effectiveness of certain classes of drugs, such as NSAIDs, while reducing some of their adverse side effects.

Among the classes of cancer therapeutics that would benefit from a lipid formulation are Artemisinin and its derivatives. Artemisinin is purified from the leaves of *Artemisia annua* (annual wormwood). The drug is named Qinghaosu in Chinese. *Artemisia annua* is a common herb and has been found in many parts of the world. Artemisinin, and its derivatives are a group of drugs that are known to have a rapid action in patients for the treatment of *Plasmodium falciparum* malaria. Treatments containing an artemisinin derivative (artemisinin-combination therapies, ACTs) are now standard treatment worldwide for *P. falciparum* malaria.

Use of the drug by itself as a monotherapy is explicitly discouraged by the World Health Organization, as there have been signs that malarial parasites are developing resistance to the drug. Therapies that combine artemisinin with some other antimalarial drug are the preferred treatment for malaria and are both effective and well tolerated in patients. The drug is also increasingly being used in *Plasmodium vivax* malaria, as well as being a topic of research in cancer treatment (http://en.wikipedia.org).

Because artemisinin itself has physical properties such as poor bioavailability that limit its effectiveness, semisynthetic derivatives of artemisinin have been developed. These include: Artesunate, Artemether, Dihydroartemisinin, Artelinic acid, Artenimol and Artemotil. There are also simplified analogs in preclinical research, including, arterolane.

Artemisinin and its derivatives have been shown in some studies to have some anticancer and antitumor activity. For instance, Arthemether has shown a strong inhibitory effects on brain glioma growth and angiogenesis in rats. It has also shown a dose- and time-dependent cytotoxicity that induced apoptosis and G2 cell cycle arrest in ovarian cancer cell lines, human leukemia HL60 cells, and human pancreatic cancer BxPC-3 and AsPC-1 cells. Dihydroartemisinin and other artemisinin-based endoperoxide compounds have been found to target human metastatic melanoma cells with induction of NOXA-dependent mitochondrial apoptosis that occurs downstream of iron-dependent generation of cytotoxic oxidative stress.

Other cancer therapeutics include drugs used as part of a chemotherapy regimen, including, alkylating agents, antimetabolites, anthracyclines, plant alkaloids, topoisomerase inhibitors, and other antitumour agents. Other cancer therapeutics include monoclonal antibodies and the new tyrosine kinase inhibitors, which directly target a molecular abnormality in certain types of cancer. Each of these other cancer therapeutics could benefit from a formulation that results in a maintenance or reduction of the number of cancer cells a patient has or the size of one or more tumors present in a patient.

While these cancer therapeutics function for their intended purpose, their effectiveness can be improved through a formulation that enhances their ability to act on their target cells. One means of doing this is to formulate cancer therapeutics in a lipid formulation.

SUMMARY

In an aspect of the present invention, a pharmaceutical composition comprising a therapeutic is used to treat a cancer (a "cancer therapeutic"). In an embodiment, a cancer therapeutic or derivative thereof, affects cellular metabolism. In an embodiment, a cancer therapeutic reduces the amount of circulating glucose in an individual. In another embodiment, a cancer therapeutic reduces the amount of circulating lipids, other fats and/or cholesterol.

In an embodiment, a cancer therapeutic can enter a macrophage resulting in the macrophage increasing the level of CD36 and LDL receptors, resulting in a reduction in circulating LDLs. In another embodiment, a cancer therapeutic increases the Glut-4 receptor on muscle cells, which results in a reduction in circulating glucose. In a further embodiment, a cancer therapeutic is one that removes and accepts electrons from molecules that results in the interference of the glycolytic process in a cell.

In an embodiment, a cancer therapeutic results in a cancer cell not being able to uptake sufficient quantities of glucose or another energy source resulting in the cell entering apoptosis and eventually dying. In a further embodiment, a cancer therapeutic results in a cell not being able to uptake sufficient quantities of a lipid, other fat and/or cholesterol, preventing the cancer cell from dividing and forming a progeny cancer cell.

In an aspect, the present invention is a pharmaceutical composition comprising a cancer therapeutic and a pharmaceutically acceptable lipid formulation. In a further aspect, the present invention is a cancer therapeutic is Artemisnin or a derivative thereof, including, without limitation, Artesunate, Artemether, Dihydroartemisinin, Artelinic acid, Artenimol and/or Artemotil. In an aspect the present invention includes a pharmaceutically acceptable solvent, a pharmaceutically acceptable stabilizing agent, pharmaceutically acceptable carrier and/or a pharmaceutically acceptable component.

In an aspect of the present invention, the cancer therapeutic is an alkylating agent, including, without limitation Cisplatin, carboplatin, mechlorethamine, cyclophosphamide, chlorambucil, ifosfamide and/or oxaliplatin. In a further aspect of the present invention, the cancer therapeutic is an anti-metabolite, including, without limitation, azathioprine and/or mercaptopurine and wherein, without limitation, the anti-metabolite is a synthetic, semisynthetic or derivative of an anti-metabolite. In an aspect of the present invention, the cancer therapeutic is a terpenoid, including, without limitation, a vinca alkaloid and/or a taxane, and further wherein, without limitation, the vinca alkaloid is Vincristine, Vinblastine, Vinorelbine and/or Vindesine and further, without limitation, the taxane is Taxol, Paclitaxel and/or Docetaxel and further wherein, without limitation, the taxane is a synthetic, semisynthetic or derivative of a taxane. In an aspect, the present invention the cancer therapeutic is a topoisomerase, and further wherein, without limitation, the topoisomerase is a type I topoisomerase and/or a type 2 topoisomerase. In an aspect, the present invention, the type 1 topoisomerase is camptothecins, and further wherein, the camptothecins is irinotecan and/or topotecan. In an aspect, the type II topoisomerase is amsacrine, etoposide, etoposide phosphate and/or teniposide, and further, wherein, without limitation, the topoisomerase is a synthetic, semisynthetic and/or derivative. In a further aspect of the present invention, the derivative is epipodophyllotoxins. In an aspect of the present invention, the cancer therapeutic is a cytotoxic antibiotic, and further wherein, without limitation, the cytotoxic antibiotic is actinomycin, anthracyclines, doxorubicin, daunorubicin, valrubicin, idarubicin, epirubicin, bleomycin, plicamycin and/or mitomycin. In an aspect of the present invention, the cancer therapeutic is a hormone, and further wherein, without limitation, the hormone is a lutenizing hormone releasing hormone agonist and further wherein, without limitation, the hormone is leuprolidine, goserelin, triptorelin, histrelin, bicalutamide, flutamide and/or nilutamide. In an aspect of the present invention, the cancer therapeutic is an antibody, and further wherein, without limitation, the antibody is Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab. In an aspect of the present invention, the artemesinin derivative is a butyrate ester of dihydroartemesinin.

In an aspect of the present invention, the cancer therapeutic is capable of reducing the number of cancer cells or tumor size in an individual suffering from a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, a therapeutic compound capable of reducing the number of cancer cells or tumor size in an individual suffering from a cancer by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

DESCRIPTION

Figure 1:
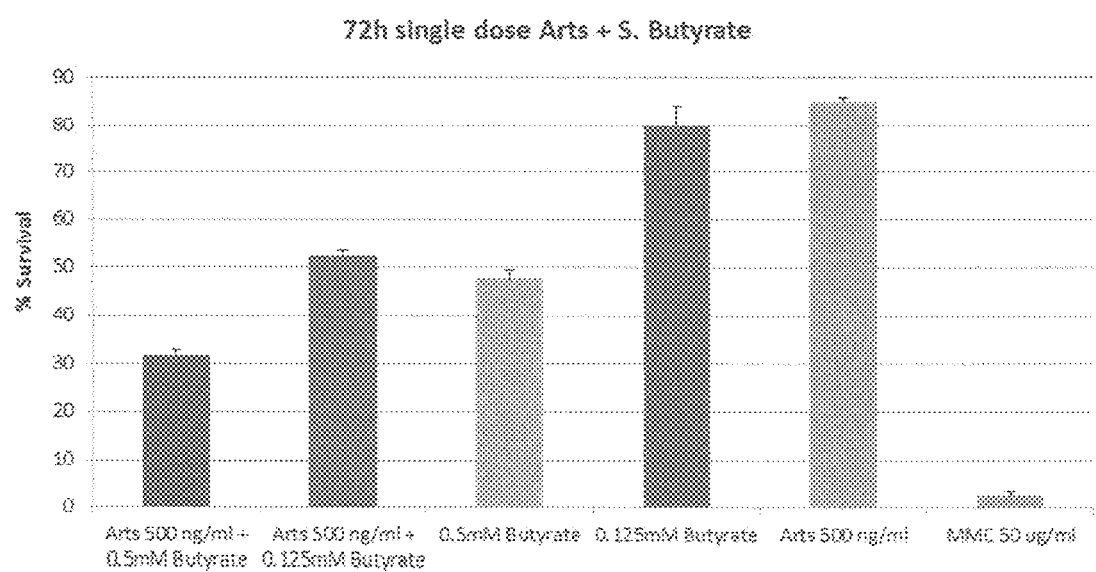
FIG. 1 shows the results for samples assessed 72 hours after wells containing MCF-7 cells (or no cells in a control) were administered a single dose of Artesunate and/or Sodium Butyrate.

Aspects of the present specification disclose, in part, a therapeutic compound. A therapeutic compound, includes, but is not limited to, a cancer therapeutic. A therapeutic compound is a compound that provides pharmacological activity or other direct effect in the diagnosis, cure, mitigation, treatment, or prevention of cancer, or to affect the structure or any function of the body of man or animals. A therapeutic compound disclosed herein may be used in the form of a pharmaceutically acceptable salt, solvate, or solvate of a salt, e.g. the hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. A therapeutic compound disclosed herein may have anti-cancer activity.

In an embodiment, a cancer therapeutic is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semisynthetic or derivative.

In an embodiment, a cancer therapeutic is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an anti-metabolite is a synthetic, semisynthetic or derivative.

In an embodiment, a cancer therapeutic is a plant alkaloid and/or terpenoid. These alkaloids are derived from plants and block cell division by, in general, preventing microtubule function. In an embodiment, a plant alkaloid and/or terpenoid is a vinca alkaloid, a podophyllotoxin and/or a taxane. Vinca alkaloids, in general, bind to specific sites on tubulin, inhibiting the assembly of tubulin into microtubules, generally during the M phase of the cell cycle. In an embodiment, a vinca alkaloid is derived, without limitation, from the Madagascar periwinkle, *Catharanthus roseus* (formerly known as *Vinca rosea*). In an embodiment, a vinca alkaloid includes, without limitation, Vincristine, Vinblastine, Vinorelbine and/or Vindesine. In an embodiment, a taxane includes, but is not limited, to Taxol, Paclitaxel and/or Docetaxel. In a further embodiment a plant alkaloid or terpernoid is a synthetic, semisynthetic or derivative. In a further embodiment, a podophyllotoxin is, without limitation, an etoposide and/or teniposide. In an embodiment, a taxane is, without limitation, docetaxel and/or ortataxel.

In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In an embodiment, a cancer therapeutic is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In an embodiment, a cancer therapeutic is an isoflavone. In a further embodiment, a isoflavone includes, but is not limited to, Daidzein and Genistein. In a further embodiment a isoflavone is a synthetic, semisynthetic or derivative.

In an embodiment, a cancer therapeutic is an isoflavandiol. In a further embodiment, an isoflavandiol includes, but is not limited to, Equol. In an embodiment, Equol is one of two enantiomeric forms, either (S)-Equol and (R)-Equol. In a further embodiment a isoflavandiol is a synthetic, semisynthetic or derivative.

In an embodiment, a cancer therapeutic is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an antracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In an embodiment, a cancer therapeutic is a hormone. In an embodiment a hormone includes, but is not limited to, lutenizing hormone releasing hormone agonists. In an embodiment, a hormone includes, without limitation, leuprolidine, goserelin, triptorelin, histrelin, bicalutamide, flutamide and nilutamide.

In an embodiment, a cancer therapeutic is an antibody. In an embodiment, an anticancer antibody includes, but is not limited to, Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab, Trastuzumab and/or any other known or developed antibody that functions as a cancer therapeutic.

In an embodiment, a cancer therapeutic is, without limitation, a statin. In a further embodiment, without limitation, a statin is, without limitation, atorvastatin, fluvastin, lovastatin, pitavastatin, pravastatin, rosuvastatin and/or simvastatin.

In an embodiment, a cancer therapeutic is, without limitation, a therapeutic for the treatment of diabetes. In an embodiment, a therapeutic for the treatment of diabetes is, without limitation, a biguanide, a thiazolidinedione, a secretagogue, an alpha-glucosidase inhibitor and/or a peptide analog. In an embodiment, a biguanide is, without limitation, metformin, phenformin and/or buformin. In another embodiment, a thiazolidinedione is, without limitation, rosiglitazone, pioglitazone and/or troglitazone. In an embodiment, a secretagogue is, without limitation, a sulfonylurea, a nonsulfonylurea and/or a meglitinide. In a further embodiment, a sulfonylurea is, without limitation, tolbutamide, acetohexamide, tolazamide, chlorpropamide, glipzide, glyburide, glimepiride, gliclazide, glycopyramide and/or gliquidone. In an embodiment, a meglitinide is, without limitation, repaglinide and/or nateglinide. In an embodiment, an alpha-glucosidase inhibitor is, without limitation, miglitol, acarbose and/or voglibose. In an embodiment, a peptide analog is, without limitation, an injectable incretin mimetic, an injectable glucagon-like peptide analog and/or agonist, a gastric inhibitory peptide analog, a dipeptidyl peptidase-4 inhibitor and/or an injectable Amylin analogue. In a further embodiment, an injectable glucagon-like peptide analog and/or agonist is, without limitation, exenatide, liraglutide and/or taspoglutide. In a further embodiment, a dipeptidyl peptidase-4 inhibitor is, without limitation, vildagliptin, sitagliptin, saxagliptin, linagliptin, allogliptin and/or septagliptin. In another embodiment, an injectable Amylin analogue is, without limitation, pramlintide. In an embodiment, a therapeutic for the treatment of diabetes is cinnamon and/or thiamine.

In an embodiment, a cancer therapeutic is, without limitation, a Peroxisome proliferator-activated receptor gamma (PPAR-y or PPARG) agonist. In a further embodiment, a PPAR-y is, without limitation, rosiglitazone, troglitazone, pioglitazone, netoglitazone, rivoglitazone and/or ciglitazone.

In an embodiment, a cancer therapeutic is a PPAR-13 agonist. In another embodiment, a PPAR-13 agonist is, without limitation, endurobol and/or GW0742.

In an embodiment, a cancer therapeutic is a PPAR-a agonist.

In an embodiment, a cancer therapeutic is, without limitation an antibiotic. In another embodiment, an antibiotic is, without limitation, isoniazid, rifampicin, pyrazinamide and/or ethambutol.

In an embodiment, a cancer therapeutic is, without limitation, an antihelminthic. In a further embodiment, an antihelminthic is, without limitation, abamectin, an aminoacetonitriles, a benzimadazole, diethylcaramazine, ivermectin, levamisole, niclosamide, an octadepsipeptides, phosphoric acid (metrifonate), praziquantel, a spiroindoles, suramin and/or pyrantel pamoate. In a further embodiment, an aminoacetonitrile is, without limitation, monepantel. In another embodiment, a benzimidazole is, without limitation, albendazole, fenbendazole, a flubendazole, thiabendazole and triclabendazole. In an embodiment, a flubendazole is, without limitation, mebendazole. In another embodiment, an octadepsipeptide is, without limitation, emodepside. In a further embodiment, a spiroindole is, without limitation, dequantel.

In an embodiment, a cancer therapeutic is, without limitation, a food additive and/or a vitamin. In a further embodiment, a food additive and/or vitamin is, without limitation, tributerin, vitamin C, vitamin 812, vitamin D, resveratrol and/or coenzyme Q12.

In an embodiment, a cancer therapeutic is, without limitation, a glucose intake inhibitor. In another embodiment, a glucose intake inhibitor is, without limitation, a GLUT-1 receptor inhibitor.

In an embodiment a cancer therapeutic is, without limitation, a lipid intake inhibitor. In a further embodiment, a lipid intake inhibitor is, without limitation, an LDL receptor inhibitor, an SR-81 inhibitor, an SR-82 inhibitor and/or a SR-83/CD36 (thrombospondin) receptor inhibitor.

In an embodiment, a cancer therapeutic is a glycolysis inhibitor. In another embodiment, a glycolysis inhibitor is, without limitation, a hexokinase inhibitor, a phosphoglucose isomerase inhibitor, a fructosebisphosphate inhibitor, a triosephosphate isomerase inhibitor, a glyceraldehyde phosphate dehydrogenase inhibitor, a phosphoglycerate kinase inhibitor, a phosphoglycerate mutase inhibitor, an enolase inhibitor and/or a pyruvate kinase inhibitor.

In an embodiment, a cancer therapeutic is, without limitation, an anti-malarial therapeutic. In a further embodiment, an anti-malarial therapeutic is, without limitation, amodiaquine, an artemisinin, atovaquone, chloroquine, clindamycin, doxycycline, halofantrine, mefloquine, primaquine, proguanil, pyrimethamine, a quinine and related agent, rufigallol, and/or a sulphonamide. In another embodiment, an artemisinin is, without limitation, arteether, artemether, artemisinin, artesunate and/or dihydroartemisinin. In another embodiment, a quinine and related agent is, without limitation, quinimax and/or quinidine. In another embodiment, a sulfonamide is, without limitation, sulfadoxine and/or sulfamethoxypyridazine.

In an embodiment, a cancer therapeutic is Artemisinin. In a further embodiment, a cancer therapeutic is a derivative of Artemesinin. Derivatives of Artemesinin include, but are not limited to, Artesunate, Artemether, Dihydroartemisinin, Artelinic acid, arterolane, Artenimol and Artemotil.

In An embodiment, Artesunate is prepared from dihydroartemisinin (DHA) by reacting it with succinic acid anhydride in basic medium. Pyridine as base/solvent, sodium bicarbonate in chloroform and catalyst DMAP (N,N-dimethylaminopyridine) and triethylamine in 1,2-dichloroethane have been used, with yields of up to 100%. A large scale process involves treatment of DHA in dichloromethane with a mixture of pyridine, a catalytic amount of DMAP and succinic anhydride. The dichloromethane mixture is stirred for 6-9 h to get artesunate in quantitative yield. The product is further re-crystallized from dichloromethane. a-Artesunate is exclusively formed (m.p 135-137° C.).

In an embodiment, Artemether is a methyl ether derivative of artemisinin, which is a peroxide lactone isolated from the Chinese antimalarial plant, *Artemisia annua*. It is also known as dihydroartemisinin methyl ether, but its correct chemical nomenclature is (+)-(3-alpha,5a-beta,6-beta,8a-beta, 9-alpha,12-beta,12aR)-decahydro-10-methoxy-3,6,9-trimethyl-3,12-epoxy-12H-pyrano(4,3-j)-1,2-benzodioxepin. It is a relatively lipophilic and unstable drug.

In an embodiment, Dihydroartemisinin is the active metabolite of all artemisinin compounds (artemisinin, artesunate, artemether, etc.) and is also available as a drug in itself. It is a semi-synthetic derivative of artemisinin and is widely used as an intermediate in the preparation of other artemisinin-derived antimalarial drugs. Dihydroartemisinin is the active metabolite of all artemisinin compounds (artemisinin, artesunate, artemether, etc.) and is also available as a drug in itself. It is a semi-synthetic derivative of artemisinin and is widely used as an intermediate in the preparation of other artemisinin-derived antimalarial drugs.

In an embodiment, Artelinic acid (or its salt, artelinate) is a semi-synthetic derivative of the natural compound artemisinin. Artelinic acid has a lower rate of neurotoxicity than the related artemisin derivatives arteether and artemether.

In an embodiment, Artemotil (INN; also known as β-arteether), is a semi-synthetic derivative of artemisinin, a natural product of the Chinese plant *Artemisia annua*.

In an embodiment, a cancer therapeutic is a butyrate ester of dihydroartemesinin with a structure that can include, but is not limited to the following:

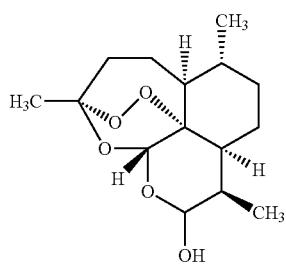

In an embodiment, a cancer therapeutic is a dichloroacetate ester.

In an embodiment, a patient is administered one or more of an alkylating agent, an anti-metabolite, a plant alkaloid, a terpenoid, a topoisomerase inhibitor, a cytotoxic antibiotics, a statin, an anti-diabetic drug, a PPAR-y, a PPAR-13, a PPAR-a, an antibiotic, an antihelminthic, an anti-malaria drug, a vitamin and/or a food additive. In an embodiment, a patient is administered one or more cancer therapeutics. In an embodiment, a patient is administered one, two, three, four, five, six, seven eight, nine, ten, eleven, twelve, thirteen, fourteen, fifteen, sixteen, seventeen, eighteen, nineteen or twenty different cancer therapeutics.

In an embodiment, a cancer therapeutic and its derivatives have half-lives of the order of 1 hour, and therefore require at least daily dosing over several days. In a further embodiment, a cancer therapeutic, includes, but not limited to, artemisinin and its derivatives have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

In an embodiment, the period of administration of a cancer therapeutic is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In an embodiment, a first therapeutic compound is administered to an individual and at a later date, a second therapeutic compound is administered to the same individual. In aspects of this embodiment, the first therapeutic compound is artemesinin or a derivative thereof and the second therapeutic compound is a different derivative of artemesinin. In an embodiment, the first therapeutic compound is artemesinin or a derivative thereof and the second therapeutic compound is a cancer therapeutic that is not artemesinin or a derivative thereof.

In an embodiment, a first therapeutic compound is administered to an individual at the same time as a second therapeutic compound is administered to the individual. In aspects of this embodiment, the first therapeutic compound is a artemesinin or derivative thereof and the second therapeutic compound is a different derivative of artemesinin. In an embodiment, the first therapeutic compound is artemesinin or a derivative thereof and the second therapeutic compound is a cancer therapeutic that is not artemesinin or a derivative thereof.

Aspects of the present specification disclose, in part, a pharmaceutical composition. As used herein, the term "pharmaceutically acceptable" means any molecular entity or composition that does not produce an adverse, allergic or other untoward or unwanted reaction when administered to an individual. As used herein, the term "pharmaceutically acceptable composition" is synonymous with "pharmaceutical composition" and means a therapeutically effective concentration of an active ingredient, such as, e.g., any of the therapeutic compounds disclosed herein. A pharmaceutical composition disclosed herein is useful for medical and veterinary applications. A pharmaceutical composition may be administered to an individual alone, or in combination with other supplementary active ingredients, agents, drugs or hormones.

A pharmaceutical composition disclosed herein may optionally include a pharmaceutically-acceptable carrier that facilitates processing of an active ingredient into pharmaceutically-acceptable compositions. As used herein, the term "pharmacologically-acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

In one embodiment, a pharmaceutical composition disclosed herein comprises a cancer therapeutic that has anti-cancer cell activity and a pharmaceutically-acceptable lipid formulation. In another embodiment, a pharmaceutical composition disclosed herein comprises a cancer therapeutic that has anti-cancer cell activity, a pharmaceutically-acceptable solvent, and a pharmaceutically-acceptable lipid formulation. In aspects of this embodiment, a pharmaceutical composition disclosed herein may further comprise a pharmaceutically-acceptable stabilizing agent. In other aspects of this embodiment, a pharmaceutical composition disclosed herein may further comprise a pharmaceutically-acceptable carrier, a pharmaceutically-acceptable component, or both pharmaceutically-acceptable carrier and pharmaceutically-acceptable component.

In a further embodiment, a pharmaceutical composition comprises a cancer therapeutic that includes, without limitation, at least one of a statin, a treatment for diabetes, an antibiotic, a helminthic, a malarial treatment a vitamin or a food additive. In an embodiment, a pharmaceutical composition includes, without limitation, a statin, a treatment for diabetes, and a helminthic. In another embodiment, a pharmaceutical composition includes, without limitation, a treatment for diabetes, a statin, an antibiotic and a food additive. Further embodiments can include other combinations of two or more cancer therapeutics.

In an embodiment, an individual that is administered a cancer therapeutic suffers mild or no side-effects as a result of the administered therapeutics.

In an embodiment, a cancer therapeutic is administered in conjunction with chemotherapy, radiation therapy, surgery, immunotherapy, including, without limitation, the derivation of stem cells and/or dendritic cells blood transfusions, lavages, and/or other treatments, including, without limitation, freezing a tumor. In a further embodiment, a cancer therapeutic is administered prior to or after the initiation and completion of chemotherapy, radiation therapy, immunotherapy, including, without limitation, the derivation of stem cells and/or dendritic cells blood transfusions, lavages, and/or other treatments, including, without limitation, freezing a tumor. In a further embodiment, a cancer therapeutic is administered, prior to, during and/or after administration of chemotherapy, radiation therapy, surgery, immunotherapy, including, without limitation, the derivation of stem cells and/or dendritic cells blood transfusions, lavages, and/or other treatments, including, without limitation, freezing a tumor.

A therapeutic compound disclosed herein, or a pharmaceutical composition comprising such a therapeutic compound, may be formulated for either local or systemic delivery using topical, enteral or parenteral routes of administration. Additionally, a therapeutic compound disclosed herein may be formulated by itself in a pharmaceutical composition, or may be formulated together with one or more other therapeutic compounds disclosed herein in a single pharmaceutical composition.

A therapeutic compound disclosed herein, or a pharmaceutical composition comprising such a therapeutic compound, may be made into an inhaled formulation. Inhaled formulations suitable for enteral or parenteral administration include, without limitation, aerosols, dry powders. A therapeutic compound or composition disclosed herein intended for such administration may be prepared according to any method known to the art for the manufacture of pharmaceutical compositions.

In such inhaled dosage forms, the therapeutic compound or a pharmaceutical composition may be prepared for delivery as an aerosol in a liquid propellant for use in a pressurised (PDI) or other metered dose inhaler (MDI). Propellants suitable for use in a PDI or MDI include, without limitation, CFC-12, HFA-134a, HFA-227, HCFC-22 (difluorochloromethane), HFA-152 (difluoroethane and isobutane). A therapeutic compound may also be delivered using a nebulisers or other aerosol delivery system. A therapeutic compound may be prepared for delivery as a dry powder for use in a dry powder inhaler (DPI). A dry powder for use in the inhalers will usually have a mass median aerodynamic diameter of less than 30 pm, preferably less than 20 pm and more preferably less than 10 pm. Microparticles having aerodynamic diameters in the range of about 5 pm to about 0.5 pm will generally be deposited in the respiratory bronchioles, whereas smaller particles, having aerodynamic diameters in the range of about 2 pm to about 0.05 pm, are likely to be deposited in the alveoli. A DPI may be a passive delivery mechanism, which relies on the individual's inspiration to introduce the particles into the lungs, or an active delivery mechanism, requiring a mechanism for delivering the powder to the individual. In inhalatory formulations, a therapeutically effective amount of a therapeutic compound disclosed herein for an inhaled formulation may be between about 0.0001% (w/v) to about 60% (w/v), about 0.001% (w/v) to about 40.0% (w/v), or about 0.01% (w/v) to about 20.0% (w/v). In inhalatory formulations, a therapeutically effective amount of a therapeutic compound disclosed herein for an inhaled formulation may also be between about 0.0001% (w/w) to about 60% (w/w), about 0.001% (w/w) to about 40.0% (w/w), or about 0.01% (w/w) to about 20.0% (w/w).

A therapeutic compound disclosed herein, or a pharmaceutical composition comprising such a therapeutic compound, may be made into a solid formulation. Solid formulations suitable for enteral or parenteral administration include, without limitation, capsules, tablets, pills, troches, lozenges, powders and granules suitable for inhalation or for reconstitution into sterile injectable solutions or dispersions. A therapeutic compound or composition disclosed herein intended for such administration may be prepared according to any method known to the art for the manufacture of pharmaceutical compositions. In such solid dosage forms, the therapeutic compound may be admixed with (a) at least one inert customary excipient (or carrier), such as, e.g., sodium citrate or dicalcium phosphate or (b) fillers or extenders, as for example, starch, lactose, sucrose, glucose, mannitol, isomalt, and silicic acid, (c) binders, such as, e.g., carboxymethylcellulose, alignates, gelatin, polyvinylpyrrolidone, sucrose and acacia, (d) humectants, such as, e.g., glycerol, (e) disintegrating agents, such as, e.g., agar-agar, calcium carbonate, corn starch, potato starch, tapioca starch, alginic acid, certain complex silicates and sodium carbonate, (f) solution retarders, such as, e.g., paraffin, (g) absorption accelerators, such as, e.g., quaternary ammonium compounds, (h) wetting agents, such as, e.g., cetyl alcohol and glycerol monostearate, (i) adsorbents, such as, e.g., kaolin and bentonite, (j) lubricants, such as, e.g., talc, stearic acid, calcium stearate, magnesium stearate, solid polyethylene glycols, sodium lauryl sulfate or mixtures thereof, and (k) buffering agents. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. In solid formulations, a therapeutically effective amount of a therapeutic compound disclosed herein typically may be between about 0.0001% (w/w) to about 60% (w/w), about 0.001% (w/w) to about 40.0% (w/w), or about 0.01% (w/w) to about 20.0% (w/w).

A therapeutic compound disclosed herein, or a pharmaceutical composition comprising such a therapeutic compound, may be made into a semi-solid formulation. Semi-solid formulations suitable for topical administration include, without limitation, ointments, creams, salves, and gels. A therapeutic compound or composition disclosed herein intended for such administration may be prepared according to any method known to the art for the manufacture of pharmaceutical compositions. In semi-solid formulations, a therapeutically effective amount of a therapeutic compound disclosed herein typically may be between about 0.0001% (w/v) to about 60% (w/v), about 0.001% (w/v) to about 40.0% (w/v), or about 0.01% (w/v) to about 20.0% (w/v). In semi-solid formulations, a therapeutically effective amount of a therapeutic compound disclosed herein typically may also be between about 0.0001% (w/w) to about 60% (w/w), about 0.001% (w/w) to about 40.0% (w/w), or about 0.01% (w/w) to about 20.0% (w/w).

A therapeutic compound disclosed herein, or a pharmaceutical composition comprising such a therapeutic compound, may be made into a liquid formulation. Liquid formulations suitable for enteral or parenteral administration include, without limitation, solutions, syrups, elixirs, dispersions, emulsions, and suspensions, including, but not limited, to those used for intravenous administration. A therapeutic compound or composition disclosed herein intended for such administration may be prepared according to any method known to the art for the manufacture of pharmaceutical compositions. In such liquid dosage forms, a therapeutic compound or composition disclosed herein may be admixed with (a) suitable aqueous and nonaqueous carriers, (b) diluents, (c) solvents, such as, e.g., water, ethanol, propylene glycol, polyethyleneglycol, glycerol, vegetable oils, such as, e.g., rapeseed oil and olive oil, and injectable organic esters such as ethyl oleate; and/or fluidity agents, such as, e.g., surfactants or coating agents like lecithin. In the case of dispersions and suspensions, fluidity can also be controlled by maintaining a particular particle size. In liquid formulations, a therapeutically effective amount of a therapeutic compound disclosed herein typically may be between about 0.0001% (w/v) to about 60% (w/v), about 0.001% (w/v) to about 40.0% (w/v), or about 0.01% (w/v) to about 20.0% (w/v).

Syrups and elixirs may be formulated with sweetening agents, for example glycerol, propylene glycol, sorbitol or sucrose. Such formulations may also contain a demulcent, a preservative, flavoring agents, and coloring agents.

Liquid suspensions may be formulated by suspending a therapeutic compound disclosed herein in admixture with excipients suitable for the manufacture of aqueous suspensions. Such excipients are suspending agents, for example sodium carboxymethylcellulose, methylcellulose, hydroxypropylmethylcellulose, sodium alginate, pectin, polyvinyl pyrrolidone, polyvinyl alcohol, natural gum, agar, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long-chain aliphatic alcohols, for example heptadecaethyleneoxycetanol, or condensation products of ethylene oxide with partial esters derived from fatty acids, for example polyoxyethylene sorbitan monooleate.

Oily suspensions may be formulated by suspending a therapeutic compound disclosed herein in admixture with (a) vegetable oils, such as, e.g., almond oil, arachis oil, avocado oil, canola oil, castor oil, coconut oil, corn oil, cottonseed oil, grape seed oil, hazelnut oil, hemp oil, linseed oil, olive oil, palm oil, peanut oil, rapeseed oil, rice bran oil, safflower oil, sesame oil, soybean oil, soya oil, sunflower oil, walnut oil, wheat germ oil, or a combination thereof, (b) a saturated fatty acid, an unsaturated fatty acid, or a combination thereof, such as, e.g., palmitic acid, stearic acid, oleic acid, linoleic acid, linolenic acid, or a combination thereof, (c) mineral oil such as, e.g., liquid paraffin, (d) surfactants or detergents. The oily suspensions may contain a thickening agent, for example beeswax, hard paraffin or cetyl alcohol.

Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the combined therapeutic compounds in admixture with a dispersing or wetting agent, suspending agent and one or more preservatives.

A therapeutic compound disclosed herein may be in the form of oil-in-water emulsions. The oily phase may be a vegetable oil as disclosed herein or a mineral oil as disclosed herein or mixtures thereof. Suitable emulsifying agents may be naturally occurring gums, such as, e.g., gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate.

A therapeutic compound disclosed herein, or a composition comprising such a therapeutic compound, may also be incorporated into a therapeutic compound delivery platform in order to achieve a controlled release profile over time. Such a therapeutic compound delivery platform comprises a therapeutic compound disclosed herein dispersed within a polymer matrix, typically a biodegradable, bioerodible, and/or bioresorbable polymer matrix. As used herein, the term "polymer" refers to synthetic homo- or copolymers, naturally occurring homo- or copolymers, as well as synthetic modifications or derivatives thereof having a linear, branched or star structure. Copolymers can be arranged in any form, such as, e.g., random, block, segmented, tapered blocks, graft, or triblock. Polymers are generally condensation polymers. Polymers can be further modified to enhance their mechanical or degradation properties by introducing cross-linking agents or changing the hydrophobicity of the side residues. If crosslinked, polymers are usually less than 5% crosslinked, usually less than 1% crosslinked.

Suitable polymers include, without limitation, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. The polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the therapeutic compound delivery platform. Examples of biodegradable, bioerodible, and/or bioresorbable polymers and methods useful to make a therapeutic compound delivery platform are described in, e.g., Drost, et. al., *Controlled Release Formulation*, U.S. Pat. No. 4,756,911; Smith, et. al., *Sustained Release Drug Delivery Devices*, U.S. Pat. No. 5,378,475; Wong and Kochinke, *Formulation for Controlled Release of Drugs by Combining Hyrophilic and Hydrophobic Agents*, U.S. Pat. No. 7,048,946; Hughes, et. al., *Compositions and Methods for Localized Therapy of the Eye*, U.S. Patent Publication 2005/0181017; Hughes, *Hypotensive Lipid-Containing Biodegradable Intraocular Implants and Related Methods*, U.S. Patent Publication 2005/0244464; Altman, et al., *Silk Fibroin Hydrogels and Uses Thereof*, U.S. Patent Publication 2011/0008437; each of which is incorporated by reference in its entirety.

In aspects of this embodiment, a polymer composing the matrix is a polypeptide such as, e.g., silk fibroin, keratin, or collagen. In other aspects of this embodiment, a polymer composing the matrix is a polysaccharide such as, e.g., cellulose, agarose, elastin, chitosan, chitin, or a glycosaminoglycan like chondroitin sulfate, dermatan sulfate, keratan sulfate, or hyaluronic acid. In yet other aspects of this embodiment, a polymer composing the matrix is a polyester such as, e.g., D-lactic acid, L-lactic acid, racemic lactic acid, glycolic acid, caprolactone, and combinations thereof.

One of ordinary skill in the art appreciates that the selection of a suitable polymer for forming a suitable disclosed therapeutic compound delivery platform depends on several factors. The more relevant factors in the selection of the appropriate polymer(s), include, without limitation, compatibility of polymer with a therapeutic compound, desired release kinetics of a therapeutic compound, desired biodegradation kinetics of platform at implantation site, desired bioerodible kinetics of platform at implantation site, desired bioresorbable kinetics of platform at implantation site, in vivo mechanical performance of platform, processing temperatures, biocompatibility of platform, and patient tolerance. Other relevant factors that, to some extent, dictate the in vitro and in vivo behavior of the polymer include the chemical composition, spatial distribution of the constituents, the molecular weight of the polymer and the degree of crystallinity.

A therapeutic compound delivery platform includes both a sustained release therapeutic compound delivery platform and an extended release therapeutic compound delivery platform. As used herein, the term "sustained release" refers to the release of a therapeutic compound disclosed herein over a period of about seven days or more. As used herein, the term "extended release" refers to the release of a therapeutic compound disclosed herein over a period of time of less than about seven days.

In aspects of this embodiment, a sustained release therapeutic compound delivery platform releases a therapeutic compound disclosed herein with substantially zero order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release therapeutic compound delivery platform releases a therapeutic compound disclosed herein with substantially zero order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a sustained release therapeutic compound delivery platform releases a therapeutic compound disclosed herein with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release therapeutic compound delivery platform releases a therapeutic compound disclosed herein with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a therapeutic compound delivery platform releases a therapeutic compound disclosed herein with substantially zero order release kinetics over a period of, e.g., about 1 day after administration, about 2 days after administration, about 3 days after administration, about 4 days after administration, about 5 days after administration, or about 6 days after administration. In other aspects of this embodiment, a therapeutic compound delivery platform releases a therapeutic compound disclosed herein with substantially zero order release kinetics over a period of, e.g., at most 1 day after administration, at most 2 days after administration, at most 3 days after administration, at most 4 days after administration, at most 5 days after administration, or at most 6 days after administration.

In aspects of this embodiment, a therapeutic compound delivery platform releases a therapeutic compound disclosed herein with substantially first order release kinetics over a period of, e.g., about 1 day after administration, about 2 days after administration, about 3 days after administration, about 4 days after administration, about 5 days after administration, or about 6 days after administration. In other aspects of this embodiment, a therapeutic compound delivery platform releases a therapeutic compound disclosed herein with substantially first order release kinetics over a period of, e.g., at most 1 day after administration, at most 2 days after administration, at most 3 days after administration, at most 4 days after administration, at most 5 days after administration, or at most 6 days after administration.

A therapeutic compound disclosed herein may have a log P value indicating that the compound is soluble in an organic solvent. As used herein, the term "log value" refers to the logarithm (base 10) of the partition coefficient (P) for a compound and is a measure of lipophilicity. Typically, P is defined as the ratio of concentrations of a unionized compound in the two phases of a mixture of two immiscible solvents at equilibrium. Thus, log P=Log 10 (P), where P=[solute in immiscible solvent 1]/[solute in immiscible solvent 2]. With regard to organic and aqueous phases, the log P value of a compound is constant for any given pair of aqueous and organic solvents, and its value can be determined empirically by one of several phase-partitioning methods known to one skilled in the art including, e.g., a shake flask assay, a HPLC assay, and an interface between two immiscible electrolyte solutions (ITIES) assay.

In aspects of this embodiment, a therapeutic compound disclosed herein may have a log P value indicating that the compound is substantially soluble in an organic solvent. In aspects of this embodiment, a therapeutic compound disclosed herein may have a log P value indicating that the compound is, e.g., at least 50% soluble in an organic solvent, at least 60% soluble in an organic solvent, at least 70% soluble in an organic solvent, at least 80% soluble in an organic solvent, or at least 90% soluble in an organic solvent. In aspects of this embodiment, a therapeutic compound disclosed herein may have a log P value indicating that the compound is between, e.g., about 50% to about 100% soluble in an organic solvent, about 60% to about 100% soluble in an organic solvent, about 70% to about 100% soluble in an organic solvent, about 80% to about 100% soluble in an organic solvent, or about 90% to about 100% soluble in an organic solvent.

In aspects of this embodiment, a therapeutic compound disclosed herein may have a log P value of, e.g., more than 1.1, more than 1.2, more than 1.4, more than 1.6, more than 1.8, more than 2.0, more than 2.2, more than 2.4, more than 2.6, more than 2.8, more than 3.0, more than 3.2, more than 3.4, or more than 3.6. In other aspects of this embodiment, a therapeutic compound disclosed herein may have a log P value in the range of, e.g., between 1.8 and 4.0, between 2.0 and 4.0, between 2.1 and 4.0, between 2.2 and 4.0, or between 2.3 and 4.0, between 2.4 and 4.0, between 2.5 and 4.0, between 2.6 and 4.0, or between 2.8 and 4.0. In other aspects of this embodiment, a therapeutic compound disclosed herein may have a log P value in the range of, e.g., between 3.0 and 4.0, or between 3.1 and 4.0, between 3.2 and 4.0, between 3.3 and 4.0, between 3.4 and 4.0, between 3.5 and 4.0, or between 3.6 and 4.0. In still other aspects of this embodiment, a therapeutic compound disclosed herein may have a log P value in the range of, e.g., between 2.0 and 2.5, between 2.0 and 2.7, between 2.0 and 3.0, or between 2.2 and 2.5.

A therapeutic compound disclosed herein may have a polar surface area that is hydrophobic. As used herein, the term "polar surface area" refers to the surface sum over all of the polar atoms in the structure of a compound and is a measure of hydrophobicity. Typically, these polar atoms include, e.g., oxygen, nitrogen, and their attached hydrogens. In aspects of this embodiment, a therapeutic compound disclosed herein may have a polar surface area of, e.g., less than 8.0 $nm^2$, less than 7.0 $nm^2$, less than 6.0 $nm^2$, less than 5.0 $nm^2$, less than 4.0 $nm^2$, or less than 3.0 $nm^2$. In other aspects of this embodiment, a therapeutic compound disclosed herein may have a polar surface area in the range of, e.g., between 3.0 $nm^2$ and 6.5 $nm^2$, between 3.0 $nm^2$ and 6.0 $nm^2$, between 3.0 $nm^2$ and 5.5 $nm^2$, between 3.0 $nm^2$ and 5.0 $nm^2$, between 3.0 $nm^2$ and 4.5 $nm^2$, between 3.5 $nm^2$ and 6.5 $nm^2$, between 3.5 $nm^2$ and 6.0 $nm^2$, between 3.5 $nm^2$ and 5.5 $nm^2$, between 3.5 $nm^2$ and 5.0 $nm^2$, between 3.5 $nm^2$ and 4.5 $nm^2$, between 4.0 $nm^2$ and 6.5 $nm^2$, between 4.0 $nm^2$ and 6.0 $nm^2$, between 4.0 $nm^2$ and 5.5 $nm^2$, or between 4.0 $nm^2$ and 5.0 $nm^2$, between 4.0 $nm^2$ and 4.5 $nm^2$, or between 4.5 $nm^2$ and 5.5 $nm^2$. In yet other aspects of this embodiment, a therapeutic compound disclosed herein may have a polar surface area in the range of, e.g., between 2.0 $nm^2$ and 6.5 $nm^2$, between 2.0 $nm^2$ and 6.0 $nm^2$, between 2.0 $nm^2$ and 5.5 $nm^2$, between 2.0 $nm^2$ and 5.0 $nm^2$, between 2.0 $nm^2$ and 4.5 $nm^2$, between 2.5 $nm^2$ and 6.5 $nm^2$, between 2.5 $nm^2$ and 6.0 $nm^2$, between 2.5 $nm^2$ and 5.5 $nm^2$, between 2.5 $nm^2$ and 5.0 $nm^2$, or between 2.5 $nm^2$ and 4.5 $nm^2$.

A therapeutic compound disclosed herein may be an ester of a therapeutic compound. An ester of a therapeutic compound increases the log P value relative to the same therapeutic compound, but without the ester modification. An ester group may be attached to a therapeutic compound by, e.g., a carboxylic acid or hydroxyl functional group present of the therapeutic compound. An ester of a therapeutic compound may have an increased hydrophobicity, and as such, may be dissolved in a reduced volume of solvent disclosed herein. In some instances, an ester of a therapeutic compound may be combined directly with an adjuvant disclosed herein, thereby eliminating the need of a solvent. An ester of a therapeutic compound may enable the making of a pharmaceutical composition disclosed herein, in situations where a non-esterified form of the same therapeutic compound is otherwise immiscible in a solvent disclosed herein. An ester of a therapeutic compound may still be delivered in a manner that more effectively inhibits a pro-inflammatory response as long as the compound is combined with an adjuvant disclosed herein. In one embodiment, a therapeutic compound may be reacted with ethyl ester in order to form an ethyl ester of the therapeutic compound.

In another embodiment, a pharmaceutical composition disclosed herein does not comprise a pharmaceutically-acceptable solvent disclosed herein. In an aspect of this embodiment, a pharmaceutical composition comprises a therapeutic compound and a pharmaceutically-acceptable adjuvant, but does not comprise a pharmaceutically-acceptable solvent disclosed herein.

Aspects of the present specification disclose, in part, a pharmaceutically-acceptable solvent. A solvent is a liquid, solid, or gas that dissolves another solid, liquid, or gaseous (the solute), resulting in a solution. Solvents useful in the pharmaceutical compositions disclosed herein include, without limitation, a pharmaceutically-acceptable polar aprotic solvent, a pharmaceutically-acceptable polar protic solvent and a pharmaceutically-acceptable non-polar solvent. A pharmaceutically-acceptable polar aprotic solvent includes, without limitation, dichloromethane (DCM), tetrahydrofuran (THF), ethyl acetate, acetone, dimethylformamide (DMF), acetonitrile (MeCN), dimethyl sulfoxide (DMSO). A pharmaceutically-acceptable polar protic solvent includes, without limitation, acetic acid, formic acid, ethanol, n-butanol, 1-butanol, 2-butanol, isobutanol, sec-butanol, tert-butanol, n-propanol, isopropanol, 1,2 propan-diol, methanol, glycerol, and water. A pharmaceutically-acceptable non-polar solvent includes, without limitation, pentane, cyclopentane, hexane, cyclohexane, benzene, toluene, 1,4-Dioxane, chloroform, n-methyl-pyrrilidone (NMP), and diethyl ether.

A pharmaceutical composition disclosed herein may comprise a solvent in an amount sufficient to dissolve a therapeutic compound disclosed herein. In other aspects of this embodiment, a pharmaceutical composition disclosed herein may comprise a solvent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a pharmaceutical composition disclosed herein may comprise a solvent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

In one embodiment, a solvent may comprise a pharmaceutically-acceptable alcohol. As used herein, the term "alcohol" refers to an organic molecule comprising a hydroxyl functional group (—OH) bond to a carbon atom, where the carbon atom is saturated. In aspects of this embodiment, the alcohol may be, e.g., a $C_{2-4}$ alcohol, a $C_{1-4}$ alcohol, a $C_{1-5}$ alcohol, a $C_{1-7}$ alcohol, a $C_{1-10}$ alcohol, a $C_{1-15}$ alcohol, or a $C_{1-20}$ alcohol. In other aspects of this embodiment, an alcohol may be, e.g., a primary alcohol, a secondary alcohol, or a tertiary alcohol. In other aspects of this embodiment, an alcohol may be, e.g., an acyclic alcohol, a monohydric alcohol, a polyhydric alcohol (also known as a polyol or sugar alcohol), an unsaturated aliphatic alcohol, an alicyclic alcohol, or a combination thereof. Examples of a monohydric alcohol include, without limitation, methanol, ethanol, propanol, butanol, pentanol, and 1-hexadecanol. Examples of a polyhydric alcohol include, without limitation, glycol, glycerol, arabitol, erythritol, xylitol, maltitol, sorbitol (gluctiol), mannitol, inositol, lactitol, galactitol (iditol), and isomalt. Examples of an unsaturated aliphatic alcohol include, without limitation, prop-2-ene-1-ol, 3,7-dimethylocta-2,6-dien-1-ol, and prop-2-in-1-ol. Examples of an alicyclic alcohol include, without limitation, cyclohexane-1,2,3,4,5,6-hexyl and 2-(2-propyl)-5-methyl-cyclohexane-1-ol.

In another embodiment, a solvent may comprise an ester of pharmaceutically-acceptable alcohol and an acid. Suitable pharmaceutically-acceptable alcohols include the ones disclosed herein. Suitable acids include, without limitation, acetic acid, butaric acid, and formic acid. An ester of an alcohol and an acid include, without limitation, methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate, and 1-hexadecyl formate.

In another embodiment, a solvent may comprise a pharmaceutically-acceptable glycol ether. Glycol ethers are a group of solvents based on alkyl ethers of ethylene glycol. Non-limiting examples include diethylene glycol monomethyl ether (2-(2-methoxyethoxy)ethanol), diethylene glycol monoethyl ether (2-(2-ethoxyethoxy)ethanol), diethylene glycol monopropyl ether (2-(2-propoxyethoxy)ethanol), diethylene glycol monoisopropyl ether (2-(2-isopropoxyethoxy)ethanol), and diethylene glycol mono-n-butyl ether (2-(2-butoxyethoxy)ethanol). Diethylene glycol monoethyl ether (2-(2-ethoxyethoxy)ethanol) is commercially available as TRANSCUTOL®.

In another embodiment, a solvent may comprise a pharmaceutically-acceptable diol. A diol or double alcohol is a chemical compound containing two hydroxyl groups (—OH groups).

In another embodiment, a solvent may comprise a pharmaceutically-acceptable propylene glycol. Propylene glycol, also called 1,2-propanediol or propane-1,2-diol, is an organic compound with formula $C_3H_8O_2$ or HO—CH$_2$—CHOH—CH$_3$.

In another embodiment, a solvent may comprise a pharmaceutically-acceptable dipropylene glycol. Dipropylene glycol is a mixture of three isomeric chemical compounds, 4-oxa-2,6-heptandiol, 2-(2-Hydroxy-propoxy)-propan-1-ol, and 2-(2-Hydroxy-1-methyl-ethoxy)-propan-1-ol.

In another embodiment, a solvent may comprise a pharmaceutically-acceptable polypropylene glycol (PPG) polymer. PPG polymers polymers, also known as polypropylene oxide (PPO) polymers or polyoxypropylene (POP) polymers, are prepared by polymerization of propylene oxide and are commercially available over a wide range of molecular weights from 100 g/mol to 10,000,000 g/mol. PPG polymers with a low molecular mass are liquids or low-melting solids, whereas PPG polymers of a higher molecular mass are solids. A PPG polymer include, without limitation, PPG 100, PPG 200, PPG 300, PPG 400, PPG 500, PPG 600, PPG 700, PPG 800, PPG 900, PPG 1000, PPG 1100, PPG 1200, PPG 1300, PPG 1400, PPG 1500, PPG 1600, PPG 1700, PPG 1800, PPG 1900, PPG 2000, PPG 2100, PPG 2200, PPG 2300, PPG 2400, PPG 2500, PPG 2600, PPG 2700, PPG 2800, PPG 2900, PPG 3000, PPG 3250, PPG 3350, PPG 3500, PPG 3750, PPG 4000, PPG 4250, PPG 4500, PPG 4750, PPG 5000, PPG 5500, PPG 6000, PPG 6500, PPG 7000, PPG 7500, PPG 8000, PPG 8500, PPG 9000, PPG 9500, PPG 10,000, PPG 11,000, PPG 12,000, PPG 13,000, PPG 14,000, PPG 15,000, PPG 16,000, PPG 17,000, PPG 18,000, PPG 19,000, or PPG 20,000.

In another embodiment, a solvent may comprise a pharmaceutically-acceptable polyethylene glycol (PEG) polymer. PEG polymers, also known as polyethylene oxide (PEO) polymers or polyoxyethylene (POE) polymers, are prepared by polymerization of ethylene oxide and are commercially available over a wide range of molecular weights from 100 g/mol to 10,000,000 g/mol. PEG polymers with a low molecular mass are liquids or low-melting solids, whereas PEG polymers of a higher molecular mass are solids. A PEG polymer include, without limitation, PEG 100, PEG 200, PEG 300, PEG 400, PEG 500, PEG 600, PEG 700, PEG 800, PEG 900, PEG 1000, PEG 1100, PEG 1200, PEG 1300, PEG 1400, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, PEG 5000, PEG 5500, PEG 6000, PEG 6500, PEG 7000, PEG 7500, PEG 8000, PEG 8500, PEG 9000, PEG 9500, PEG 10,000, PEG 11,000, PEG 12,000, PEG 13,000, PEG 14,000, PEG 15,000, PEG 16,000, PEG 17,000, PEG 18,000, PEG 19,000, or PEG 20,000.

In another embodiment, a solvent may comprise a pharmaceutically-acceptable glyceride. Glycerides comprise a substituted glycerol, where one, two, or all three hydroxyl groups of the glycerol are each esterified using a fatty acid to produce monoglycerides, diglycerides, and triglycerides, respectively. In these compounds, each hydroxyl groups of glycerol may be esterified by different fatty acids. Additionally, glycerides may be acetylated to produce acetylated monoglycerides, acetylated diglycerides, and acetylated triglycerides.

In one embodiment, a solvent may comprise a pharmaceutically-acceptable solid solvent. Solid solvents may be useful in the manufacture of a solid dose formulation of a pharmaceutical composition disclosed herein. Typically, a solid solvent is melted in order to dissolve a therapeutic compound. A pharmaceutically-acceptable solid solvent includes, without limitation, menthol and PEG polymers above about 20,000 g/mol.

Aspects of the present specification disclose, in part, a pharmaceutically-acceptable adjuvant. An adjuvant is a pharmacological agent that modifies the effect of other agents, such as, e.g., a therapeutic compound disclosed herein. In addition, an adjuvant disclosed herein may be used as a solvent that dissolves a therapeutic compound disclosed herein, forming a adjuvant solution. An adjuvant disclosed herein facilitates delivery of a therapeutic compound in a manner that more effectively inhibits a pro-inflammatory response. In one embodiment, an adjuvant disclosed herein facilitates the delivery of a therapeutic compound disclosed herein into macrophages.

A pharmaceutical composition disclosed herein may comprise a pharmaceutically-acceptable adjuvant in an amount sufficient to mix with a solution disclosed herein or an emulsion disclosed herein. In other aspects of this embodiment, a pharmaceutical composition disclosed herein may comprise an adjuvant in an amount of, e.g., at least 10% (v/v), at least 20% (v/v), at least 30% (v/v), at least 35% (v/v), at least 40% (v/v), at least 45% (v/v), at least 50% (v/v), at least 55% (v/v), at least 60% (v/v), at least 65% (v/v), at least 70% (v/v), at least 75% (v/v), at least 80% (v/v), at least 85% (v/v), at least 90% (v/v), at least 95% (v/v), or at least 99% (v/v). In other aspects of this embodiment, a pharmaceutical composition disclosed herein may comprise an adjuvant in an amount in a range of, e.g., about 30% (v/v) to about 99% (v/v), about 35% (v/v) to about 99% (v/v), about 40% (v/v) to about 99% (v/v), about 45% (v/v) to about 99% (v/v), about 50% (v/v) to about 99% (v/v), about 30% (v/v) to about 98% (v/v), about 35% (v/v) to about 98% (v/v), about 40% (v/v) to about 98% (v/v), about 45% (v/v) to about 98% (v/v), about 50% (v/v) to about 98% (v/v), about 30% (v/v) to about 95% (v/v), about 35% (v/v) to about 95% (v/v), about 40% (v/v) to about 95% (v/v), about 45% (v/v) to about 95% (v/v), or about 50% (v/v) to about 95% (v/v). In yet other aspects of this embodiment, a pharmaceutical composition disclosed herein may comprise an adjuvant in an amount in a range of, e.g., about 70% (v/v) to about 97% (v/v), about 75% (v/v) to about 97% (v/v), about 80% (v/v) to about 97% (v/v), about 85% (v/v) to about 97% (v/v), about 88% (v/v) to about 97% (v/v), about 89% (v/v) to about 97% (v/v), about 90% (v/v) to about 97% (v/v), about 75% (v/v) to about 96% (v/v), about 80% (v/v) to about 96% (v/v), about 85% (v/v) to about 96% (v/v), about 88% (v/v) to about 96% (v/v), about 89% (v/v) to about 96% (v/v), about 90% (v/v) to about 96% (v/v), about 75% (v/v) to about 93% (v/v), about 80% (v/v) to about 93% (v/v), about 85% (v/v) to about 93% (v/v), about 88% (v/v) to about 93% (v/v), about 89% (v/v) to about 93% (v/v), or about 90% (v/v) to about 93% (v/v).

In one embodiment, an adjuvant may be a pharmaceutically-acceptable lipid. A lipid may be broadly defined as a hydrophobic or amphiphilic small molecule. The amphiphilic nature of some lipids allows them to form structures such as vesicles, liposomes, or membranes in an aqueous environment. Non-limiting examples, of lipids include fatty acids, glycerolipids (like monoglycerides, diglycerides, and triglycerides), phospholipids, sphingolipids, sterol lipids, prenol lipids, saccharolipids, and polyketides. A pharmaceutical composition disclosed herein may comprise a lipid such as, e.g. an oil, an oil-based liquid, a fat, a fatty acid, a partially hydrolyzed fatty acid, a wax, a fatty acid ester, a fatty acid salt, a fatty alcohol, a glyceride (mono-, di- or tri-glyceride), a phospholipids, a glycol ester, a sucrose ester, a glycerol oleate derivative, a medium chain triglyceride, a partially hydrolyzed triglyceride, or a mixture thereof.

A lipid useful in the pharmaceutical compositions disclosed herein may be a pharmaceutically-acceptable fatty acid. A fatty acid comprises a carboxylic acid with a long unbranched hydrocarbon chain which may be either saturated or unsaturated. Thus arrangement confers a fatty acid with a polar, hydrophilic end, and a nonpolar, hydrophobic end that is insoluble in water. Most naturally occurring fatty acids have a hydrocarbon chain of an even number of carbon atoms, typically between 4 and 24 carbons, and may be attached to functional groups containing oxygen, halogens, nitrogen, and sulfur. Synthetic or non-natural fatty acids may have a hydrocarbon chain of any number of carbon atoms from between 3 and 40 carbons. Where a double bond exists, there is the possibility of either a cis or a trans geometric isomerism, which significantly affects the molecule's molecular configuration. Cis-double bonds cause the fatty acid chain to bend, an effect that is more pronounced the more double bonds there are in a chain. Most naturally occurring fatty acids are of the cis configuration, although the trans form does exist in some natural and partially hydrogenated fats and oils. Examples of fatty acids include, without limitation, Capryllic acid (8:0), pelargonic acid (9:0), Capric acid (10:0), Undecylic acid (11:0), Lauric acid (12:0), Tridecylic acid (13:0), Myristic acid (14:0), Myristoleic acid (14:1), Pentadecyclic acid (15:0), Palmitic acid (16:0), Palmitoleic acid (16:1), Sapienic acid (16:1), Margaric acid (17:0), Stearic acid (18:0), Oleic acid (18:1), Elaidic acid (18:1), Vaccenic acid (18:1), Linoleic acid (18:2), Linoelaidic acid (18:2), α-Linolenic acid (18:3), γ-Linolenic acid (18:3), Stearidonic acid (18:4), Nonadecylic acid (19:0), Arachidic acid (20:0), Eicosenoic acid (20:1), Dihomo-γ-linolenic acid (20:3), Mead acid (20:3), Arachidonic acid (20:4), Eicosapentaenoic acid (20:5), Heneicosylic acid (21:0), Behenic acid (22:0), Erucic acid (22:1), Docosahexaenoic acid (22:6), Tricosylic acid (23:0), Lignoceric acid (24:0), Nervonic acid (24:1), Pentacosylic acid (25:0), Cerotic acid (26:0), Heptacosylic acid (27:0), Montanic acid (28:0), Nonacosylic acid (29:0), Melissic acid (30:0), Henatriacontylic acid (31:0), Lacceroic acid (32:0), Psyllic acid (33:0), Geddic acid (34:0), Ceroplastic acid (35:0), and Hexatriacontylic acid (36:0).

A lipid useful in the pharmaceutical compositions disclosed herein may be a pharmaceutically-acceptable partially hydrogenated lipid. The process of hydrogenation adds hydrogen atoms to unsaturated lipid, eliminating double bonds and making them into partially or completely saturated lipid. Partial hydrogenation is a chemical rather than enzymatic, that converts a part of cis-isomers into trans-unsaturated lipids instead of hydrogenating them completely. In the first reaction step, one hydrogen is added, with the other, coordinatively unsaturated, carbon being attached to the catalyst. The second step is the addition of hydrogen to the remaining carbon, producing a saturated fatty acid. The first step is reversible, such that the hydrogen is readsorbed on the catalyst and the double bond is re-formed. The intermediate with only one hydrogen added contains no double bond and can freely rotate. Thus, the double bond can re-form as either cis or trans, of which trans is favored, regardless of the starting material.

In an embodiment, an adjuvant may be a pharmaceutically-acceptable saturated or unsaturated fatty acid. In aspects of this embodiment, a saturated or unsaturated fatty acid comprises, e.g., at least 8, at least 10, at least 12, at least 14, at least 16, at least 18, at least 20, at least 22, at least 24, at least 26, at least 28, or at least 30 carbon atoms, In other aspects of this embodiment, a saturated or unsaturated fatty acid comprises, e.g., between 4 and 24 carbon atoms, between 6 and 24 carbon atoms, between 8 and 24 carbon atoms, between 10 and 24 carbon atoms, between 12 and 24 carbon atoms, between 14 and 24 carbon atoms, or between 16 and 24 carbon atoms, between 4 and 22 carbon atoms, between 6 and 22 carbon atoms, between 8 and 22 carbon atoms, between 10 and 22 carbon atoms, between 12 and 22 carbon atoms, between 14 and 22 carbon atoms, or between 16 and 22 carbon atoms, between 4 and 20 carbon atoms, between 6 and 20 carbon atoms, between 8 and 20 carbon atoms, between 10 and 20 carbon atoms, between 12 and 20 carbon atoms, between 14 and 20 carbon atoms, or between 16 and 20 carbon atoms. If unsaturated, the fatty acid may have, e.g., 1 or more, 2 or more, 3 or more, 4 or more, 5 or more, or 6 or more double bonds.

In aspects of this embodiment, a pharmaceutically-acceptable saturated or unsaturated fatty acid is liquid at room temperature. The melting point of a fatty acid is largely determined by the degree of saturation/unsaturation of the hydrocarbon chain. In aspects of this embodiment, a saturated or unsaturated fatty acid has a melting point temperature of, e.g., 20° C. or below, 15° C. or below, 10° C. or below, 5° C. or below, 0° C. or below, −5° C. or below, −10° C. or below, −15° C. or below, or −20° C. or below. In other aspects of this embodiment, a saturated or unsaturated fatty acid has a melting point temperature in the range of, e.g., about −20° C. to about 20° C., about −20° C. to about 18° C., about −20° C. to about 16° C., about −20° C. to about 12° C., about −20° C. to about 8° C., about −20° C. to about 4° C., about −20° C. to about 0° C., about −15° C. to about 20° C., about −15° C. to about 18° C., about −15° C. to about 16° C., about −15° C. to about 12° C., about −15° C. to about 8° C., about −15° C. to about 4° C., about −15° C. to about 0° C.

In another embodiment, an adjuvant may comprise one kind of pharmaceutically-acceptable fatty acid. In aspects of this embodiment, an adjuvant may comprise only palmitic acid, only stearic acid, only oleic acid, only linoleic acid, or only linolenic acid.

In another embodiment, an adjuvant may comprise a plurality of different pharmaceutically-acceptable fatty acids. In aspects of this embodiment, an adjuvant may comprise, e.g., two or more different fatty acids, three or more different fatty acids, four or more different fatty acids, five or more different fatty acids, or six or more different fatty acids.

In other aspects of this embodiment, an adjuvant may comprise two or more different pharmaceutically-acceptable fatty acids including at least palmitic acid, stearic acid, oleic acid, linoleic acid and/or linolenic acid, and any combination thereof. In other aspects of this embodiment, an adjuvant may comprise a ratio of palmitic acid and/or stearic acid and/or oleic acid:linolenic acid and/or linoleic acid of, e.g., at least 2:1, at least 3:1, at least 4:1, at least 5:1, at least 6:1, at least 7:1, at least 8:1, at least 9:1, at least 10:1, at least 15:1, or at least 20:1. In yet other aspects of this embodiment, an adjuvant may comprise a ratio of palmitic acid and/or stearic acid and/or oleic acid:linolenic acid and/or linoleic acid in a range of, e.g., about 1:1 to about 20:1, about 2:1 to about 15:1, about 4:1 to about 12:1, or about 6:1 to about 10:1.

In other aspects of this embodiment, an adjuvant may comprise four or more different pharmaceutically-acceptable fatty acids including at least palmitic acid, stearic acid, oleic acid, linoleic acid and/or linolenic acid, and any combination thereof. In other aspects of this embodiment, an adjuvant may comprise a ratio of palmitic acid; stearic acid:linolenic acid:linoleic acid of, e.g., 10:10:1:1, 9:9:1:1, 8:8:1:1, 7:7:1:1, 6:6:1:1, 5:5:1:1, 4:4:1:1, 3:3:1:1, 2:2:1:1, or 1:1:1:1. In other aspects of this embodiment, an adjuvant may comprise a ratio of palmitic acid; stearic acid:linolenic acid:linoleic acid in a range of, e.g., about 10:10:1:1 to about 6:6:1:1, about 8:8:1:1 to about 4:4:1:1, or about 5:5:1:1 to about 1:1:1:1.

A lipid useful in the pharmaceutical compositions disclosed herein may be a pharmaceutically-acceptable omega fatty acid. Non-limiting examples of an omega fatty acid include omega-3, omega-6, omega-7, and omega-9. Omega-3 fatty acids (also known as n-3 fatty acids or ω-3 fatty acids) are a family of essential unsaturated fatty acids that have in common a final carbon-carbon double bond in the n-3 position, that is, the third bond, counting from the methyl end of the fatty acid. The omega-3 fatty acids are "essential" fatty acids because they are vital for normal metabolism and cannot be synthesized by the human body. An omega-3 fatty acid includes, without limitation, Hexadecatrienoic acid (16:3), α-Linolenic acid (18:3), Stearidonic acid (18:4), Eicosatrienoic acid (20:3), Eicosatetraenoic acid (20:4), Eicosapentaenoic acid (20:5), Heneicosapentaenoic acid (21:5), Docosapentaenoic acid (Clupanodonic acid) (22:5), Docosahexaenoic acid (22:6), Tetracosapentaenoic acid (24:5), Tetracosahexaenoic acid (Nisinic acid) (24:6).

Omega-6 fatty acids (also known as n-6 fatty acids or ω-6 fatty acids) are a family of unsaturated fatty acids that have in common a final carbon-carbon double bond in the n-6 position, that is, the sixth bond, counting from the methyl end of the fatty acid. An omega-6 fatty acid includes, without limitation, Linoleic acid (18:2), γ-linolenic acid (18:3), Calendic acid (18:3), Eicosadienoic acid (20:2), Dihomo-γ-linolenic acid (20:3), Arachidonic acid (20:4), Docosadienoic acid (22:2), Adrenic acid (22:4), Docosapentaenoic acid (22:5), Tetracosatetraenoic acid (24:4), and Tetracosapentaenoic acid (24:5).

Omega-7 fatty acids (also known as n-7 fatty acids or ω-7 fatty acids) are a family of unsaturated fatty acids that have in common a final carbon-carbon double bond in the n-7 position, that is, the seventh bond, counting from the methyl end of the fatty acid. An omega-7 fatty acid includes, without limitation, 5-Dodecenoic acid (12:1), 7-Tetradecenoic acid (14:1), 9-Hexadecenoic acid (Palmitoleic acid) (16:1), 11-Decenoic acid (Vaccenic acid) (18:1), 9Z,11E conjugated Linoleic acid (Rumenic acid) (18:2), 13-Eicosenoic acid (Paullinic acid) (20:1), 15-Docosenoic acid (22:1), and 17-Tetracosenoic acid (24:1).

Omega-9 fatty acids (also known as n-9 fatty acids or ω-9 fatty acids) are a family of unsaturated fatty acids that have in common a final carbon-carbon double bond in the n-9 position, that is, the ninth bond, counting from the methyl end of the fatty acid. An omega-9 fatty acid includes, without limitation, Oleic acid (18:1), Elaidic acid (18:1), Eicosenoic acid (20:1), Mead acid (20:3), Erucic acid (22:1), Nervonic acid (24:1), and Ricinoleic acid.

A lipid useful in the pharmaceutical compositions disclosed herein may be a pharmaceutically-acceptable fat. Also known as a hard fat or solid fat, a fat includes any fatty acid that is solid at normal room temperature, such as, e.g. about 20° C. Fats consist of a wide group of compounds that are generally soluble in organic solvents and generally insoluble in water. A fat suitable as a lipid useful in the pharmaceutical compositions disclosed herein, may be a triglyceride, a triester of glycerol or any of several fatty acids.

A lipid useful in the pharmaceutical compositions disclosed herein may be a pharmaceutically-acceptable oil. An oil, also known as a liquid fat, includes any fatty acid that is liquid at normal room temperature, such as, e.g. about 20° C. An oil suitable as a lipid useful in the pharmaceutical compositions disclosed herein, may be a natural oil, a vegetable oil or any substance that does not mix with water and has a greasy feel. Examples of suitable natural oils include, without limitation, mineral oil, triacetin, ethyl oleate, a hydrogenated natural oil, or a mixture thereof. Examples of suitable vegetable oils include, without limitation, almond oil, arachis oil, avocado oil, canola oil, castor oil, coconut oil, corn oil, cottonseed oil, grape seed oil, hazelnut oil, hemp oil, linseed oil (flax seed oil), olive oil, palm oil, peanut oil, rapeseed oil, rice bran oil, safflower oil, sesame oil, soybean oil, soya oil, sunflower oil, theobroma oil (cocoa butter), walnut oil, wheat germ oil, or a mixture thereof. Each of these oils is commercially available from a number of sources well recognized by those skilled in the art.

An oil is typically a mixture of various fatty acids. For example, Rapeseed oil, obtained from the seeds of *Brassica napus*, includes both omega-6 and omega-3 fatty acids in a ratio of about 2:1. As another example, linseed oil, obtained from the seeds of *Linum usitatissimum*, includes abut 7% palmitic acid, about 3.4-4.6% stearic acid, about 18.5-22.6% oleic acid, about 14.2-17% linoleic acid, and about 51.9-55.2% α-linolenic acid. As another example, *theobroma* oil, obtained from the seeds of *Theobroma cacao*, includes glycerides derived from palmitic acid, stearic acid, oleic acid, linoleic acid, and arichidic acid, with melting point of 34-38° C. In aspects of this embodiment, a pharmaceutical composition comprises an oil including at least two different fatty acids, at least three different fatty acids, at least four different fatty acids, at least five different fatty acids, or at least six different fatty acids.

A lipid useful in the pharmaceutical compositions disclosed herein may be a pharmaceutically-acceptable glycerolipid. Glycerolipids are composed mainly of mono-, di-, and tri-substituted glycerols. One group of glycerolipids is the glycerides, where one, two, or all three hydroxyl groups of glycerol are each esterified using a fatty acid to produce monoglycerides, diglycerides, and triglycerides, respectively. In these compounds, each hydroxyl groups of glycerol may be esterified by different fatty acids. Additionally, glycerides may be acetylated to produce acetylated monoglycerides, acetylated diglycerides, and acetylated triglycerides. One group of glycerolipids is the glycerides, where one, two, or all three hydroxyl groups of glycerol have sugar residues attached via a glycosidic linkage.

A lipid useful in the pharmaceutical compositions disclosed herein may be a pharmaceutically-acceptable glycol fatty acid ester. A pharmaceutically-acceptable glycol fatty acid ester can be a monoester of a glycol, a diester of a glycol, or a triester of a glycol. A glycol fatty acid ester include, without limitation, a ethylene glycol fatty acid ester, a diethylene glycol fatty acid ester, a propylene glycol fatty acid ester, and a dipropylene fatty acid ester. Non-limiting examples of glycol fatty acid esters include, e.g., ethelene glycol caprylate, ethelene glycol pelargonate, ethelene glycol caprate, ethelene glycol undecylate, ethelene glycol laurate, ethelene glycol tridecylate, ethelene glycol myristate, ethelene glycol myristolate, ethelene glycol pentadecyclate, ethelene glycol palmitate, ethelene glycol palmitoleate, ethelene glycol sapienate, ethelene glycol margarate, ethelene glycol stearate, ethelene glycol palmitostearate, ethelene glycol oleate, ethelene glycol elaidate, ethelene glycol vaccinate, ethelene glycol linoleate, ethelene glycol linoelaidate, ethelene glycol α-linolenate, ethelene glycol γ-linolenate, ethelene glycol stearidonate, ethelene glycol capprylocaprate, ethelene glycol dicapprylocaprate, diethelene glycol caprylate, diethelene glycol pelargonate, diethelene glycol caprate, diethelene glycol undecylate, diethelene glycol laurate, diethelene glycol tridecylate, diethelene glycol myristate, diethelene glycol myristolate, diethelene glycol pentadecyclate, diethelene glycol palmitate, diethelene glycol palmitoleate, diethelene glycol sapienate, diethelene glycol margarate, diethelene glycol stearate, diethelene glycol palmitostearate, diethelene glycol oleate, diethelene glycol elaidate, diethelene glycol vaccinate, diethelene glycol linoleate, diethelene glycol linoelaidate, diethelene glycol α-linolenate, diethelene glycol γ-linolenate, diethelene glycol stearidonate, diethelene glycol capprylocaprate, diethelene glycol dicapprylocaprate, propylene glycol caprylate, propylene glycol pelargonate, propylene glycol caprate, propylene glycol undecylate, propylene glycol laurate, propylene glycol tridecylate, propylene glycol myristate, propylene glycol myristolate, propylene glycol pentadecyclate, propylene glycol palmitate, propylene glycol palmitoleate, propylene glycol sapienate, propylene glycol margarate, propylene glycol stearate, propylene glycol palmitostearate, propylene glycol oleate, propylene glycol elaidate, propylene glycol vaccinate, propylene glycol linoleate, propylene glycol linoelaidate, propylene glycol α-linolenate, propylene glycol γ-linolenate, propylene glycol stearidonate, propylene glycol capprylocaprate, propylene glycol dicapprylocaprate, dipropylene glycol caprylate, dipropylene glycol pelargonate, dipropylene glycol caprate, dipropylene glycol undecylate, dipropylene glycol laurate, dipropylene glycol tridecylate, dipropylene glycol myristate, dipropylene glycol myristolate, dipropylene glycol pentadecyclate, dipropylene glycol palmitate, dipropylene glycol palmitoleate, dipropylene glycol sapienate, dipropylene glycol margarate, dipropylene glycol stearate, dipropylene glycol palmitostearate, dipropylene glycol oleate, dipropylene glycol elaidate, dipropylene glycol vaccinate, dipropylene glycol linoleate, dipropylene glycol linoelaidate, dipropylene glycol α-linolenate, dipropylene glycol γ-linolenate, dipropylene glycol stearidonate, dipropylene glycol caprylocaprate, dipropylene glycol dicapprylocaprate, or any combination thereof.

A lipid useful in the pharmaceutical compositions disclosed herein may be a pharmaceutically-acceptable polyether fatty acid ester. A pharmaceutically-acceptable polyether fatty acid ester can be a mono-fatty acid ester of a polyether, a di-fatty acid ester of a polyether, or a tri-fatty acid ester of a polyether. A polyether fatty acid ester includes, without limitation, a PEG fatty acid ester, a PEG glyceryl fatty acid, a PEG fatty acid ester glyceride, a PPG fatty acid ester, a PPG glyceryl fatty acid, and a PPG fatty acid ester glyceride. A PEG or PPG may be a molecular mass of, e.g., 5-20,000. Non-limiting examples of polyether fatty acid esters include, e.g., a PEG caprylate, a PEG pelargonate, a PEG caprate, a PEG undecylate, a PEG laurate, a PEG tridecylate, a PEG myristate, a PEG myristolate, a PEG pentadecyclate, a PEG palmitate, a PEG palmitoleate, a PEG sapienate, a PEG margarate, a PEG stearate, a PEG palmitostearate, PEG oleate, PEG elaidate, PEG vaccinate, PEG linoleate, PEG linoelaidate, PEG α-linolenate, PEG γ-linolenate, PEG stearidonate, PEG capprylocaprate, PEG dicapprylocaprate, a PEG glyceryl caprylate, a PEG glyceryl pelargonate, a PEG glyceryl caprate, a PEG glyceryl undecylate, a PEG glyceryl laurate, a PEG glyceryl tridecylate, a PEG glyceryl myristate, a PEG glyceryl myristolate, a PEG glyceryl pentadecyclate, a PEG glyceryl palmitate, a PEG glyceryl palmitoleate, a PEG glyceryl sapienate, a PEG glyceryl margarate, a PEG glyceryl stearate, a PEG glyceryl palmitostearate, PEG glyceryl oleate, PEG glyceryl elaidate, PEG glyceryl vaccinate, PEG glyceryl linoleate, PEG glyceryl linoelaidate, PEG glyceryl α-linolenate, PEG glyceryl γ-linolenate, PEG glyceryl stearidonate, PEG glyceryl capprylocaprate, PEG glyceryl dicapprylocaprate, a capryloyl PEG glyceride, a pelargonoyl PEG glyceride, a caproyl PEG glyceride, an undecyloyl PEG glyceride, a lauroyl PEG glyceride, a tridecyloyl PEG glyceride, a myristoyl PEG glyceride, a myristoloyl PEG glyceride, a pentadecycloyl PEG glyceride, a palmitoyl PEG glyceride, a palmitoleoyl PEG glyceride, a sapienoyl PEG glyceride, a margaroyl PEG glyceride, a stearoyl PEG glyceride, a palmitostearoyl PEG glyceride, an oleoyl PEG glyceride, an elaidoyl PEG glyceride, a vaccinoyl PEG glyceride, a linoleoyl PEG glyceride, a linoelaidoyl PEG glyceride, an α-linolenoyl PEG glyceride, a γ-linolenoyl PEG glyceride, a stearidonoyl PEG glyceride, a capprylocaproyl PEG glyceride, a dicapprylocaproyl PEG glyceride, a PPG caprylate, a PPG pelargonate, a PPG caprate, a PPG undecylate, a PPG laurate, a PPG tridecylate, a PPG myristate, a PPG myristolate, a PPG pentadecyclate, a PPG palmitate, a PPG palmitoleate, a PPG sapienate, a PPG margarate, a PPG stearate, a PPG palmitostearate, a PPG oleate, a PPG elaidate, a PPG vaccinate, a PPG linoleate, a PPG linoelaidate, a PPG α-linolenate, a PPG γ-linolenate, a PPG stearidonate, a PPG capprylocaprate, a PPG dicapprylocaprate, a PPG glyceryl caprylate, a PPG glyceryl pelargonate, a PPG glyceryl caprate, a PPG glyceryl undecylate, a PPG glyceryl laurate, a PPG glyceryl tridecylate, a PPG glyceryl myristate, a PPG glyceryl myristolate, a PPG glyceryl pentadecyclate, a PPG glyceryl palmitate, a PPG glyceryl palmitoleate, a PPG glyceryl sapienate, a PPG glyceryl margarate, a PPG glyceryl stearate, a PPG glyceryl palmitostearate, a PPG glyceryl oleate, a PPG glyceryl elaidate, a PPG glyceryl vaccinate, a PPG glyceryl linoleate, a PPG glyceryl linoelaidate, a PPG glyceryl α-linolenate, a PPG glyceryl γ-linolenate, a PPG glyceryl stearidonate, a PPG glyceryl capprylocaprate, a PPG glyceryl dicapprylocaprate, a capryloyl PPG glyceride, a pelargonoyl PPG glyceride, a caproyl PPG glyceride, an undecyloyl PPG glyceride, a lauroyl PPG glyceride, a tridecyloyl PPG glyceride, a myristoyl PPG glyceride, a myristoloyl PPG glyceride, a pentadecycloyl PPG glyceride, a palmitoyl PPG glyceride, a palmitoleoyl PPG glyceride, a sapienoyl PPG glyceride, a margaroyl PPG glyceride, a stearoyl PPG glyceride, a palmitostearoyl PPG glyceride, an oleoyl PPG glyceride, an elaidoyl PPG glyceride, a vaccinoyl PPG glyceride, a linoleoyl PPG glyceride, a linoelaidoyl PPG glyceride, an α-linolenoyl PPG glyceride, a γ-linolenoyl PPG glyceride, a stearidonoyl PPG glyceride, a capprylocaproyl PPG glyceride, a dicapprylocaproyl PPG glyceride, or any combination thereof.

Commercially available pharmaceutically-acceptable polyether fatty acid esters include, without limitation, caprylocaproyl macrogol-8 glycerides (LABRASOL®), propylene glycol monopalmitostearate (MONOSTEOL®), glyceryl dibehenate (COMPRITOL® 888), glycerol behenate (COMPRITOL® E ATO), behenoyl pollyoxyl-8 glycerides (COMPRITOL® HD5 ATO), triglycerol diisostearate (PLUROL® Diisostearique), PEG-8 beeswax (APIFIL®), lauroyl macrogol-32 glycerides (GELUCIRE 44/14), stearoyl macrogol-32 glycerides (GELUCIRE 50.13), propylene glycol dicaprylocaprate (LABRAFAC® PG), polyglycerol-3 dioleate (PLUROL® Oleique CC 497), propylene glycol monolaurate (type I) (LAUROGLYCOL® FCC), propylene glycol monolaurate (type II) (LAUROGLYCOL® 90), propylene glycol monocaprylate (type I) (CAPRYOL® PGMC), propylene glycol monocaprylate (type II) (CAPRYOL® 90), linoleoyl macrogol-6 glycerides (LABRAFIL® M2125CS), oleoyl macrogol-6 glycerides (LABRAFIL® M1944CS), lauroyl macrogol-6 glycerides (LABRAFIL® M2130CS), glycerol dipalmitostearate (Biogapress Vegetal BM297ATO), glycerol distearate (type I) (PRECIROL® ATO 5), and glycerol monolinoleate (MAISINE™ 35-1).

A lipid useful in the pharmaceutical compositions disclosed herein may be a mixture of pharmaceutically-acceptable lipids. Examples of mixtures of pharmaceutically-acceptable lipids include, without limitation, a mixture of one or more glycerolipids disclosed herein, one or more glycol fatty acid esters disclosed herein, more polyether fatty acid esters disclosed herein. In aspects of this embodiment, a mixture of pharmaceutically-acceptable lipids includes a mixture of mono-, di-, and triglycerides and PEG fatty acid esters having a melting point of about 33° C., a mixture of mono-, di-, and triglycerides and PEG fatty acid esters having a melting point of about 35° C., a mixture of mono-, di-, and triglycerides and PEG fatty acid esters having a melting point of about 37° C., a mixture of mono-, di-, and triglycerides and PEG fatty acid esters having a melting point of about 39° C., a mixture of pharmaceutically-acceptable lipids includes mono-, di-, and triglycerides and PEG fatty acid esters having a melting point of about 41° C., a mixture of pharmaceutically-acceptable lipids includes mono-, di-, and triglycerides and PEG fatty acid esters having a melting point of about 43° C., or a mixture of pharmaceutically-acceptable lipids includes mono-, di-, and triglycerides and PEG fatty acid esters having a melting point of about 45° C. Commercially available mixtures of pharmaceutically-acceptable lipids include, without limitation, mixtures of PEG-6 stearate and ethylene glycol palmitostearate and PEG-32 stearate (TEFOSE® 1500; TEFOSE® 63), mixtures of triceteareth-4 phosphate and ethylene glycol palmitostearate and diethylene glycol palmitostearate (SEDEFOS® 75), mixtures of glycerol monostearate and PEG-75 stearate (GELOT®), mixtures of cetyl alcohol and ethoxylated fatty alcohols (seteth-2-, steareth-20) (EMULCIRE®), mixtures of mono-, di-, and triglycerides and PEG fatty acid esters having a melting point around 33° C. (GELUCIRE® 33/01), mixtures of mono-, di-, and triglycerides and PEG fatty acid esters having a melting point around 39° C. (GELUCIRE® 39/01), mixtures of mono-, di-, and triglycerides and PEG fatty acid esters having a melting point around 43° C. (GELUCIRE® 43/01), mixtures of glycerol monostearate 40-55 (type I) and diglycerides (GELEOL® Mono and Diglycerides), and mixtures of medium-chain triglycerides (LABRAFAC® Lipophile WL 1349).

Aspects of the present specification disclose, in part, a pharmaceutically-acceptable stabilizing agent. A stabilizing agent reduces or eliminates formation of esters of a therapeutic compound that may result as a unwanted reaction with the particular solvent used. A stabilizing agent include, without limitation, water, a sacrificial acid comprising a fatty acid component and acetic acid, ethyl acetate, a sodium acetate/acetic acid (E262), a monoglyceride, an acetylated monoglyceride, a diglyceride, an acetylated monoglyceride, an acetylated diglyceride, a fatty acid, and a fatty acid salt.

In one embodiment, a pharmaceutically-acceptable stabilizing agent may comprise a pharmaceutically-acceptable emulsifying agent. An emulsifying agent (also known as an emulgent) is a substance that stabilizes an emulsion comprising a liquid dispersed phase and a liquid continuous phase by increasing its kinetic stability. Thus, in situations where the solvent and adjuvant used to make a pharmaceutical composition disclosed herein are normally immiscible, an emulsifying agent disclosed herein is used to create a homogenous and stable emulsion. An emulsifying agent includes, without limitation, a surfactant, a polysaccharide, a lectin, and a phospholipid.

In an aspect of this embodiment, an emulsifying agent may comprise a surfactant. As used hereon, the term "surfactant" refers to a natural or synthetic amphiphilic compound. A surfactant can be non-ionic, zwitterionic, or ionic. Non-limiting examples of surfactants include polysorbates like polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate 80 (TWEEN® 80), and polysorbate 81 (TWEEN® 81); poloxamers (polyethylene-polypropylene copolymers), like Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), Poloxamer 407 (PLURONIC® F127), polyoxyethyleneglycol dodecyl ethers, like BRIJ® 30, and BRIJ® 35; 2-dodecoxyethanol (LUBROL®-PX); polyoxyethylene octyl phenyl ether (TRITON® X-100); sodium dodecyl sulfate (SDS); 3-[(3-Cholamidopropyl)dimethylammonio]-1-propanesulfonate (CHAPS); 3-[(3-Cholamidopropyl)dimethylammonio]-2-hydroxy-1-propanesulfonate (CHAPSO); sucrose monolaurate; and sodium cholate. Other non-limiting examples of surfactant excipients can be found in, e.g., Ansel, supra, (1999); Gennaro, supra, (2000); Hardman, supra, (2001); and Rowe, supra, (2003), each of which is hereby incorporated by reference in its entirety.

In an aspect of this embodiment, an emulsifying agent may comprise a polysaccharide. Non-limiting examples of polysaccharides include guar gum, agar, alginate, calgene, a dextran (like dextran 1K, dextran 4K, dextran 40K, dextran 60K, and dextran 70K), dextrin, glycogen, inulin, starch, a starch derivative (like hydroxymethyl starch, hydroxyethyl starch, hydroxypropyl starch, hydroxybutyl starch, and hydroxypentyl starch), hetastarch, cellulose, FICOLL, methyl cellulose (MC), carboxymethyl cellulose (CMC), hydroxyethyl cellulose (HEC), hydroxypropyl cellulose (HPC), hydroxyethyl methyl cellulose (HEMC), hydroxypropyl methyl cellulose (HPMC); polyvinyl acetates (PVA); polyvinyl pyrrolidones (PVP), also known as povidones, having a K-value of less than or equal to 18, a K-value greater than 18 or less than or equal to 95, or a K-value greater than 95, like PVP 12 (KOLLIDON® 12), PVP 17 (KOLLIDON® 17), PVP 25 (KOLLIDON® 25), PVP 30 (KOLLIDON® 30), PVP 90 (KOLLIDON® 90); and polyethylene imines (PEI).

In an aspect of this embodiment, an emulsifying agent may comprise a lectin. Lectins are sugar-binding proteins that are highly specific for their sugar moieties. Lectins may be classified according to the sugar moiety that they bind to, and include, without limitation, mannose-binding lectins, galactose/N-acetylgalactosamine-binding lectins, N-acetylgluxosamine-binding lectins, N-acetylneuramine-binding lectins, N-acetylneuraminic acid-binding lectins, and fucose-binding lectins. Non-limiting examples of surfactants include concanavain A, lentil lectin, snowdrop lectin, Roin, peanut agglutinin, jacain, hairy vetch lectin, wheat germ agglutinin, elderberry lectin, *Maackia anurensis* leukoagglutinin, *Maackia anurensis* hemoagglutinin, *Ulex europaeus* agglutinin, and *Aleuria aurantia* lectin.

In an aspect of this embodiment, an emulsifying agent may comprise a phospholipid. The structure of the phospholipid generally comprises a hydrophobic tail and a hydrophilic head and is amphipathic in nature. Most phospholipids contain a diglyceride, a phosphate group, and a simple organic molecule such as choline; one exception to this rule is sphingomyelin, which is derived from sphingosine instead of glycerol. Phospholipids include, without limitation, diacylglycerides and phosphosphingolipids. Non-limiting examples of diacylglycerides include a phosphatidic acid (phosphatidate) (PA), a phosphatidylethanolamine (cephalin) (PE), a phosphatidylcholine (lecithin) (PC), a phosphatidylserine (PS), and a phosphoinositide including phosphatidylinositol (PI), phosphatidylinositol phosphate (PIP), phosphatidylinositol bisphosphate (PIP2), and phosphatidylinositol triphosphate (PIP3). Non-limiting examples of phosphosphingolipids include a ceramide phosphorylcholine (sphingomyelin) (SPH), ceramide phosphorylethanolamine (sphingomyelin) (Cer-PE), and ceramide phosphorylglycerol.

In one embodiment, a pharmaceutically-acceptable stabilizing agent does not comprise a pharmaceutically-acceptable emulsifying agent.

In another embodiment, a pharmaceutical composition does not comprise a pharmaceutically-acceptable emulsifying agent.

The pharmaceutical compositions disclosed herein act as a delivery system that enable a therapeutic compound disclosed herein to be more effectively delivered or targeted to a cell type, tissue, organ, or region of the body in a manner that more effectively inhibits a pro-inflammatory response. This inhibition results in an improved treatment of a chronic inflammation. For example, a pharmaceutical composition disclosed herein may facilitate the delivery of a therapeutic compound disclosed herein into macrophages. One possible mechanism that achieves this selective biodistribution is that the pharmaceutical compositions disclosed herein may be designed to take advantage of the activity of chylomicrons. Chylomicrons are relatively large lipoprotein particles having a diameter of 75 nm to 1,200 nm. Comprising triglycerides (85-92%), phospholipids (6-12%), cholesterol (1-3%) and apolipoproteins (1-2%), chylomicrons transport dietary lipids from the intestines to other locations in the body. Chylomicrons are one of the five major groups of lipoproteins, the others being VLDL, IDL, low-density lipoproteins (LDL), high-density lipoproteins (HDL), that enable fats and cholesterol to move within the water-based solution of the bloodstream.

During digestion, fatty acids and cholesterol undergo processing in the gastrointestinal tract by the action of pancreatic juices including lipases and emulsification with bile salts to generate micelles. These micelles allow the absorption of lipid as free fatty acids by the absorptive cells of the small intestine, known as enterocytes. Once in the enterocytes, triglycerides and cholesterol are assembled into nascent chylomicrons. Nascent chylomicrons are primarily composed of triglycerides (85%) and contain some cholesterol and cholesteryl esters. The main apolipoprotein component is apolipoprotein B-48 (APOB48). These nascent chylomicrons are released by exocytosis from enterocytes into lacteals, lymphatic vessels originating in the villi of the small intestine, and are then secreted into the bloodstream at the thoracic duct's connection with the left subclavian vein.

While circulating in lymph and blood, chylomicrons exchange components with HDL. The HDL donates apolipoprotein C-II (APOC2) and apolipoprotein E (APOE) to the nascent chylomicron and thus converts it to a mature chylomicron (often referred to simply as "chylomicron"). APOC2 is the cofactor for lipoprotein lipase (LPL) activity. Once triglyceride stores are distributed, the chylomicron returns APOC2 to the HDL (but keeps APOE), and, thus, becomes a chylomicron remnant, now only 30-50 nm. APOB48 and APOE are important to identify the chylomicron remnant in the liver for endocytosis and breakdown into lipoproteins (VLDL, LDL and HDL). These lipoproteins are processed and stored by competent cells, including, e.g., hepatocytes, adipocytes and macrophages. Thus, without wishing to be limited by any theory, upon oral administration, a pharmaceutical composition disclosed herein can be processed into micelles while in the gastrointestinal tract, absorbed by enterocytes and assembled into nascent chylomicrons, remain associated with chylomicron remnants taken up by the liver, and ultimately loaded into macrophages which are present in inflamed tissues.

As another example, a pharmaceutical composition disclosed herein may facilitate the delivery of a therapeutic compound disclosed herein into dentritic cells. One possible mechanism to achieve selective biodistribution of the pharmaceutical compositions disclosed herein may be to take advantage of the endocytotic/phagocytotic activity of dentritic cells. Dendritic cells are immune cells forming part of the mammalian immune system. The main function of dendritic cells is to process antigen material and present it on the surface to other cells of the immune system. Thus, dendritic cells function as antigen-presenting cells that act as messengers between innate and adaptive immunity. Dendritic cells are present in tissues in contact with the external environment, such as, e.g., the skin (where there is a specialized dendritic cell type called Langerhans cells) and the inner lining of the nose, lungs, stomach and intestines. These cells can also be found in an immature state in the blood. Once activated, they migrate to the lymph nodes where they interact with T cells and B cells to initiate and shape the adaptive immune response. Dendritic cells are known to endocytose and phagocytose lipid particles as part of their environmental monitoring and antigen presentation processes. Without wishing to be limited by any theory, upon topical or inhalatory administration, a pharmaceutical composition disclosed herein can penetrate into the skin or inner lining of the nose, lungs, stomach and intestines, be endocytosed/phagocytosed by dentritic cells, and ultimately loaded into T cells and/or B cells which are present in inflamed tissues.

Aspects of the present specification disclose, in part, a method of preparing a pharmaceutical composition disclosed herein. A method disclosed herein comprises the step of contacting a pharmaceutically-acceptable adjuvant disclosed herein with a therapeutic compound disclosed herein under conditions which allow the therapeutic compound to dissolve in the pharmaceutically-acceptable adjuvant, thereby forming a pharmaceutical composition disclosed herein.

Aspects of the present specification disclose, in part, a method of preparing a pharmaceutical composition disclosed herein. A method disclosed herein comprises the steps of a) contacting a pharmaceutically-acceptable solvent disclosed herein with a therapeutic compound disclosed herein under conditions which allow the therapeutic compound to dissolve in the pharmaceutically-acceptable solvent, thereby forming a solution; and b) contacting the solution formed in step (a) with a pharmaceutically-acceptable adjuvant disclosed herein under conditions which allow the formation of a pharmaceutical composition. The methods of preparing disclosed herein may further comprise a step (c) of removing the pharmaceutically-acceptable solvent from the pharmaceutical composition.

The amount of a therapeutic compound that is contacted with the pharmaceutically-acceptable solvent in step (a) of the method may be in any amount desired. Factors used to determine the amount of a therapeutic compound used include, without limitation, the final amount the therapeutic compound desired in the pharmaceutical composition, the desired concentration of a therapeutic compound in the solution, the hydrophobicity of the therapeutic compound, the lipophobicity of the therapeutic compound, the temperature under which the contacting step (a) is performed, and the time under which the contacting step (a) is performed The volume of a pharmaceutically-acceptable solvent used in step (a) of the method may be any volume desired.

Factors used to determine the volume of a pharmaceutically-acceptable solvent used include, without limitation, the final amount of a pharmaceutical composition desired, the desired concentration of a therapeutic compound in the solution, the hydrophobicity of the therapeutic compound, and the lipophobicity of the therapeutic compound.

In aspects of this embodiment, the amount of a therapeutic compound that is contacted with the solvent in step (a) may be, e.g., at least 10 mg, at least 20 mg, at least 30 mg, at least 40 mg, at least 50 mg, at least 60 mg, at least 70 mg, at least 80 mg, at least 90 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg. In other aspects of this embodiment, the amount of a therapeutic compound that is contacted with the solvent in step (a) may be in the range of, e.g., about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In other aspects of this embodiment, the amount of a therapeutic compound that is dissolved in the solvent in step (a) may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, or about 200 mg to about 1,500 mg.

Step (a) may be carried out at room temperature, in order to allow a therapeutic compound to dissolve fully in the pharmaceutically-acceptable solvent. However, in other embodiments of the method, Step (a) may be carried out at a temperature that is greater than room temperature. In aspects of this embodiment, Step (a) may be carried out at a temperature that is, e.g., greater than 21° C., greater than 25° C., greater than 30° C., greater than 35° C. or greater than 37° C., greater than 40° C., greater than 42° C., greater than 45° C., greater than 50° C., greater than 55° C., or greater than 60° C. In aspects of this embodiment, Step (a) may be carried out at a temperature that is between, e.g., about 20° C. to about 30° C., about 25° C. to about 35° C., about 30° C. to about 40° C., about 35° C. to about 45° C., about 40° C. to about 50° C., about 45° C. to about 55° C., or about 50° C. to about 60° C. In certain cases, Step (a) may be carried out at temperatures below room temperature, in order to allow a therapeutic compound to dissolve fully in solvent. However, in other embodiments of the method, step (a) may be carried out at a temperature that is less than room temperature, e.g., less than 10° C., greater than 5° C., greater than 0° C., greater than −10° C. or greater than −20° C. The contacting in Step (a) may comprise mixing the therapeutic compound and the pharmaceutically-acceptable solvent, e.g., by stirring, inversion, sonication, or vortexing. The mixing may be carried out for, e.g., at least 1 second, at least 5 seconds, at least 10 seconds, at least 20 seconds, at least 30 seconds, at least 45 seconds, at least 60 seconds, or more, until the therapeutic compound is fully dissolved in the solvent.

After contacting, the concentration of a therapeutic compound disclosed herein in the solution may be in any concentration desired. In aspects of this embodiment, the concentration of a therapeutic compound disclosed herein in the solution may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the concentration of a therapeutic compound disclosed herein in the solution may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

The volume of a pharmaceutically-acceptable adjuvant used in Step (b) of the method may be any volume desired. Factors used to determine the volume of a pharmaceutically-acceptable adjuvant used include, without limitation, the final amount of a pharmaceutical composition desired, the desired concentration of a therapeutic compound in the pharmaceutical composition, the ratio of solvent:adjuvant used, and the miscibility of solvent and adjuvant.

In aspects of this embodiment, the ratio of solution:adjuvant may be, e.g., at least 5:1, at least 4:1, at least 3:1, at least 2:1, at least 0:1, at least 1:1, at least 1:2, at least 1:3, at least 1:4, at least 1:5, at least 1:6, at least 1:7, at least 1:8, at least 1:9, at least 1:10, at least 1:15, at least 1:20, or at least 1:25. In other aspects of this embodiment, the ratio of solution:adjuvant may be in a range of, e.g., about 5:1 to about 1:25, about 4:1 to about 1:25, about 3:1 to about 1:25, about 2:1 to about 1:25, about 0:1 to about 1:25, about 1:1 to about 1:25, about 1:2 to about 1:25, about 1:3 to about 1:25, about 1:4 to about 1:25, about 1:5 to about 1:25, about 5:1 to about 1:20, about 4:1 to about 1:20, about 3:1 to about 1:20, about 2:1 to about 1:20, about 0:1 to about 1:20, about 1:1 to about 1:20, about 1:2 to about 1:20, about 1:3 to about 1:20, about 1:4 to about 1:20, about 1:5 to about 1:20, about 5:1 to about 1:15, about 4:1 to about 1:15, about 3:1 to about 1:15, about 0:1 to about 1:15, about 2:1 to about 1:15, about 1:1 to about 1:15, about 1:2 to about 1:15, about 1:3 to about 1:15, about 1:4 to about 1:15, about 1:5 to about 1:15, about 5:1 to about 1:12, about 4:1 to about 1:12, about 3:1 to about 1:12, about 2:1 to about 1:12, about 0:1 to about 1:12, about 1:1 to about 1:12, about 1:2 to about 1:12, about 1:3 to about 1:12, about 1:4 to about 1:12, about 1:5 to about 1:12, about 1:6 to about 1:12, about 1:7 to about 1:12, about 1:8 to about 1:12, about 5:1 to about 1:10, about 4:1 to about 1:10, about 3:1 to about 1:10, about 2:1 to about 1:10, about 0:1 to about 1:10, about 1:1 to about 1:10, about 1:2 to about 1:10, about 1:3 to about 1:10, about 1:4 to about 1:10, about 1:5 to about 1:10, about 1:6 to about 1:10, about 1:7 to about 1:10, or about 1:8 to about 1:10.

In an embodiment, the ratio of fat:fat, for instance, without limitation, tributyrin, which is an ester composed of butyric acid and glycerol and G43 (a sold fat) may be, e.g., at least 5:1, at least 4:1, at least 3:1, at least 2:1, at least 0:1, at least 1:1, at least 1.1:1, at least 1.2:1, at least 1.3:1, at least 1.4:1, at least 1.5:1, at least 1.6:1, at least 1.7:1, at least 1.8:1, at least 1.9:1, at least 1:2, at least 1:3, at least 1:4, at least 1:5, at least 1:6, at least 1:7, at least 1:8, at least 1:9, at least 1:10, at least 1:15, at least 1:20, or at least 1:25. In other aspects of this embodiment, the ratio of fat:fat may be in a range of, e.g., about 5:1 to about 1:25, about 4:1 to about 1:25, about 3:1 to about 1:25, about 2:1 to about 1:25, about 0:1 to about 1:25, about 1:1 to about 1:25, about 1:2 to about 1:25, about 1:3 to about 1:25, about 1:4 to about 1:25, about 1:5 to about 1:25, about 5:1 to about 1:20, about 4:1 to about 1:20, about 3:1 to about 1:20, about 2:1 to about 1:20, about 0:1 to about 1:20, about 1:1 to about 1:20, about 1:2 to about 1:20, about 1:3 to about 1:20, about 1:4 to about 1:20, about 1:5 to about 1:20, about 5:1 to about 1:15, about 4:1 to about 1:15, about 3:1 to about 1:15, about 0:1 to about 1:15, about 2:1 to about 1:15, about 1:1 to about 1:15, about 1:2 to about 1:15, about 1:3 to about 1:15, about 1:4 to about 1:15, about 1:5 to about 1:15, about 5:1 to about 1:12, about 4:1 to about 1:12, about 3:1 to about 1:12, about 2:1 to about 1:12, about 0:1 to about 1:12, about 1:1 to about 1:12, about 1:2 to about 1:12, about 1:3 to about 1:12, about 1:4 to about 1:12, about 1:5 to about 1:12, about 1:6 to about 1:12, about 1:7 to about 1:12, about 1:8 to about 1:12, about 5:1 to about 1:10, about 4:1 to about 1:10, about 3:1 to about 1:10, about 2:1 to about 1:10, about 0:1 to about 1:10, about 1:1 to about 1:10, about 1:2 to about 1:10, about 1:3 to about 1:10, about 1:4 to about 1:10, about 1:5 to about 1:10, about 1:6 to about 1:10, about 1:7 to about 1:10, or about 1:8 to about 1:10.

In an embodiment, a cancer therapeutic, including, without limitation, artemesinin and/or its derivatives is formulated in a one fat. In an embodiment, a cancer therapeutic, including, without limitation, artemesinin and/or its derivatives is formulated in two fats. In an embodiment, a cancer therapeutic, including, without limitation, artemesinin and/or its derivatives is formulated in three fats. In an embodiment, a cancer therapeutic, including, without limitation, artemesinin and/or its derivatives is formulated in four fats. In an embodiment, a cancer therapeutic, including, without limitation, artemesinin and/or its derivatives is formulated in five fats. In an embodiment, a cancer therapeutic, including, without limitation, artemesinin and/or its derivatives is formulated in six fats. In an embodiment, a cancer therapeutic, including, without limitation, artemesinin and/or its derivatives is formulated in seven or more fats.

In an embodiment, a cancer therapeutic, including, without limitation, artemesinin and/or its derivatives is formulated in a fat that is a liquid. In an embodiment, a cancer therapeutic, including, without limitation, artemesinin and/or its derivatives is formulated in at fat that is a solid. In an embodiment, a cancer therapeutic, including, without limitation, artemesinin and/or its derivatives is formulated in a two or more fats that are liquids. In an embodiment, a cancer therapeutic, including, without limitation, artemesinin and/or its derivatives is formulated in two or more fats that are solids. In an embodiment, a cancer therapeutic, including, without limitation, artemesinin and/or its derivatives is formulated in two or more fats, wherein at least one fat is a solid and at least one fat is a liquid.

Step (b) may be carried out at room temperature, in order to allow the solution comprising the therapeutic compound to form the pharmaceutical composition. However, in other embodiments of the method, Step (b) may be carried out at a temperature that is greater than room temperature. In aspects of this embodiment, Step (b) may be carried out at a temperature that is, e.g., greater than 21° C., greater than 25° C., greater than 30° C., greater than 35° C. or greater than 37° C., greater than 40° C., greater than 42° C., greater than 45° C., greater than 50° C., greater than 55° C., or greater than 60° C. In aspects of this embodiment, Step (a) may be carried out at a temperature that is between, e.g., about 20° C. to about 30° C., about 25° C. to about 35° C., about 30° C. to about 40° C., about 35° C. to about 45° C., about 40° C. to about 50° C., about 45° C. to about 55° C., or about 50° C. to about 60° C. In certain cases, Step (b) may be carried out at temperatures below room temperature, in order to allow a therapeutic compound to dissolve fully in a pharmaceutically-acceptable solvent. However, in other embodiments of the method, step (b) may be carried out at a temperature that is less than room temperature, e.g., less than 10° C., greater than 5° C., greater than 0° C., greater than −10° C. or greater than −20° C. The contacting in Step (b) may comprise mixing the solution and the pharmaceutically-acceptable adjuvant, e.g., by stirring, inversion, sonication, or vortexing. The mixing may be carried out for, e.g., at least 1 second, at least 5 seconds, at least 10 seconds, at least 20 seconds, at least 30 seconds, at least 45 seconds, at least 60 seconds, or more, until the pharmaceutical composition is formed.

In certain embodiments, a rapid cooling step may be used to reduce the temperature of a pharmaceutical composition disclosed herein after its formation. For example, a rapid cooling step may be used in procedures were temperatures greater than room temperature are used to allow a therapeutic compound to dissolve fully in the pharmaceutically-acceptable solvent and/or to allow the solution comprising the therapeutic compound to form the pharmaceutical composition. In aspects of this embodiment, a rapid cooling step results in a temperature decrease of, e.g., about 30° C. in 20 minutes, about 25° C. in 20 minutes, about 20° C. in 20 minutes, about 15° C. in 20 minutes, about 30° C. in 15 minutes, about 25° C. in 15 minutes, about 20° C. in 15 minutes, about 15° C. in 15 minutes, about 30° C. in 10 minutes, about 25° C. in 10 minutes, about 20° C. in 10 minutes, about 15° C. in 10 minutes, about 30° C. in 5 minutes, about 25° C. in 5 minutes, about 20° C. in 5 minutes, about 15° C. in 5 minutes. In other aspects of this embodiment, a rapid cooling step results in a temperature decrease of, e.g., about 20° C. to about 30° C. in 20 minutes, about 20° C. to about 30° C. in 15 minutes, about 20° C. to about 30° C. in 10 minutes, about 20° C. to about 30° C. in 5 minutes, about 15° C. to about 25° C. in 20 minutes, about 15° C. to about 25° C. in 15 minutes, about 15° C. to about 25° C. in 10 minutes, about 15° C. to about 25° C. in 5 minutes, about 10° C. to about 20° C. in 20 minutes, about 10° C. to about 20° C. in 15 minutes, about 10° C. to about 20° C. in 10 minutes, or about 10° C. to about 20° C. in 5 minutes.

In yet aspects of this embodiment, a rapid cooling step results in a temperature decrease of, e.g., about 2.0° C./minute, about 1.9° C./minute, about 1.8° C./minute, about 1.7° C./minute, about 1.6° C./minute, about 1.5° C./minute, about 1.4° C./minute, about 1.3° C./minute, about 1.2° C./minute, about 1.1° C./minute, about 1.0° C./minute, about 0.9° C./minute, about 0.8° C./minute, about 0.7° C./minute, about 0.6° C./minute, about 0.5° C./minute, about 0.4° C./minute, about 0.3° C./minute, about 0.2° C./minute, or about 0.1° C./minute. In still aspects of this embodiment, a rapid cooling step results in a temperature decrease of, e.g., about 0.1° C. to about 0.4° C./minute, about 0.2° C. to about 0.6° C./minute, about 0.4° C. to about 0.8° C./minute, about 0.6° C. to about 1.0° C./minute, about 0.8° C. to about 1.2° C./minute, about 1.0° C. to about 1.4° C./minute, about 1.2° C. to about 1.6° C./minute, about 1.4° C. to about 1.8° C./minute, about 1.6° C. to about 2.0° C./minute, about 0.1° C. to about 0.5° C./minute, about 0.5° C. to about 1.0° C./minute, about 1.0° C. to about 1.5° C./minute, about 1.5° C. to about 2.0° C./minute, about 0.5° C. to about 1.5° C./minute, or about 1.0° C. to about 2.0° C./minute.

In some embodiments, temperatures greater than room temperature employed in either Step (a) or Step (b) or both may be used to remove the solvent from a pharmaceutical composition. In other embodiment, removal of solvent from a pharmaceutical composition requires a separate Step (c). In Step (c), the solvent removal from a pharmaceutical composition may be accomplished using one of a variety of procedures known in the art, including, without limitation, evaporation, dialyzation, distillation, lypholization, and filtration. These removal procedures may be done under conditions of ambient atmosphere, under low pressure, or under a vacuum and either at ambient temperature or at temperatures requiring heating.

In one embodiment, Step (c) may result in the complete removal of a pharmaceutically-acceptable solvent from the pharmaceutical composition disclosed herein. In aspects of this embodiment, Step (c) may result in, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 93%, at least 95%, at least 97%, or at least 99% removal of a pharmaceutically-acceptable solvent from the pharmaceutical composition disclosed herein.

Step (c) is conducted at a temperature that allows for the evaporation of a pharmaceutically-acceptable solvent disclosed herein, and as such, an evaporation temperature is solvent dependant. Factors which influence an evaporation temperature of a solvent disclosed herein include, without limitation, the particular solvent used, the amount of solvent present, the particular therapeutic compound present, the particular adjuvant present, the stability of the therapeutic compound present, the reactivity of the therapeutic compound present, the particular atmospheric pressure used, the time desired for complete evaporation. Generally, a pharmaceutical composition will require heating if the evaporation step is conducted at ambient pressure, e.g., 1 atm. However, under high vacuum conditions, the evaporation step may be conducted at temperatures below ambient temperature, e.g., less than 22° C.

In one embodiment, removal of solvent from the pharmaceutical composition disclosed herein may be carried out at ambient atmospheric pressure and at a temperature above ambient temperature. In aspects of this embodiment, removal of solvent from the pharmaceutical composition disclosed herein may be carried out at ambient atmospheric pressure and at a temperature of, e.g., more than 25° C., more than 30° C., more than 35° C., more than 40° C., more than 45° C., more than 50° C., more than 55° C., more than 60° C., more than 65° C., more than 70° C., more than 80° C., or more than 25° C. In other aspects of this embodiment, removal of solvent from the pharmaceutical composition disclosed herein may be carried out at ambient atmospheric pressure and at a temperature in a range of, e.g., about 25° C. to about 100° C., about 25° C. to about 95° C., about 25° C. to about 90° C., about 25° C. to about 85° C., about 25° C. to about 80° C., about 25° C. to about 75° C., about 25° C. to about 70° C., about 25° C. to about 65° C., or about 25° C. to about 60° C.

In another embodiment, removal of solvent from the pharmaceutical composition disclosed herein may be carried out under vacuum and at a temperature below ambient temperature. In aspects of this embodiment, removal of solvent from the pharmaceutical composition disclosed herein may be carried out under vacuum and at a temperature of, e.g., less than 20° C., less than 18° C., less than 16° C., less than 14° C., less than 12° C., less than 10° C., less than 8° C., less than 6° C., less than 4° C., less than 2° C., or less than 0° C. In other aspects of this embodiment, removal of solvent from the pharmaceutical composition disclosed herein may be carried out under vacuum and at a temperature in a range of, e.g., about −20° C. to about 20° C., about −20° C. to about 18° C., about −20° C. to about 16° C., about −20° C. to about 14° C., about −20° C. to about 12° C., about −20° C. to about 10° C., about −20° C. to about 8° C., about −20° C. to about 6° C., about −20° C. to about 4° C., about −20° C. to about 2° C., about −20° C. to about 0° C., about −15° C. to about 20° C., about −10° C. to about 20° C., about −5° C. to about 20° C., about 0° C. to about 20° C., about −10° C. to about 20° C., about −10° C. to about 18° C., about −10° C. to about 16° C., about −10° C. to about 14° C., about −10° C. to about 12° C., about −10° C. to about 10° C., about −10° C. to about 8° C., about −10° C. to about 6° C., about −10° C. to about 4° C., about −10° C. to about 2° C., or about −10° C. to about 0° C.

The final concentration of a therapeutic compound disclosed herein in a pharmaceutical composition disclosed herein may be of any concentration desired. In an aspect of this embodiment, the final concentration of a therapeutic compound in a pharmaceutical composition may be a therapeutically effective amount. In other aspects of this embodiment, the final concentration of a therapeutic compound in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the final concentration of a therapeutic compound in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

A pharmaceutical composition produced using the methods disclosed herein may be formulated for either local or systemic delivery using topical, enteral or parenteral routes of administration. Additionally, a therapeutic compound disclosed herein may be formulated by itself in a pharmaceutical composition, or may be formulated together with one or more other therapeutic compounds disclosed herein in a single pharmaceutical composition.

A pharmaceutical composition produced using the methods disclosed herein may be a liquid formulation, semi-solid formulation, or a solid formulation. A formulation disclosed herein can be produced in a manner to form one phase, such as, e.g., an oil or a solid. Alternatively, a formulation disclosed herein can be produced in a manner to form two phase, such as, e.g., an emulsion. A pharmaceutical composition disclosed herein intended for such administration may be prepared according to any method known to the art for the manufacture of pharmaceutical compositions. Semi-solid formulations suitable for topical administration include, without limitation, ointments, creams, salves, and gels.

A liquid formulation may be formed by using various lipids like oils of other fatty acids that remain as liquids in the temperature range desired. In an embodiment, a pharmaceutical composition disclosed herein is liquid at room temperature. In aspects of this embodiment, a pharmaceutical composition disclosed herein may be formulated to be a liquid at a temperature of, e.g., about 25° C. or higher, about 23° C. or higher, about 21° C. or higher, about 19° C. or higher, about 17° C. or higher, about 15° C. or higher, about 12° C. or higher, about 10° C. or higher, about 8° C. or higher, about 6° C. or higher, about 4° C. or higher, or about 0° C. or higher.

In liquid and semi-solid formulations, a concentration of a therapeutic compound disclosed herein typically may be between about 50 mg/mL to about 1,000 mg/mL. In aspects of this embodiment, a therapeutically effective amount of a therapeutic compound disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

In semi-solid and solid formulations, an amount of a therapeutic compound disclosed herein typically may be between about 0.01% to about 45% by weight. In aspects of this embodiment, an amount of a therapeutic compound disclosed herein may be from, e.g., about 0.1% to about 45% by weight, about 0.1% to about 40% by weight, about 0.1% to about 35% by weight, about 0.1% to about 30% by weight, about 0.1% to about 25% by weight, about 0.1% to about 20% by weight, about 0.1% to about 15% by weight, about 0.1% to about 10% by weight, about 0.1% to about 5% by weight, about 1% to about 45% by weight, about 1% to about 40% by weight, about 1% to about 35% by weight, about 1% to about 30% by weight, about 1% to about 25% by weight, about 1% to about 20% by weight, about 1% to about 15% by weight, about 1% to about 10% by weight, about 1% to about 5% by weight, about 5% to about 45% by weight, about 5% to about 40% by weight, about 5% to about 35% by weight, about 5% to about 30% by weight, about 5% to about 25% by weight, about 5% to about 20% by weight, about 5% to about 15% by weight, about 5% to about 10% by weight, about 10% to about 45% by weight, about 10% to about 40% by weight, about 10% to about 35% by weight, about 10% to about 30% by weight, about 10% to about 25% by weight, about 10% to about 20% by weight, about 10% to about 15% by weight, about 15% to about 45% by weight, about 15% to about 40% by weight, about 15% to about 35% by weight, about 15% to about 30% by weight, about 15% to about 25% by weight, about 15% to about 20% by weight, about 20% to about 45% by weight, about 20% to about 40% by weight, about 20% to about 35% by weight, about 20% to about 30% by weight, about 20% to about 25% by weight, about 25% to about 45% by weight, about 25% to about 40% by weight, about 25% to about 35% by weight, or about 25% to about 30% by weight.

In another embodiment, a solid formulation comprises a cancer therapeutic, including, but not limited to, artemesinin or a derivative thereof, a mixture of mono-, di-, and triglycerides and PEG fatty acid esters, a glyceryl monolinoleate, and a polyethylene glycol. In an aspect of this embodiment, a solid formulation comprises about 1% to about 30% by weight of a cancer therapeutic, including, but not limited to, artemesinin or a derivative thereof, about 8% to about 70% by weight of a mixture of mono-, di-, and triglycerides and PEG fatty acid esters, about 2% to about 65% by weight of a glyceryl monolinoleate, and about 1% to about 15% of polyethylene glycol. In another aspect of this embodiment, a solid formulation comprises about 10% to about 30% by weight of a cancer therapeutic, including, but not limited to, artemesinin or a derivative thereof, about 20% to about 50% by weight of a mixture of mono-, di-, and triglycerides and PEG fatty acid esters, about 10% to about 30% by weight of a glyceryl monolinoleate, and about 5% to about 15% of polyethylene glycol. In yet another aspect of this embodiment, a solid formulation comprises about 20% to about 30% by weight of a cancer therapeutic, including, but not limited to, artemesinin or a derivative thereof, about 30% to about 50% by weight of a mixture of mono-, di-, and triglycerides and PEG fatty acid esters, about 10% to about 30% by weight of a glyceryl monolinoleate, and about 7% to about 13% of polyethylene glycol. In still another aspect of this embodiment, a solid formulation comprises about 20% to about 30% by weight of a cancer therapeutic, including, but not limited to, artemesinin or a derivative thereof, about 35% to about 50% by weight of a mixture of mono-, di-, and triglycerides and PEG fatty acid esters, about 15% to about 25% by weight of a glyceryl monolinoleate, and about 7% to about 13% of polyethylene glycol. In a further aspect of this embodiment, a solid formulation comprises about 23% to about 27% by weight of a cancer therapeutic, including, but not limited to, artemesinin or a derivative thereof, about 41% to about 47% by weight of a mixture of mono-, di-, and triglycerides and PEG fatty acid esters, about 18% to about 22% by weight of a glyceryl monolinoleate, and about 9% to about 11% of polyethylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a solid formulation comprises a therapeutic compound, a hard fat, a partially-hydrogenated fat, a polyethylene glycol, and a propylene glycol. In an aspect of this embodiment, a solid formulation comprises about 1% to about 30% by weight of therapeutic compound, about 8% to about 70% by weight of hard fat, about 2% to about 65% by weight of partially-hydrogenated fat, about 1% to about 15% of polyethylene glycol, and about 1% to about 15% of propylene glycol. In another aspect of this embodiment, a solid formulation comprises about 10% to about 30% by weight of therapeutic compound, about 20% to about 50% by weight of hard fat, about 10% to about 30% by weight of partially-hydrogenated fat, about 5% to about 15% of polyethylene glycol, and about 5% to about 15% of propylene glycol. In yet another aspect of this embodiment, a solid formulation comprises about 20% to about 30% by weight of therapeutic compound, about 30% to about 50% by weight of hard fat, about 10% to about 30% by weight of partially-hydrogenated fat, about 7% to about 13% of polyethylene glycol, and about 7% to about 13% of propylene glycol. In still another aspect of this embodiment, a solid formulation comprises about 20% to about 30% by weight of therapeutic compound, about 35% to about 50% by weight of hard fat, about 15% to about 25% by weight of partially-hydrogenated fat, about 7% to about 13% of polyethylene glycol, and about 7% to about 13% of propylene glycol. In a further aspect of this embodiment, a solid formulation comprises about 23% to about 27% by weight of therapeutic compound, about 41% to about 47% by weight of hard fat, about 18% to about 22% by weight of partially-hydrogenated fat, about 9% to about 11% of polyethylene glycol, and about 9% to about 11% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a solid formulation comprises a therapeutic compound, a mixture of mono-, di-, and triglycerides and PEG fatty acid esters, a glyceryl monolinoleate, a polyethylene glycol, and a propylene glycol. In an aspect of this embodiment, a solid formulation comprises about 1% to about 30% by weight of therapeutic compound, about 8% to about 70% by weight of a mixture of mono-, di-, and triglycerides and PEG fatty acid esters, about 2% to about 65% by weight of a glyceryl monolinoleate, about 1% to about 15% of polyethylene glycol, and about 1% to about 15% of propylene glycol. In another aspect of this embodiment, a solid formulation comprises about 10% to about 30% by weight of therapeutic compound, about 20% to about 50% by weight of a mixture of mono-, di-, and triglycerides and PEG fatty acid esters, about 10% to about 30% by weight of a glyceryl monolinoleate, about 5% to about 15% of polyethylene glycol, and about 5% to about 15% of propylene glycol. In yet another aspect of this embodiment, a solid formulation comprises about 20% to about 30% by weight of therapeutic compound, about 30% to about 50% by weight of a mixture of mono-, di-, and triglycerides and PEG fatty acid esters, about 10% to about 30% by weight of a glyceryl monolinoleate, and about 7% to about 13% of polyethylene glycol, and about 7% to about 13% of propylene glycol. In still another aspect of this embodiment, a solid formulation comprises about 20% to about 30% by weight of therapeutic compound, about 35% to about 50% by weight of a mixture of mono-, di-, and triglycerides and PEG fatty acid esters, about 15% to about 25% by weight of a glyceryl monolinoleate, about 7% to about 13% of polyethylene glycol, and about 7% to about 13% of propylene glycol. In a further aspect of this embodiment, a solid formulation comprises about 23% to about 27% by weight of therapeutic compound, about 41% to about 47% by weight of a mixture of mono-, di-, and triglycerides and PEG fatty acid esters, about 18% to about 22% by weight of a glyceryl monolinoleate, about 9% to about 11% of polyethylene glycol, and about 9% to about 11% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a solid formulation comprises a cancer therapeutic, including, but not limited to, artemesinin or a derivative thereof, a mixture of mono-, di-, and triglycerides and PEG fatty acid esters, a glyceryl monolinoleate, a polyethylene glycol, and a propylene glycol. In an aspect of this embodiment, a solid formulation comprises about 1% to about 30% by weight of a cancer therapeutic, including, but not limited to, artemesinin or a derivative thereof, about 8% to about 70% by weight of a mixture of mono-, di-, and triglycerides and PEG fatty acid esters, about 2% to about 65% by weight of a glyceryl monolinoleate, about 1% to about 15% of polyethylene glycol, and about 1% to about 15% of propylene glycol. In another aspect of this embodiment, a solid formulation comprises about 10% to about 30% by weight of a cancer therapeutic, including, but not limited to, artemesinin or a derivative thereof, about 20% to about 50% by weight of a mixture of mono-, di-, and triglycerides and PEG fatty acid esters, about 10% to about 30% by weight of a glyceryl monolinoleate, about 5% to about 15% of polyethylene glycol, and about 5% to about 15% of propylene glycol. In yet another aspect of this embodiment, a solid formulation comprises about 20% to about 30% by weight of a cancer therapeutic, including, but not limited to, artemesinin or a derivative thereof, about 30% to about 50% by weight of a mixture of mono-, di-, and triglycerides and PEG fatty acid esters, about 10% to about 30% by weight of a glyceryl monolinoleate, and about 7% to about 13% of polyethylene glycol, and about 7% to about 13% of propylene glycol. In still another aspect of this embodiment, a solid formulation comprises about 20% to about 30% by weight of a cancer therapeutic, including, but not limited to, artemesinin or a derivative thereof, about 35% to about 50% by weight of a mixture of mono-, di-, and triglycerides and PEG fatty acid esters, about 15% to about 25% by weight of a glyceryl monolinoleate, about 7% to about 13% of polyethylene glycol, and about 7% to about 13% of propylene glycol. In a further aspect of this embodiment, a solid formulation comprises about 23% to about 27% by weight of a cancer therapeutic, including, but not limited to, artemesinin or a derivative thereof, about 41% to about 47% by weight of a mixture of mono-, di-, and triglycerides and PEG fatty acid esters, about 18% to about 22% by weight of a glyceryl monolinoleate, about 9% to about 11% of polyethylene glycol, and about 9% to about 11% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a semi-solid formulation comprises a therapeutic compound, a hard fat, a partially-hydrogenated fat, a polyethylene glycol, and a propylene glycol. In an aspect of this embodiment, a semi-solid formulation comprises about 15% to about 55% by weight of therapeutic compound, about 7% to about 20% by weight of hard fat, about 20% to about 50% by weight of partially-hydrogenated fat, about 7% to about 20% of polyethylene glycol, and about 1% to about 8% of propylene glycol. In another aspect of this embodiment, a semi-solid formulation comprises about 20% to about 50% by weight of therapeutic compound, about 8% to about 18% by weight of hard fat, about 25% to about 45% by weight of partially-hydrogenated fat, about 8% to about 18% of polyethylene glycol, and about 2% to about 6% of propylene glycol. In another aspect of this embodiment, a semi-solid formulation comprises about 20% to about 50% by weight of therapeutic compound, about 10% to about 16% by weight of hard fat, about 25% to about 45% by weight of partially-hydrogenated fat, about 10% to about 16% of polyethylene glycol, and about 2% to about 6% of propylene glycol. In yet another aspect of this embodiment, a semi-solid formulation comprises about 20% to about 50% by weight of therapeutic compound, about 11% to about 15% by weight of hard fat, about 30% to about 40% by weight of partially-hydrogenated fat, about 11% to about 15% of polyethylene glycol, and about 3% to about 5% of propylene glycol. In still another aspect of this embodiment, a semi-solid formulation comprises about 25% to about 44% by weight of therapeutic compound, about 12% to about 14% by weight of hard fat, about 32% to about 39% by weight of partially-hydrogenated fat, about 12% to about 14% of polyethylene glycol, and about 4% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a semi-solid formulation comprises a therapeutic compound, a mixture of mono-, di-, and triglycerides and PEG fatty acid esters, a glyceryl monolinoleate, a polyethylene glycol, and a propylene glycol. In an aspect of this embodiment, a semi-solid formulation comprises about 15% to about 55% by weight of therapeutic compound, about 7% to about 20% by weight of a mixture of mono-, di-, and triglycerides and PEG fatty acid esters, about 20% to about 50% by weight of a glyceryl monolinoleate, about 7% to about 20% of polyethylene glycol, and about 1% to about 8% of propylene glycol. In another aspect of this embodiment, a semi-solid formulation comprises about 20% to about 50% by weight of therapeutic compound, about 8% to about 18% by weight of a mixture of mono-, di-, and triglycerides and PEG fatty acid esters, about 25% to about 45% by weight of a glyceryl monolinoleate, about 8% to about 18% of polyethylene glycol, and about 2% to about 6% of propylene glycol. In another aspect of this embodiment, a semi-solid formulation comprises about 20% to about 50% by weight of therapeutic compound, about 10% to about 16% by weight of a mixture of mono-, di-, and triglycerides and PEG fatty acid esters, about 25% to about 45% by weight of a glyceryl monolinoleate, about 10% to about 16% of polyethylene glycol, and about 2% to about 6% of propylene glycol. In yet another aspect of this embodiment, a semi-solid formulation comprises about 20% to about 50% by weight of therapeutic compound, about 11% to about 15% by weight of a mixture of mono-, di-, and triglycerides and PEG fatty acid esters, about 30% to about 40% by weight of a glyceryl monolinoleate, and about 11% to about 15% of polyethylene glycol, and about 3% to about 5% of propylene glycol. In still another aspect of this embodiment, a semi-solid formulation comprises about 25% to about 44% by weight of therapeutic compound, about 12% to about 14% by weight of a mixture of mono-, di-, and triglycerides and PEG fatty acid esters, about 32% to about 39% by weight of a glyceryl monolinoleate, about 12% to about 14% of polyethylene glycol, and about 4% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a semi-solid formulation comprises an ibuprofen, a mixture of mono-, di-, and triglycerides and PEG fatty acid esters, a glyceryl monolinoleate, a polyethylene glycol, and a propylene glycol. In an aspect of this embodiment, a semi-solid formulation comprises about 15% to about 55% by weight of an ibuprofen, about 7% to about 20% by weight of a mixture of mono-, di-, and triglycerides and PEG fatty acid esters, about 20% to about 50% by weight of a glyceryl monolinoleate, about 7% to about 20% of polyethylene glycol, and about 1% to about 8% of propylene glycol. In another aspect of this embodiment, a semi-solid formulation comprises about 20% to about 50% by weight of an ibuprofen, about 8% to about 18% by weight of a mixture of mono-, di-, and triglycerides and PEG fatty acid esters, about 25% to about 45% by weight of a glyceryl monolinoleate, about 8% to about 18% of polyethylene glycol, and about 2% to about 6% of propylene glycol. In another aspect of this embodiment, a semi-solid formulation comprises about 20% to about 50% by weight of an ibuprofen, about 10% to about 16% by weight of a mixture of mono-, di-, and triglycerides and PEG fatty acid esters, about 25% to about 45% by weight of a glyceryl monolinoleate, about 10% to about 16% of polyethylene glycol, and about 2% to about 6% of propylene glycol. In yet another aspect of this embodiment, a semi-solid formulation comprises about 20% to about 50% by weight of an ibuprofen, about 11% to about 15% by weight of a mixture of mono-, di-, and triglycerides and PEG fatty acid esters, about 30% to about 40% by weight of a glyceryl monolinoleate, and about 11% to about 15% of polyethylene glycol, and about 3% to about 5% of propylene glycol. In still another aspect of this embodiment, a semi-solid formulation comprises about 25% to about 44% by weight of an ibuprofen, about 12% to about 14% by weight of a mixture of mono-, di-, and triglycerides and PEG fatty acid esters, about 32% to about 39% by weight of a glyceryl monolinoleate, about 12% to about 14% of polyethylene glycol, and about 4% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a semi-solid formulation comprises a therapeutic compound, a hard fat, a partially-hydrogenated fat, a polyethylene glycol, and a propylene glycol. In an aspect of this embodiment, a semi-solid formulation comprises about 10% to about 35% by weight of a free acid of a therapeutic compound, about 1% to about 30% by weight of a salt of a therapeutic compound, about 7% to about 20% by weight of hard fat, about 20% to about 50% by weight of partially-hydrogenated fat, about 7% to about 20% of polyethylene glycol, and about 1% to about 8% of propylene glycol. In another aspect of this embodiment, a semi-solid formulation comprises about 15% to about 30% by weight of a free acid of a therapeutic compound, about 1% to about 25% by weight of a salt of a therapeutic compound, about 10% to about 16% by weight of hard fat, about 25% to about 45% by weight of partially-hydrogenated fat, about 10% to about 16% of polyethylene glycol, and about 2% to about 6% of propylene glycol. In yet another aspect of this embodiment, a semi-solid formulation comprises about 15% to about 30% by weight of a free acid of a therapeutic compound, about 1% to about 25% by weight of a salt of a therapeutic compound, about 11% to about 15% by weight of hard fat, about 30% to about 40% by weight of partially-hydrogenated fat, about 11% to about 15% of polyethylene glycol, and about 3% to about 5% of propylene glycol. In still another aspect of this embodiment, a semi-solid formulation comprises about 20% to about 24% by weight of a free acid of a therapeutic compound, about 5% to about 20% by weight of a salt of a therapeutic compound, about 12% to about 14% by weight of hard fat, about 32% to about 39% by weight of partially-hydrogenated fat, about 12% to about 14% of polyethylene glycol, and about 4% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a semi-solid formulation comprises a therapeutic compound, a mixture of mono-, di-, and triglycerides and PEG fatty acid esters, a glyceryl monolinoleate, a polyethylene glycol, and a propylene glycol. In an aspect of this embodiment, a semi-solid formulation comprises about 10% to about 35% by weight of a free acid of a therapeutic compound, about 1% to about 30% by weight of a salt of a therapeutic compound, about 7% to about 20% by weight of a mixture of mono-, di-, and triglycerides and PEG fatty acid esters, about 20% to about 50% by weight of a glyceryl monolinoleate, about 7% to about 20% of polyethylene glycol, and about 1% to about 8% of propylene glycol. In another aspect of this embodiment, a semi-solid formulation comprises about 15% to about 30% by weight of a free acid of a therapeutic compound, about 1% to about 25% by weight of a salt of a therapeutic compound, about 10% to about 16% by weight of a mixture of mono-, di-, and triglycerides and PEG fatty acid esters, about 25% to about 45% by weight of a glyceryl monolinoleate, about 10% to about 16% of polyethylene glycol, and about 2% to about 6% of propylene glycol. In yet another aspect of this embodiment, a semi-solid formulation comprises about 15% to about 30% by weight of a free acid of a therapeutic compound, about 1% to about 25% by weight of a salt of a therapeutic compound, about 11% to about 15% by weight of a mixture of mono-, di-, and triglycerides and PEG fatty acid esters, about 30% to about 40% by weight of a glyceryl monolinoleate, and about 11% to about 15% of polyethylene glycol, and about 3% to about 5% of propylene glycol. In still another aspect of this embodiment, a semi-solid formulation comprises about 20% to about 24% by weight of a free acid of a therapeutic compound, about 5% to about 20% by weight of a salt of a therapeutic compound, about 12% to about 14% by weight of a mixture of mono-, di-, and triglycerides and PEG fatty acid esters, about 32% to about 39% by weight of a glyceryl monolinoleate, about 12% to about 14% of polyethylene glycol, and about 4% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a semi-solid formulation comprises a cancer therapeutic, including, but not limited to, artemesinin or a derivative thereof, a mixture of mono-, di-, and triglycerides and PEG fatty acid esters, a glyceryl monolinoleate, a polyethylene glycol, and a propylene glycol. In an aspect of this embodiment, a semi-solid formulation comprises about 10% to about 35% by weight of a free acid of an ibuprofen, about 1% to about 30% by weight of a salt of a cancer therapeutic, including, but not limited to, artemesinin or a derivative thereof, about 7% to about 20% by weight of a mixture of mono-, di-, and triglycerides and PEG fatty acid esters, about 20% to about 50% by weight of a glyceryl monolinoleate, about 7% to about 20% of polyethylene glycol, and about 1% to about 8% of propylene glycol. In another aspect of this embodiment, a semi-solid formulation comprises about 15% to about 30% by weight of a free acid of a cancer therapeutic, including, but not limited to, artemesinin or a derivative thereof, about 1% to about 25% by weight of a salt of a cancer therapeutic, including, but not limited to, artemesinin or a derivative thereof, about 10% to about 16% by weight of a mixture of mono-, di-, and triglycerides and PEG fatty acid esters, about 25% to about 45% by weight of a glyceryl monolinoleate, about 10% to about 16% of polyethylene glycol, and about 2% to about 6% of propylene glycol. In yet another aspect of this embodiment, a semi-solid formulation comprises about 15% to about 30% by weight of a free acid of a cancer therapeutic, including, but not limited to, artemesinin or a derivative thereof, about 1% to about 25% by weight of a salt of an ibuprofen, about 11% to about 15% by weight of a mixture of mono-, di-, and triglycerides and PEG fatty acid esters, about 30% to about 40% by weight of a glyceryl monolinoleate, and about 11% to about 15% of polyethylene glycol, and about 3% to about 5% of propylene glycol. In still another aspect of this embodiment, a semi-solid formulation comprises about 20% to about 24% by weight of a free acid of a cancer therapeutic, including, but not limited to, artemesinin or a derivative thereof, about 5% to about 20% by weight of a salt of a cancer therapeutic, including, but not limited to, artemesinin or a derivative thereof, about 12% to about 14% by weight of a mixture of mono-, di-, and triglycerides and PEG fatty acid esters, about 32% to about 39% by weight of a glyceryl monolinoleate, about 12% to about 14% of polyethylene glycol, and about 4% of propylene glycol. In other aspects of this embodiment, a polyethylene glycol is, e.g., a PEG 100, a PEG 200, a PEG 300, a PEG 400, a PEG 500, a PEG 600, or a PEG 700.

A solid or semi-solid formulation disclosed herein takes advantage of the different melting point temperatures of the various adjuvants like fatty acids. Formation of a solid or semi-solid dosage form can be by modifying the respective concentrations of the fatty acids comprising a pharmaceutical composition disclosed herein. For example, linolenic acid has a melting point temperature ($T_m$) of about −11° C., linoleic acid has a $T_m$ of about −5° C., oleic acid has a $T_m$ of about 16° C., palmitic acid has a $T_m$ of about 61-62° C., and Stearic acid has a $T_m$ of about 67-72° C. Increasing the proportion(s) of palmitic, stearic or oleic acid would increase the overall melting temperature of a composition, while, conversely, increasing the proportion(s) of linoleic and linolenic acid would decrease the melting temperature of a composition. Thus, by controlling the types and amounts of the adjuvant components added, a pharmaceutical composition disclosed herein can be made that is substantially solid or semi-solid at room temperature, but melts when it is ingested, and reaches body temperature. The resulting melted composition readily forms micelles which are absorbed by the intestine, assembled into chylomicrons, and ultimately absorbed by macrophages. The solid dosage form may be a powder, granule, tablet, capsule or suppository.

In an embodiment, a pharmaceutical composition disclosed herein is solid at room temperature. In aspects of this embodiment, a pharmaceutical composition disclosed herein may be formulated to be a solid at a temperature of, e.g., about 35° C. or lower, about 33° C. or lower, about 31° C. or lower, about 29° C. or lower, about 27° C. or lower, about 25° C. or lower, about 23° C. or lower, about 21° C. or lower, about 19° C. or lower, about 17° C. or lower, about 15° C. or lower, about 12° C. or lower, about 10° C. or lower, about 8° C. or lower, about 6° C. or lower, about 4° C. or lower, or about 0° C. or lower.

In other aspects of this embodiment, a pharmaceutical composition disclosed has a melting point temperature of, e.g., 5° C. or higher, 10° C. or higher, 15° C. or higher, 22° C. or higher, 23° C. or higher, 24° C. or higher, 25° C. or higher, 26° C. or higher, 27° C. or higher, 28° C. or higher, 29° C. or higher, 30° C. or higher, 31° C. or higher, 32° C. or higher, 33° C. or higher, 34° C. or higher, or 35° C. or higher. In other aspects of this embodiment, a pharmaceutical composition disclosed has a melting point temperature in the range of, e.g., about 5° C. to about 24° C., about 10° C. to about 24° C. about 22° C. to about 24° C., about 23° C. to about 25° C., about 24° C. to about 26° C., about 25° C. to about 27° C., about 26° C. to about 28° C., about 27° C. to about 29° C., about 28° C. to about 30° C., about 29° C. to about 31° C., about 30° C. to about 32° C., about 31° C. to about 33° C., about 32° C. to about 34° C., or about 33° C. to about 35° C. In other aspects of this embodiment, a pharmaceutical composition disclosed has a melting point temperature in the range of, e.g., about 22° C. to about 26° C., about 24° C. to about 28° C., about 26° C. to about 30° C., about 28° C. to about 32° C., or about 30° C. to about 34° C.

In one embodiment, a liquid formulation comprises a therapeutic compound, a glycol ether, a partially-hydrogenated fat, an oil, and an alcohol. In an aspect of this embodiment, a liquid formulation comprises about 15% to about 35% by weight of therapeutic compound, about 5% to about 25% by weight of glycol ether, about 15% to about 40% by weight of partially-hydrogenated fat, about 15% to about 40% of an oil, and about 1% to about 15% of an alcohol. In another aspect of this embodiment, a liquid formulation comprises about 20% to about 30% by weight of therapeutic compound, about 10% to about 20% by weight of glycol ether, about 20% to about 35% by weight of partially-hydrogenated fat, about 20% to about 35% of an oil, and about 2% to about 10% of an alcohol. In yet another aspect of this embodiment, a liquid formulation comprises about 23% to about 27% by weight of therapeutic compound, about 13% to about 17% by weight of glycol ether, about 25% to about 30% by weight of partially-hydrogenated fat, about 25% to about 30% of an oil, and about 4% to about 8% of an alcohol. In still another aspect of this embodiment, a liquid formulation comprises about 24% to about 26% by weight of therapeutic compound, about 14% to about 16% by weight of glycol ether, about 26% to about 28% by weight of partially-hydrogenated fat, about 26% to about 28% of an oil, and about 5% to about 7% of an alcohol. In other aspects of this embodiment, an oil is rapeseed oil or *theobroma* oil.

In another embodiment, a liquid formulation comprises a therapeutic compound, a glycol ether, a glyceryl monolinoleate, an oil, and an alcohol. In an aspect of this embodiment, a liquid formulation comprises about 15% to about 35% by weight of therapeutic compound, about 5% to about 25% by weight of glycol ether, about 15% to about 40% by weight of glyceryl monolinoleate, about 15% to about 40% of an oil, and about 1% to about 15% of an alcohol. In another aspect of this embodiment, a liquid formulation comprises about 20% to about 30% by weight of therapeutic compound, about 10% to about 20% by weight of glycol ether, about 20% to about 35% by weight of glyceryl monolinoleate, about 20% to about 35% of an oil, and about 2% to about 10% of an alcohol. In yet another aspect of this embodiment, a liquid formulation comprises about 23% to about 27% by weight of therapeutic compound, about 13% to about 17% by weight of glycol ether, about 25% to about 30% by weight of glyceryl monolinoleate, about 25% to about 30% of an oil, and about 4% to about 8% of an alcohol. In still another aspect of this embodiment, a liquid formulation comprises about 24% to about 26% by weight of therapeutic compound, about 14% to about 16% by weight of glycol ether, about 26% to about 28% by weight of glyceryl monolinoleate, about 26% to about 28% of an oil, and about 5% to about 7% of an alcohol. In other aspects of this embodiment, an oil is rapeseed oil or *theobroma* oil.

In another embodiment, a liquid formulation comprises an ibuprofen, a diethylene glycol monoethyl ether, a glyceryl monolinoleate, an oil, and an alcohol. In an aspect of this embodiment, a liquid formulation comprises about 15% to about 35% by weight of an ibuprofen, about 5% to about 25% by weight of diethylene glycol monoethyl ether, about 15% to about 40% by weight of glyceryl monolinoleate, about 15% to about 40% of an oil, and about 1% to about 15% of an alcohol. In another aspect of this embodiment, a liquid formulation comprises about 20% to about 30% by weight of an ibuprofen, about 10% to about 20% by weight of diethylene glycol monoethyl ether, about 20% to about 35% by weight of glyceryl monolinoleate, about 20% to about 35% of an oil, and about 2% to about 10% of an alcohol. In yet another aspect of this embodiment, a liquid formulation comprises about 23% to about 27% by weight of an ibuprofen, about 13% to about 17% by weight of diethylene glycol monoethyl ether, about 25% to about 30% by weight of glyceryl monolinoleate, about 25% to about 30% of an oil, and about 4% to about 8% of an alcohol. In still another aspect of this embodiment, a liquid formulation comprises about 24% to about 26% by weight of an ibuprofen, about 14% to about 16% by weight of diethylene glycol monoethyl ether, about 26% to about 28% by weight of glyceryl monolinoleate, about 26% to about 28% of an oil, and about 5% to about 7% of an alcohol. In other aspects of this embodiment, an ibuprofen may be a free acid of a salt of ibuprofen. In other aspects of this embodiment, an oil is rapeseed oil or *theobroma* oil.

In one embodiment, a liquid formulation comprises a therapeutic compound, an ester of an alcohol, and an oil. In an aspect of this embodiment, a liquid formulation comprises about 1% to about 10% by weight of therapeutic compound, about 1% to about 10% by weight of an ester of an alcohol, and about 80% to about 98% of an oil. In another aspect of this embodiment, a liquid formulation comprises about 2% to about 8% by weight of therapeutic compound, about 1% to about 7% by weight of an ester of an alcohol, and about 85% to about 97% of an oil. In yet another aspect of this embodiment, a liquid formulation comprises about 3% to about 7% by weight of therapeutic compound, about 2% to about 6% by weight of an ester of an alcohol, and about 87% to about 95% of an oil. In still another aspect of this embodiment, a liquid formulation comprises about 4% to about 6% by weight of therapeutic compound, about 3% to about 5% by weight of an ester of an alcohol, and about 90% to about 92% of an oil. In other aspects of this embodiment, an oil is rapeseed oil or *theobroma* oil.

In another embodiment, a liquid formulation comprises a therapeutic compound, an ethyl acetate, and an oil. In an aspect of this embodiment, a liquid formulation comprises about 1% to about 10% by weight of therapeutic compound, about 1% to about 10% by weight of an ethyl acetate, and about 80% to about 98% of an oil. In another aspect of this embodiment, a liquid formulation comprises about 2% to about 8% by weight of therapeutic compound, about 1% to about 7% by weight of an ethyl acetate, and about 85% to about 97% of an oil. In yet another aspect of this embodiment, a liquid formulation comprises about 3% to about 7% by weight of therapeutic compound, about 2% to about 6% by weight of an ethyl acetate, and about 87% to about 95% of an oil. In still another aspect of this embodiment, a liquid formulation comprises about 4% to about 6% by weight of therapeutic compound, about 3% to about 5% by weight of an ethyl acetate, and about 90% to about 92% of an oil. In other aspects of this embodiment, an oil is rapeseed oil or *theobroma* oil.

In another embodiment, a liquid formulation comprises an ibuprofen, an ethyl acetate, and an oil. In an aspect of this embodiment, a liquid formulation comprises about 1% to about 10% by weight of an ibuprofen, about 1% to about 10% by weight of an ethyl acetate, and about 80% to about 98% of an oil. In another aspect of this embodiment, a liquid formulation comprises about 2% to about 8% by weight of an ibuprofen, about 1% to about 7% by weight of an ethyl acetate, and about 85% to about 97% of an oil. In yet another aspect of this embodiment, a liquid formulation comprises about 3% to about 7% by weight of an ibuprofen, about 2% to about 6% by weight of an ethyl acetate, and about 87% to about 95% of an oil. In still another aspect of this embodiment, a liquid formulation comprises about 4% to about 6% by weight of an ibuprofen, about 3% to about 5% by weight of an ethyl acetate, and about 90% to about 92% of an oil. In other aspects of this embodiment, an ibuprofen may be a free acid of a salt of ibuprofen. In other aspects of this embodiment, an oil is rapeseed oil or *theobroma* oil.

In one embodiment, a solid or semi-solid formulation disclosed herein is formulated without a hydrophilic solvent like water. Such formulations result in the formation of co-crystals of the lipids and therapeutic compound. Stated another way, such formulations do not form liposomal emulsions and/or micellular particles, which require hydrophilic solvent.

In one embodiment, a solid formulation comprises a therapeutic compound, a hard fat, a partially-hydrogenated fat, and a polyethylene glycol. In an aspect of this embodiment, a solid formulation comprises about 1% to about 30% by weight of therapeutic compound, about 8% to about 70% by weight of hard fat, about 2% to about 65% by weight of partially-hydrogenated fat, and about 1% to about 15% of polyethylene glycol. In another aspect of this embodiment, a solid formulation comprises about 10% to about 30% by weight of therapeutic compound, about 20% to about 50% by weight of hard fat, about 10% to about 30% by weight of partially-hydrogenated fat, and about 5% to about 15% of polyethylene glycol. In yet another aspect of this embodiment, a solid formulation comprises about 20% to about 30% by weight of therapeutic compound, about 30% to about 50% by weight of hard fat, about 10% to about 30% by weight of partially-hydrogenated fat, and about 7% to about 13% of polyethylene glycol. In still another aspect of this embodiment, a solid formulation comprises about 20% to about 30% by weight of therapeutic compound, about 35% to about 50% by weight of hard fat, about 15% to about 25% by weight of partially-hydrogenated fat, and about 7% to about 13% of polyethylene glycol. In a further aspect of this embodiment, a solid formulation comprises about 23% to about 27% by weight of therapeutic compound, about 41% to about 47% by weight of hard fat, about 18% to about 22% by weight of partially-hydrogenated fat, and about 9% to about 11% of polyethylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a solid formulation comprises a therapeutic compound, a mixture of mono-, di-, and triglycerides and PEG fatty acid esters, a glyceryl monolinoleate, and a polyethylene glycol. In an aspect of this embodiment, a solid formulation comprises about 1% to about 30% by weight of therapeutic compound, about 8% to about 70% by weight of a mixture of mono-, di-, and triglycerides and PEG fatty acid esters, about 2% to about 65% by weight of a glyceryl monolinoleate, and about 1% to about 15% of polyethylene glycol. In another aspect of this embodiment, a solid formulation comprises about 10% to about 30% by weight of therapeutic compound, about 20% to about 50% by weight of a mixture of mono-, di-, and triglycerides and PEG fatty acid esters, about 10% to about 30% by weight of a glyceryl monolinoleate, and about 5% to about 15% of polyethylene glycol. In yet another aspect of this embodiment, a solid formulation comprises about 20% to about 30% by weight of therapeutic compound, about 30% to about 50% by weight of a mixture of mono-, di-, and triglycerides and PEG fatty acid esters, about 10% to about 30% by weight of a glyceryl monolinoleate, and about 7% to about 13% of polyethylene glycol. In still another aspect of this embodiment, a solid formulation comprises about 20% to about 30% by weight of therapeutic compound, about 35% to about 50% by weight of a mixture of mono-, di-, and triglycerides and PEG fatty acid esters, about 15% to about 25% by weight of a glyceryl monolinoleate, and about 7% to about 13% of polyethylene glycol. In a further aspect of this embodiment, a solid formulation comprises about 23% to about 27% by weight of therapeutic compound, about 41% to about 47% by weight of a mixture of mono-, di-, and triglycerides and PEG fatty acid esters, about 18% to about 22% by weight of a glyceryl monolinoleate, and about 9% to about 11% of polyethylene glycol. In other aspects of this embodiment, a polyethylene glycol is, e.g., a PEG 100, a PEG 200, a PEG 300, a PEG 400, a PEG 500, a PEG 600, or a PEG 700.

In an embodiment, an artemesinin or a derivative thereof, is linked to an estrogen receptor modulator, including, without limitation, a selective estrogen receptor modulator. In an embodiment the linkage is covalent bond. In a further embodiment, the linkage is an ionic bond or a non-covalent bond. In an embodiment an artemesinin or a derivative thereof, is linked to an estrogen receptor modulator, including, without limitation, a selective estrogen receptor modulator by a linker. In a further embodiment, the linker is a chemical linker. In an embodiment the linker is synthetic, semisynthetic or derived from a natural product.

Aspects of the present specification disclose, in part, reduction or maintenance of cancer cell population and/or tumor cell size in an individual. As used herein, the term "treating," refers to reduction or maintenance of cancer cell population and/or tumor cell size in an individual. For example, the term "treating" can mean reduction or maintenance of cancer cell population and/or tumor cell size levels in an individual by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with cancer, including the detection of cancer cell population and/or tumor cell size are well known and can be determined by a person of ordinary skill in the art by using commonly known testing means, including blood tests, CT scans sonagrams and other tests known to those of ordinary skill. Those of skill in the art will know the appropriate symptoms or indicators associated with cancer and will know how to determine if an individual is a candidate for treatment as disclosed herein.

A composition or compound is administered to an individual. An individual is typically a human being, but can be an animal, including, but not limited to, dogs, cats, birds, cattle, horses, sheep, goats, reptiles and other animals, whether domesticated or not. Typically, any individual who is a candidate for treatment is a candidate with some form of cancer, whether the cancer is benign or malignant, a tumor, solid or otherwise, a cancer call not located in a tumor or some other form of cancer. Among the most common types of cancer include, but are not limited to, bladder cancer, breast cancer, colon and rectal cancer, endometrial cancer, kidney cancer, renal cancer, leukemia, lung cancer, melanoma, non-Hodgkins lymphoma, pancreatic cancer, prostate cancer, stomach cancer and thyroid cancer. Pre-operative evaluation typically includes routine history and physical examination in addition to thorough informed consent disclosing all relevant risks and benefits of the procedure.

A pharmaceutical composition disclosed herein may comprise a therapeutic compound in a therapeutically effective amount. As used herein, the term "effective amount" is synonymous with "therapeutically effective amount", "effective dose", or "therapeutically effective dose" and when used in reference to reducing or maintaining a cancer cell population and/or tumor cell size in an individual refers to the minimum dose of a therapeutic compound disclosed herein necessary to achieve the desired therapeutic effect and includes a dose sufficient to reduce or maintain of cancer cell population and/or tumor cell size in an individual. The effectiveness of a therapeutic compound disclosed herein capable of reducing or maintaining a cancer cell population and/or tumor cell size in an individual can be determined by observing an improvement in an individual based upon one or more clinical symptoms, and/or physiological indicators associated with reducing or maintaining a cancer cell population and/or tumor cell size in an individual. Maintenance or a reduction of cancer cell population and/or tumor cell size can be indicated by a reduced need for a concurrent therapy. The effectiveness of a therapeutic compound disclosed herein capable of reducing or maintaining a cancer cell population and/or tumor cell size in an individual can be determined by observing an improvement in an individual based upon one or more clinical symptoms, and/or physiological indicators associated with a reduction or maintenance of cancer cell population and/or tumor cell size.

The appropriate effective amount of a therapeutic compound disclosed herein to be administered to reduce or maintain of a cancer cell population and/or tumor cell size in an individual condition can be determined by a person of ordinary skill in the art by taking into account factors, including, without limitation, the measured number of cancer cells in blood samples or biopsies or CAT scans, PET scans, NMR and/or sonagrams taken from or of the individual, the particular characteristics, history and risk factors of the patient, such as, e.g., age, weight, general health and the like, or any combination thereof. Additionally, where repeated administration of a therapeutic compound is used, an effective amount of a therapeutic compound will further depend upon factors, including, without limitation, the frequency of administration, the half-life of the therapeutic compound, or any combination thereof. In is known by a person of ordinary skill in the art that an effective amount of a therapeutic compound disclosed herein can be extrapolated from in vitro assays and in vivo administration studies using animal models prior to administration to humans or animals.

Wide variations in the necessary effective amount are to be expected in view of the differing efficiencies of the various routes of administration. For instance, oral administration of a therapeutic compound disclosed herein generally would be expected to require higher dosage levels than administration by inhalation. Similarly, systemic administration of a therapeutic compound disclosed herein would be expected to require higher dosage levels than a local administration. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors. One skilled in the art will recognize that the condition of the individual can be monitored throughout the course of therapy and that the effective amount of a therapeutic compound disclosed herein that is administered can be adjusted accordingly.

In an embodiment, in instances in which each of the therapeutic compounds themselves are administered, without limitation, as individual or separate dosage forms (e.g., capsules or tablets), the kit comprises, without limitation, each of the therapeutic compounds making up the composition of the invention, along with instructions for use. In an additional embodiment, the therapeutic compound components, without limitation, may be packaged in any manner suitable for administration, so long as the packaging, when considered along with the instructions for administration, without limitation, clearly indicates the manner in which each of the therapeutic compound components is to be administered. In a further embodiment, each of the therapeutic compounds or a combination of such therapeutic compounds may, without limitation, be combined into a single administrable dosage form such as a capsule, tablet, or other solid or liquid formulation. The therapeutic compound can be provided to an individual in a package. The package can be a container, for instance, without limitation, a bottle, a canister, a tube or other enclosed vessel. The package can also be a packet, such as a blister pack.

In an embodiment, the individual or separate dosage is in the form of a blister pack. In an aspect of this embodiment, a blister pack is a term for several types of pre-formed plastic packaging used for small consumer goods, foods, and for pharmaceuticals. In a further embodiment, a blister pack is comprised of a cavity or pocket made from a formable web, usually a thermoformed plastic and typically includes a backing of paperboard or a lidding seal of aluminum foil or plastic. In a further embodiment, a blister that folds onto itself is a clamshell. In an aspect of this embodiment, a blister pack is commonly used as unit-dose packaging for pharmaceutical tablets, capsules or lozenges. In an embodiment, a blister pack can provide barrier protection for shelf life requirements, and a degree of tamper resistance and can be used for packing physician samples of therapeutic compound products or for Over The Counter (OTC) products in the pharmacy.

In an embodiment, an individual is provided a treatment protocol wherein a pharmaceutical composition is administered on a periodic schedule, wherein the individual is informed by electronic notification to administer the therapeutic compound so that the individual is reminded to take the therapeutic compound on a period schedule. In an aspect of this embodiment, the electronic notification is by email, text, instant messaging or by another electronic notification method. In an embodiment, an individual is informed to administer the therapeutic compound on a period schedule through receipt of a telephone call, postal mail, overnight express (including, without limitation, FedEx and UPS) or other method of notification.

In an embodiment, the effectiveness of a cancer therapeutic to kill cancer cells or reduce tumor size is enhanced through the formulation of the cancer therapeutic with one or more fats as compared to the same cancer therapeutic not formulated in a fat. In a further embodiment, the effectiveness of a cancer therapeutic to kill cancer cells or reduce tumor size is enhanced through the formulation of the cancer therapeutic with one or more fats, wherein at least one fat is a solid fat. In an embodiment, the effectiveness of a cancer therapeutic to kill cancer cells or reduce tumor size is enhanced through the formulation of the cancer therapeutic with one or more fats, wherein at least one fat is a liquid. In an embodiment, the effectiveness of a cancer therapeutic, including, without limitation, artemesinin and/or a derivative thereof, to kill cancer cells or reduce tumor size is enhanced through the formulation of the cancer therapeutic with one or more fats as compared to the same cancer therapeutic not formulated in a fat.

In aspects of this embodiment, a therapeutically effective amount of a therapeutic compound disclosed herein reduces or maintains a cancer cell population and/or tumor cell size in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic compound disclosed herein reduces or maintains a cancer cell population and/or tumor cell size in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic compound disclosed herein reduces or maintains a cancer cell population and/or tumor cell size in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 70%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In other aspects of this embodiment, a therapeutically effective amount of a therapeutic compound disclosed herein generally is in the range of about 0.001 mg/kg/day to about 100 mg/kg/day. In aspects of this embodiment, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In other aspects of this embodiment, a therapeutically effective amount of a therapeutic compound disclosed herein generally is in the range of about 1 mg/day to about 3,000 mg/day. In aspects of this embodiment, an effective amount of a therapeutic compound disclosed herein may be, e.g., at least 1 mg/day, at least 5 mg/day, at least 10 mg/day, at least 15 mg/day, at least 20 mg/day, at least 25 mg/day, at least 30 mg/day, at least 40 mg/day, at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day. In yet other aspects of this embodiment, an effective amount of a therapeutic compound disclosed herein may be between, e.g., about 1 mg/day to about 1,000 mg/day, about 5 mg/day to about 1,000 mg/day, about 10 mg/day to about 1,000 mg/day, about 15 mg/day to about 1,000 mg/day, about 20 mg/day to about 1,000 mg/day, about 25 mg/day to about 1,000 mg/day, about 30 mg/day to about 1,000 mg/day, about 40 mg/day to about 1,000 mg/day, about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

In other aspects of this embodiment, a therapeutically effective amount of a artemesinin and/or a derivative thereof disclosed herein generally is in the range of about 0.001 mg/kg/day to about 100 mg/kg/day. In aspects of this embodiment, an effective amount of a statin disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a statin disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a statin disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a statin disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of artemesinin and/or a derivative thereof disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/ day, about 1 mg/kg/day to about 75 mg/kg/day, or about 1 mg/kg/day to about 100 mg/kg/day. In yet other aspects of this embodiment, an effective amount of a statin disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In other aspects of this embodiment, a therapeutically effective amount of artemesinin and/or a derivative thereof disclosed herein generally is in the range of about 1 mg/day to about 3,000 mg/day. In aspects of this embodiment, an effective amount of a statin disclosed herein may be, e.g., at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day. In yet other aspects of this embodiment, an effective amount of a statin disclosed herein may be between, e.g., about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

In other aspects of this embodiment, in conjunction with artemesinin and/or a derivative thereof, a therapeutically effective amount of a second, different cancer therapeutic is in the range of about 0.001 mg/kg/day to about 100 mg/kg/day. In aspects of this embodiment, in conjunction with aretemesinin and/or a derivative thereof, a therapeutically effective amount of a second, different cancer therapeutic may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, in conjunction with aretemesinin and/or a derivative thereof, a therapeutically effective amount of a second, different cancer therapeutic may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, in conjunction with aretemesinin and/or a derivative thereof, a therapeutically effective amount of a second, different cancer therapeutic may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, in conjunction with aretemesinin and/or a derivative thereof, a therapeutically effective amount of a second, different cancer therapeutic herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

Dosing can be single dosage or cumulative (serial dosing), and can be readily determined by one skilled in the art. For instance, reducing or maintaining a cancer cell population and/or tumor cell size in an individual may comprise a one-time administration of an effective dose of a pharmaceutical composition disclosed herein. Alternatively, reducing or maintaining a cancer cell population and/or tumor cell size in an individual may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

Various routes of administration can be useful for administering a therapeutic compound disclosed herein, according to a method for reducing and/or maintaining a cancer cell population and/or tumor cell size in an individual. A pharmaceutical composition may be administered to an individual by any of a variety of means depending, e.g., on the specific therapeutic compound or composition used, or other compound to be included in the composition, and the history, risk factors and symptoms of the individual. As such, topical, enteral, oral, intravenous, subcutaneous, intranasal, rectal, vaginal, intramuscular or parenteral routes of administration may be suitable for reducing or maintaining a cancer cell population and/or tumor cell size in an individual as disclosed herein and such routes include both local and systemic delivery of a therapeutic compound or composition disclosed herein. Compositions comprising either a single therapeutic compound disclosed herein, or two or more therapeutic compounds disclosed herein are intended for inhaled, topical, intranasal, oral, subcutaneous, sublingual, intravenous, rectal and/or vaginal use may be prepared according to any method known to the art for the manufacture of pharmaceutical compositions. A pharmaceutical composition disclosed herein can be administered to an individual in a single formulation or in separate formulations, for combined, simultaneous or sequential administration.

Aspects of the present specification may also be described as follows:

1. A pharmaceutical composition comprising a cancer therapeutic and a pharmaceutically acceptable lipid formulation.
2. The pharmaceutical formulation of embodiment 1, wherein the cancer therapeutic is Artemisnin.
3. The pharmaceutical formulation of embodiment 1, wherein the cancer therapeutic is a derivative of Artemesinin.
4. The pharmaceutical formulation of embodiment 3, wherein the derivative of Artemesinin is Artesunate, Artemether, Dihydroartemisinin, Artelinic acid, Artenimol and/or Artemotil.
5. The pharmaceutical composition of embodiment 1, wherein the composition includes a pharmaceutically acceptable solvent, a pharmaceutically acceptable stabilizing agent, a pharmaceutically acceptable carrier and/or a pharmaceutically acceptable component.
6. The pharmaceutical composition of any proceeding embodiment, wherein the cancer therapeutic is capable of reducing the number of cancer cells or tumor size in an individual suffering from a cancer by, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment.
7. The pharmaceutical composition of any proceeding embodiment, wherein the cancer therapeutic is capable of reducing the number of cancer cells or tumor size in an individual suffering from a cancer by, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.
8. The pharmaceutical composition of embodiment 1, wherein the cancer therapeutic is an alkylating agent.
9. The pharmaceutical composition of embodiment 8, wherein the alkylating agent is Cisplatin, carboplatin, mechlorethamine, cyclophosphamide, chlorambucil, ifosfamide and/or oxaliplatin.
10. The pharmaceutical composition of embodiment 1, wherein the cancer therapeutic is an anti-metabolite.
11. The pharmaceutical composition of embodiment 10, wherein the anti-metabolite is azathioprine and/or mercaptopurine.
12. The pharmaceutical composition of embodiment 10, wherein the anti-metabolite is a synthetic, semisynthetic or derivative of an anti-metabolite.
13. The pharmaceutical composition of embodiment 1, wherein the cancer therapeutic is a terpenoid.
14. The pharmaceutical composition of embodiment 13, wherein the terpenoid is a vinca alkaloid and/or a taxane.
15. The pharmaceutical composition of embodiment 14, wherein the vinca alkaloid is Vincristine, Vinblastine, Vinorelbine and/or Vindesine.
16. The pharmaceutical composition of embodiment 14, wherein the taxane is Taxol, Paclitaxel and/or Docetaxel.
17. The pharmaceutical composition of embodiment 14, wherein the taxane is a synthetic, semisynthetic or derivative of a taxane.
18. The pharmaceutical composition of embodiment 1, wherein the cancer therapeutic is a topoisomerase.
19. The pharmaceutical composition of embodiment 18, wherein the topoisomerase is a type I topoisomerase.
20. The pharmaceutical composition of embodiment 19, wherein the type 1 topoisomerase is camptothecins.
21. The pharmaceutical composition of embodiment 20, wherein the campotothecins is irinotecan and/or topotecan.
22. The pharmaceutical composition of embodiment 18, wherein the topoisomerase is a type II topoisomerase.
23. The pharmaceutical composition of embodiment 22, wherein the type II topoisomerase is amsacrine, etoposide, etoposide phosphate and/or teniposide.
24. The pharmaceutical composition of any of embodiments 18-23, wherein the topoisomerase is a synthetic, semisynthetic and/or derivative.
25. The pharmaceutical composition of embodiment 24, wherein the derivative is epipodophyllotoxins.
26. The pharmaceutical composition of embodiment 1, wherein the cancer therapeutic is a cytotoxic antibiotic.
27. The pharmaceutical composition of embodiment 26, wherein the cytotoxic antibiotic is actinomycin, anthracyclines, doxorubicin, daunorubicin, valrubicin, idarubicin, epirubicin, bleomycin, plicamycin and/or mitomycin.
28. The pharmaceutical composition of embodiment 1, wherein the cancer therapeutic is a hormone.
29. The pharmaceutical composition of embodiment 28, wherein the hormone is a lutenizing hormone releasing hormone agonist.
30. The pharmaceutical composition of embodiment 28, wherein the hormone is leuprolidine, goserelin, triptorelin, histrelin, bicalutamide, flutamide and/or nilutamide.
31. The pharmaceutical composition of embodiment 1, wherein the cancer therapeutic is an antibody.
32. The pharmaceutical composition of embodiment 31, wherein the antibody is Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab.

33. The pharmaceutical composition of embodiment 3, wherein the derivative is a butyrate ester of dihydroartemesinin.

34. The pharmaceutical composition of any of the preceding embodiments, wherein the cancer therapeutic has a half-life of one hour.

35. The pharmaceutical composition of any of the preceding embodiments, wherein the dosing of the cancer therapeutic is daily.

36. The pharmaceutical composition of any of the preceding embodiments, wherein the cancer therapeutic has a half-life of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months and/or four months.

37. The pharmaceutical composition of any of the preceding embodiments, wherein the cancer therapeutic is administered to an individual for a period of time followed by a separate period of time.

38. The pharmaceutical composition of any of the preceding embodiments, wherein the cancer therapeutic is administered for a first period and a second period following the first period, with administration stopped during the second period, followed by a third period where administration of the therapeutic compound is started and then a fourth period following the third period where administration is stopped.

39. The pharmaceutical composition of any of the preceding embodiments, wherein the cancer therapeutic is administered for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months and/or 12 months.

40. The pharmaceutical composition of any of the preceding embodiments, wherein a first cancer therapeutic s administered to an individual and at a later date, a second cancer therapeutic is administered to the same individual.

41. The pharmaceutical composition of any of the preceding embodiments, wherein the first therapeutic compound is artemesinin or a derivative thereof and the second therapeutic compound is a different derivative of artemesinin.

42. The pharmaceutical composition of any of the preceding embodiments, wherein the first therapeutic compound is artemesinin or a derivative thereof and the second therapeutic compound is a cancer therapeutic that is not artemesinin or a derivative thereof.

43. The pharmaceutical composition of any of the preceding embodiments, wherein a first therapeutic compound is administered to an individual at the same time as a second therapeutic compound is administered to the individual.

44. The pharmaceutical composition of any of the preceding embodiments, wherein the first therapeutic compound is a artemesinin or derivative thereof and the second therapeutic compound is a different derivative of artemesinin.

45. The pharmaceutical composition of any of the preceding embodiments, wherein the first therapeutic compound is artemesinin or a derivative thereof and the second therapeutic compound is a cancer therapeutic that is not artemesinin or a derivative thereof.

46. The pharmaceutical composition of any of the preceding embodiments, wherein the pharmaceutical composition is a liquid, a sold and/or a semi-solid.

47. The pharmaceutical composition of embodiment 46, wherein, the pharmaceutical composition is provided to an individual in a capsule, tablet, pill, lozenge, powder and/or granule.

48. The pharmaceutical composition of embodiment 46, wherein the pharmaceutical composition is inhaled.

49. The pharmaceutical composition of embodiment 1, wherein the pharmaceutical composition is formulated in an oil-in-water emulsion.

50. The pharmaceutical composition of embodiment 49, wherein the oil is a vegetable oil, an animal fat and/or a mineral oil.

51. The pharmaceutical composition of embodiment 1, wherein the pharmaceutical composition is released in a controlled release profile over time.

52. The pharmaceutical composition of embodiment 1, wherein the pharmaceutical composition is provided in an extended release therapeutic compound delivery form.

53. The pharmaceutical composition of embodiment 1, wherein the pharmaceutical composition is provided in a sustained release therapeutic compound deliver form.

54. The pharmaceutical composition of embodiment 53, wherein the sustained release therapeutic compound delivery platform releases a therapeutic compound with substantially zero order release kinetics over a period of about 7 days after administration, about 15 days after administration, about 30 days after administration, about 45 days after administration, about 60 days after administration, about 75 days after administration and/or about 90 days after administration.

55. The pharmaceutical composition of embodiment 53, wherein the sustained release therapeutic compound delivery platform releases a therapeutic compound with substantially zero order release kinetics over a period of at least 7 days after administration, at least 15 days after administration, at least 30 days after administration, at least 45 days after administration, at least 60 days after administration, at least 75 days after administration, or at least 90 days after administration.

56. The pharmaceutical composition of embodiment 53, wherein the sustained release therapeutic compound delivery platform releases a therapeutic compound with substantially first order release kinetics over a period of about 7 days after administration, about 15 days after administration, about 30 days after administration, about 45 days after administration, about 60 days after administration, about 75 days after administration, or about 90 days after administration.

57. The pharmaceutical composition of embodiment 53, wherein the sustained release therapeutic compound delivery platform releases a therapeutic compound with substantially first order release kinetics over a period of at least 7 days after administration, at least 15 days after administration, at least 30 days after administration, at least 45 days after administration, at least 60 days after administration, at least 75 days after administration, or at least 90 days after administration.
58. The pharmaceutical composition of embodiment 53, wherein a therapeutic compound delivery platform releases a therapeutic compound with substantially zero order release kinetics over a period of about 1 day after administration, about 2 days after administration, about 3 days after administration, about 4 days after administration, about 5 days after administration, or about 6 days after administration.
59. The pharmaceutical composition of embodiment 53, wherein a therapeutic compound delivery platform releases a therapeutic compound with substantially zero order release kinetics over a period of, e.g., at most 1 day after administration, at most 2 days after administration, at most 3 days after administration, at most 4 days after administration, at most 5 days after administration, or at most 6 days after administration.
60. The pharmaceutical composition of embodiment 53, wherein a therapeutic compound delivery platform releases a therapeutic compound disclosed herein with substantially first order release kinetics over a period of about 1 day after administration, about 2 days after administration, about 3 days after administration, about 4 days after administration, about 5 days after administration, or about 6 days after administration.
61. The pharmaceutical composition of embodiment 53, wherein a therapeutic compound delivery platform releases a therapeutic compound disclosed herein with substantially first order release kinetics over a period of at most 1 day after administration, at most 2 days after administration, at most 3 days after administration, at most 4 days after administration, at most 5 days after administration, or at most 6 days after administration.
62. The pharmaceutical composition of any preceeding embodiment, wherein a therapeutic compound has a log P value indicating that the compound is at least 50% soluble in an organic solvent, at least 60% soluble in an organic solvent, at least 70% soluble in an organic solvent, at least 80% soluble in an organic solvent, or at least 90% soluble in an organic solvent.
63. The pharmaceutical composition of any preceeding embodiment, wherein a therapeutic compound has a log P value indicating that the compound is between, e.g., about 50% to about 100% soluble in an organic solvent, about 60% to about 100% soluble in an organic solvent, about 70% to about 100% soluble in an organic solvent, about 80% to about 100% soluble in an organic solvent, or about 90% to about 100% soluble in an organic solvent.
64. The pharmaceutical composition of any preceeding embodiment, wherein a therapeutic compound has a log P value of, e.g., more than 1.1, more than 1.2, more than 1.4, more than 1.6, more than 1.8, more than 2.0, more than 2.2, more than 2.4, more than 2.6, more than 2.8, more than 3.0, more than 3.2, more than 3.4, or more than 3.6.
65. The pharmaceutical composition of any preceeding embodiment, wherein a therapeutic compound has a log P value in the range of, e.g., between 1.8 and 4.0, between 2.0 and 4.0, between 2.1 and 4.0, between 2.2 and 4.0, or between 2.3 and 4.0, between 2.4 and 4.0, between 2.5 and 4.0, between 2.6 and 4.0, or between 2.8 and 4.0.
66. The pharmaceutical composition of any preceeding embodiment, wherein a therapeutic compound has a log P value in the range of, e.g., between 3.0 and 4.0, or between 3.1 and 4.0, between 3.2 and 4.0, between 3.3 and 4.0, between 3.4 and 4.0, between 3.5 and 4.0, or between 3.6 and 4.0.
67. The pharmaceutical composition of any preceeding embodiment, wherein, a therapeutic compound has a log P value in the range of, e.g., between 2.0 and 2.5, between 2.0 and 2.7, between 2.0 and 3.0, or between 2.2 and 2.5.
68. The pharmaceutical composition of any preceeding embodiment, wherein a therapeutic compound has a polar surface area of, e.g., less than 8.0 $nm^2$, less than 7.0 $nm^2$, less than 6.0 $nm^2$, less than 5.0 $nm^2$, less than 4.0 $nm^2$, or less than 3.0 $nm^2$.
69. The pharmaceutical composition of any preceeding embodiment, wherein a therapeutic compound has a polar surface area in the range of, e.g., between 3.0 $nm^2$ and 6.5 $nm^2$, between 3.0 $nm^2$ and 6.0 $nm^2$, between 3.0 $nm^2$ and 5.5 $nm^2$, between 3.0 $nm^2$ and 5.0 $nm^2$, between 3.0 $nm^2$ and 4.5 $nm^2$, between 3.5 $nm^2$ and 6.5 $nm^2$, between 3.5 $nm^2$ and 6.0 $nm^2$, between 3.5 $nm^2$ and 5.5 $nm^2$, between 3.5 $nm^2$ and 5.0 $nm^2$, between 3.5 $nm^2$ and 4.5 $nm^2$, between 4.0 $nm^2$ and 6.5 $nm^2$, between 4.0 $nm^2$ and 6.0 $nm^2$, between 4.0 $nm^2$ and 5.5 $nm^2$, or between 4.0 $nm^2$ and 5.0 $nm^2$, between 4.0 $nm^2$ and 4.5 $nm^2$, or between 4.5 $nm^2$ and 5.5 $nm^2$.
70. The pharmaceutical composition of any preceeding embodiment, wherein a therapeutic compound has a polar surface area in the range of, e.g., between 2.0 $nm^2$ and 6.5 $nm^2$, between 2.0 $nm^2$ and 6.0 $nm^2$, between 2.0 $nm^2$ and 5.5 $nm^2$, between 2.0 $nm^2$ and 5.0 $nm^2$, between 2.0 $nm^2$ and 4.5 $nm^2$, between 2.5 $nm^2$ and 6.5 $nm^2$, between 2.5 $nm^2$ and 6.0 $nm^2$, between 2.5 $nm^2$ and 5.5 $nm^2$, between 2.5 $nm^2$ and 5.0 $nm^2$, or between 2.5 $nm^2$ and 4.5 $nm^2$.
71. The pharmaceutical composition of embodiment 1, wherein the cancer therapeutic is an ester.
72. The pharmaceutical composition of embodiment 5, wherein the solvent is in an amount sufficient to dissolve a cancer therapeutic.
73. The pharmaceutical composition of embodiment 72, wherein the pharmaceutical comprises a solvent in an amount of less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v).
74. The pharmaceutical composition of embodiment 72, wherein the pharmaceutical composition comprises a solvent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

75. The pharmaceutical composition of embodiment 5, wherein the solvent comprises a pharmaceutically acceptable alcohol.
76. The pharmaceutical composition of embodiment 75, wherein the alcohol is a $C_{2-4}$ alcohol, a $C_{1-4}$ alcohol, a $C_{1-5}$ alcohol, a $C_{1-7}$ alcohol, a $C_{1-10}$ alcohol, a $C_{1-15}$ alcohol, or a $C_{1-20}$ alcohol.
77. The pharmaceutical composition of embodiment 75, wherein the alcohol is a primary alcohol, a secondary alcohol, or a tertiary alcohol.
78. The pharmaceutical composition of embodiment 75, wherein the alcohol is an acyclic alcohol, a monohydric alcohol, a polyhydric alcohol (also known as a polyol or sugar alcohol), an unsaturated aliphatic alcohol, an alicyclic alcohol, or a combination thereof.
79. The pharmaceutical composition of embodiment 75, wherein the alcohol is an unsaturated aliphatic alcohol.
80. The pharmaceutical composition of embodiment 75, wherein the unsaturated aliphatic alcohol is prop-2-ene-1-ol, 3,7-dimethylocta-2,6-dien-1-ol, and prop-2-in-1-ol.
81. The pharmaceutical composition of embodiment 75, wherein an alcohol is an alicyclic alcohol.
82. The pharmaceutical composition of embodiment 75, wherein the alicyclic alcohol is cyclohexane-1,2,3,4,5,6-hexyl and 2-(2-propyl)-5-methyl-cyclohexane-1-ol.
83. The pharmaceutical composition of embodiment 5, wherein a solvent is an ester of pharmaceutically-acceptable alcohol and an acid.
84. The pharmaceutical composition of embodiment 83 wherein an ester of a pharmaceutically-acceptable acid is acetic acid, butaric acid, and formic acid.
85. The pharmaceutical composition of embodiment 83, wherein the ester of an alcohol and an acid are methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate or 1-hexadecyl formate.
86. The pharmaceutical composition of embodiment 5, wherein the solvent is a pharmaceutically-acceptable glycol either.
87. The pharmaceutical composition of embodiment 86, wherein the glycol ether is diethylene glycol monomethyl ether (2-(2-methoxyethoxy)ethanol), diethylene glycol monoethyl ether (2-(2-ethoxyethoxy)ethanol), diethylene glycol monopropyl ether (2-(2-propoxyethoxy)ethanol), diethylene glycol monoisopropyl ether (2-(2-isopropoxyethoxy)ethanol), and diethylene glycol mono-n-butyl ether (2-(2-butoxyethoxy)ethanol).
88. The pharmaceutical composition of embodiment 5, wherein the composition comprises one or more lipids.
89. The pharmaceutical composition of embodiment 88, wherein the lipid is a fatty acids, glycerolipids, diglycerides, and triglycerides), phospholipids, sphingolipids, sterol lipids, prenol lipids, saccharolipids, and/or polyketides.
90. The pharmaceutical composition of embodiment 88, wherein the lipid is an oil, an oil-based liquid, a fat, a fatty acid, a partially hydrolyzed fatty acid, a wax, a fatty acid ester, a fatty acid salt, a fatty alcohol, a glyceride (mono-, di- or tri-glyceride), a phospholipids, a glycol ester, a sucrose ester, a glycerol oleate derivative, a medium chain triglyceride and.or a partially hydrolyzed triglyceride.
91. The pharmaceutical composition of embodiment 88, wherein the lipid is Capryllic acid (8:0), pelargonic acid (9:0), Capric acid (10:0), Undecylic acid (11:0), Lauric acid (12:0), Tridecylic acid (13:0), Myristic acid (14:0), Myristoleic acid (14:1), Pentadecyclic acid (15:0), Palmitic acid (16:0), Palmitoleic acid (16:1), Sapienic acid (16:1), Margaric acid (17:0), Stearic acid (18:0), Oleic acid (18:1), Elaidic acid (18:1), Vaccenic acid (18:1), Linoleic acid (18:2), Linoelaidic acid (18:2), α-Linolenic acid (18:3), γ-Linolenic acid (18:3), Stearidonic acid (18:4), Nonadecylic acid (19:0), Arachidic acid (20:0), Eicosenoic acid (20:1), Dihomo-γ-linolenic acid (20:3), Mead acid (20:3), Arachidonic acid (20:4), Eicosapentaenoic acid (20:5), Heneicosylic acid (21:0), Behenic acid (22:0), Erucic acid (22:1), Docosahexaenoic acid (22:6), Tricosylic acid (23:0), Lignoceric acid (24:0), Nervonic acid (24:1), Pentacosylic acid (25:0), Cerotic acid (26:0), Heptacosylic acid (27:0), Montanic acid (28:0), Nonacosylic acid (29:0), Melissic acid (30:0), Henatriacontylic acid (31:0), Lacceroic acid (32:0), Psyllic acid (33:0), Geddic acid (34:0), Ceroplastic acid (35:0), and/or Hexatriacontylic acid (36:0).
92. The pharmaceutical composition of embodiment 88, wherein the lipid is a pharmaceutically-acceptable saturated or unsaturated fatty acid.
93. The pharmaceutical composition of embodiment 92, wherein the saturated or unsaturated fatty acid comprises at least 8, at least 10, at least 12, at least 14, at least 16, at least 18, at least 20, at least 22, at least 24, at least 26, at least 28, or at least 30 carbon atoms,
94. The pharmaceutical composition of embodiment 92, wherein the saturated or unsaturated fatty acid comprises between 4 and 24 carbon atoms, between 6 and 24 carbon atoms, between 8 and 24 carbon atoms, between 10 and 24 carbon atoms, between 12 and 24 carbon atoms, between 14 and 24 carbon atoms, or between 16 and 24 carbon atoms, between 4 and 22 carbon atoms, between 6 and 22 carbon atoms, between 8 and 22 carbon atoms, between 10 and 22 carbon atoms, between 12 and 22 carbon atoms, between 14 and 22 carbon atoms, or between 16 and 22 carbon atoms, between 4 and 20 carbon atoms, between 6 and 20 carbon atoms, between 8 and 20 carbon atoms, between 10 and 20 carbon atoms, between 12 and 20 carbon atoms, between 14 and 20 carbon atoms, or between 16 and 20 carbon atoms.
95. The pharmaceutical composition of embodiment 92, wherein the unsaturated fatty acid has 1 or more, 2 or more, 3 or more, 4 or more, 5 or more, or 6 or more double bonds.
96. The pharmaceutical composition of any proceeding embodiment, wherein the concentration of a therapeutic compound is at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL.
97. The pharmaceutical composition of any proceeding embodiment, wherein the concentration of a therapeutic compound is at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL.
98. The pharmaceutical composition of any proceeding embodiment, wherein the concentration of a therapeutic compound is about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

99. The pharmaceutical composition of any proceeding embodiment, wherein the ratio of solution:adjuvant is at least 5:1, at least 4:1, at least 3:1, at least 2:1, at least 0:1, at least 1:1, at least 1:2, at least 1:3, at least 1:4, at least 1:5, at least 1:6, at least 1:7, at least 1:8, at least 1:9, at least 1:10, at least 1:15, at least 1:20, or at least 1:25.

100. The pharmaceutical composition of any proceeding embodiment, wherein the ratio of solution:adjuvant is about 5:1 to about 1:25, about 4:1 to about 1:25, about 3:1 to about 1:25, about 2:1 to about 1:25, about 0:1 to about 1:25, about 1:1 to about 1:25, about 1:2 to about 1:25, about 1:3 to about 1:25, about 1:4 to about 1:25, about 1:5 to about 1:25, about 5:1 to about 1:20, about 4:1 to about 1:20, about 3:1 to about 1:20, about 2:1 to about 1:20, about 0:1 to about 1:20, about 1:1 to about 1:20, about 1:2 to about 1:20, about 1:3 to about 1:20, about 1:4 to about 1:20, about 1:5 to about 1:20, about 5:1 to about 1:15, about 4:1 to about 1:15, about 3:1 to about 1:15, about 0:1 to about 1:15, about 2:1 to about 1:15, about 1:1 to about 1:15, about 1:2 to about 1:15, about 1:3 to about 1:15, about 1:4 to about 1:15, about 1:5 to about 1:15, about 5:1 to about 1:12, about 4:1 to about 1:12, about 3:1 to about 1:12, about 2:1 to about 1:12, about 0:1 to about 1:12, about 1:1 to about 1:12, about 1:2 to about 1:12, about 1:3 to about 1:12, about 1:4 to about 1:12, about 1:5 to about 1:12, about 1:6 to about 1:12, about 1:7 to about 1:12, about 1:8 to about 1:12, about 5:1 to about 1:10, about 4:1 to about 1:10, about 3:1 to about 1:10, about 2:1 to about 1:10, about 0:1 to about 1:10, about 1:1 to about 1:10, about 1:2 to about 1:10, about 1:3 to about 1:10, about 1:4 to about 1:10, about 1:5 to about 1:10, about 1:6 to about 1:10, about 1:7 to about 1:10, or about 1:8 to about 1:10.

101. The pharmaceutical composition of any proceeding embodiment, wherein the ratio of fat:fat, is at least 5:1, at least 4:1, at least 3:1, at least 2:1, at least 0:1, at least 1:1, at least 1.1:1, at least 1.2:1, at least 1.3:1, at least 1.4:1, at least 1.5:1, at least 1.6:1, at least 1.7:1, at least 1.8:1, at least 1.9:1, at least 1:2, at least 1:3, at least 1:4, at least 1:5, at least 1:6, at least 1:7, at least 1:8, at least 1:9, at least 1:10, at least 1:15, at least 1:20, or at least 1:25.

102. The pharmaceutical composition of any proceeding embodiment, wherein the ratio of fat:fat may be in a range of about 5:1 to about 1:25, about 4:1 to about 1:25, about 3:1 to about 1:25, about 2:1 to about 1:25, about 0:1 to about 1:25, about 1:1 to about 1:25, about 1:2 to about 1:25, about 1:3 to about 1:25, about 1:4 to about 1:25, about 1:5 to about 1:25, about 5:1 to about 1:20, about 4:1 to about 1:20, about 3:1 to about 1:20, about 2:1 to about 1:20, about 0:1 to about 1:20, about 1:1 to about 1:20, about 1:2 to about 1:20, about 1:3 to about 1:20, about 1:4 to about 1:20, about 1:5 to about 1:20, about 5:1 to about 1:15, about 4:1 to about 1:15, about 3:1 to about 1:15, about 0:1 to about 1:15, about 2:1 to about 1:15, about 1:1 to about 1:15, about 1:2 to about 1:15, about 1:3 to about 1:15, about 1:4 to about 1:15, about 1:5 to about 1:15, about 5:1 to about 1:12, about 4:1 to about 1:12, about 3:1 to about 1:12, about 2:1 to about 1:12, about 0:1 to about 1:12, about 1:1 to about 1:12, about 1:2 to about 1:12, about 1:3 to about 1:12, about 1:4 to about 1:12, about 1:5 to about 1:12, about 1:6 to about 1:12, about 1:7 to about 1:12, about 1:8 to about 1:12, about 5:1 to about 1:10, about 4:1 to about 1:10, about 3:1 to about 1:10, about 2:1 to about 1:10, about 0:1 to about 1:10, about 1:1 to about 1:10, about 1:2 to about 1:10, about 1:3 to about 1:10, about 1:4 to about 1:10, about 1:5 to about 1:10, about 1:6 to about 1:10, about 1:7 to about 1:10, or about 1:8 to about 1:10.

103. The pharmaceutical composition of any proceeding embodiment, wherein the ratio of fat:fat, in a pharmaceutical composition containing artemesinin or a derivate thereof, is at least 5:1, at least 4:1, at least 3:1, at least 2:1, at least 0:1, at least 1:1, at least 1.1:1, at least 1.2:1, at least 1.3:1, at least 1.4:1, at least 1.5:1, at least 1.6:1, at least 1.7:1, at least 1.8:1, at least 1.9:1, at least 1:2, at least 1:3, at least 1:4, at least 1:5, at least 1:6, at least 1:7, at least 1:8, at least 1:9, at least 1:10, at least 1:15, at least 1:20, or at least 1:25.

104. The pharmaceutical composition of any proceeding embodiment, wherein the ratio of fat:fat, in a pharmaceutical composition containing artemesinin or a derivate thereof, is in a range of about 5:1 to about 1:25, about 4:1 to about 1:25, about 3:1 to about 1:25, about 2:1 to about 1:25, about 0:1 to about 1:25, about 1:1 to about 1:25, about 1:2 to about 1:25, about 1:3 to about 1:25, about 1:4 to about 1:25, about 1:5 to about 1:25, about 5:1 to about 1:20, about 4:1 to about 1:20, about 3:1 to about 1:20, about 2:1 to about 1:20, about 0:1 to about 1:20, about 1:1 to about 1:20, about 1:2 to about 1:20, about 1:3 to about 1:20, about 1:4 to about 1:20, about 1:5 to about 1:20, about 5:1 to about 1:15, about 4:1 to about 1:15, about 3:1 to about 1:15, about 0:1 to about 1:15, about 2:1 to about 1:15, about 1:1 to about 1:15, about 1:2 to about 1:15, about 1:3 to about 1:15, about 1:4 to about 1:15, about 1:5 to about 1:15, about 5:1 to about 1:12, about 4:1 to about 1:12, about 3:1 to about 1:12, about 2:1 to about 1:12, about 0:1 to about 1:12, about 1:1 to about 1:12, about 1:2 to about 1:12, about 1:3 to about 1:12, about 1:4 to about 1:12, about 1:5 to about 1:12, about 1:6 to about 1:12, about 1:7 to about 1:12, about 1:8 to about 1:12, about 5:1 to about 1:10, about 4:1 to about 1:10, about 3:1 to about 1:10, about 2:1 to about 1:10, about 0:1 to about 1:10, about 1:1 to about 1:10, about 1:2 to about 1:10, about 1:3

105. The pharmaceutical composition of embodiment 88, wherein a cancer therapeutic is formulated in a one fat.
106. The pharmaceutical composition of embodiment 88, wherein artemesinin or a derivative thereof is formulated in one fat.
107. The pharmaceutical composition of embodiment 88, wherein a cancer therapeutic is formulated in two fats.
108. The pharmaceutical composition of embodiment 88, wherein artemesinin or a derivative thereof is formulated in two fats.
109. The pharmaceutical composition of embodiment 88, wherein a cancer therapeutic is formulated in three fats, four fats, five fats, six fats or seven or more fats.
110. The pharmaceutical composition of embodiment 88, wherein artemesinin or a derivative thereof is formulated in three fats, four fats, five fats, six fats or seven or more fats.
111. The pharmaceutical composition of embodiment 88, wherein a cancer therapeutic is formulated in a fat that is a liquid.
112. The pharmaceutical composition of embodiment 88, wherein a cancer therapeutic is formulated in at fat that is a solid.
113. The pharmaceutical composition of embodiment 88, wherein a cancer therapeutic is formulated in a two or more fats that are liquids.
114. The pharmaceutical composition of embodiment 88, wherein a cancer therapeutic is formulated in two or more fats that are solids.
115. The pharmaceutical composition of embodiment 88, wherein a cancer therapeutic is formulated in two or more fats, wherein at least one fat is a solid and at least one fat is a liquid.
116. The pharmaceutical composition of any of embodiments 111-115, wherein the cancer therapeutic is artemesinin and/or a derivative thereof.
117. The pharmaceutical composition of any proceeding embodiment, wherein the concentration of a cancer therapeutic is at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL.
118. The pharmaceutical composition of any proceeding embodiment, wherein the concentration of a cancer therapeutic is at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL.
119. The pharmaceutical composition of any proceeding embodiment, wherein the concentration of a cancer therapeutic is about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.
120. The pharmaceutical composition of any of embodiments 1-4, wherein the composition is a liquid, semi-solid or a solid formulation.
121. The pharmaceutical composition of any of embodiments 1-4 and 88, wherein the pharmaceutical composition comprises tributyrin and G43
122. The pharmaceutical composition of any of embodiments 1-4, wherein an artemesinin or a derivative thereof is linked to a estrogen receptor modulator.
123. The pharmaceutical composition of embodiment 122, wherein the estrogen receptor modulator is a selective estrogen receptor modulator.
124. The pharmaceutical composition of embodiment 1, wherein the cancer therapeutic is a stilbenoid.
125. The pharmaceutical composition of embodiment 124, wherein the stilbenoid is Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A.
126. The pharmaceutical composition of embodiment 1, wherein the cancer therapeutic is an isoflavone.
127. The pharmaceutical composition of embodiment 124, wherein the isoflavone is Daidzein or Genistein.
128. The pharmaceutical composition of embodiment 1, wherein the cancer therapeutic is an isoflavondiol.
129. The pharmaceutical composition of embodiment 124, wherein the isoflavondiol is Daidzein or Genistein.
130. The pharmaceutical composition of any of embodiments 124-129, wherein the cancer therapeutic is administered with an Artemesinin.
131. The pharmaceutical composition of embodiment 130, wherein the Artemesinin is a derivative of Artemesinin.
132. The pharmaceutical composition of embodiment 131, wherein the derivative is Artesunate, Artemether, Dihydroartemisinin, Artelinic acid, Artenimol and/or Artemotil.
133. The pharmaceutical composition of any of embodiments 124-129, wherein the stilbenoid, isoflavone and/or isoflavondiol is a synthetic, semisynthetic or derivative.
134. A pharmaceutical composition comprising one or more cancer therapeutics.
135. The pharmaceutical formulation of embodiment 134, wherein a cancer therapeutic is selected from an alkylating agent, an anti-metabolite, a plant alkaloid, a terpenoid, a topoisomerase inhibitor, a cytotoxic antibiotics, a statin, an anti-diabetic drug, a PPAR-y, a PPAR-J3, a PPAR-a, an antibiotic, an antihelminthic, an anti-malaria drug, a vitamin and/or a food additive.

136. The pharmaceutical formulation of embodiment 135, wherein the alkylating agent is carboplatin, chlorambucil, cisplatin, cyclophosphamide, ifosfamide, oxaliplatin and/or mechlorethamine.

137. The pharmaceutical formulation of embodiment 135, wherein the antimetabolite is azathioprine and/or mercaptopurine.

138. The pharmaceutical formulation of embodiment 135, wherein the plant alkaloid is a vinca alkaloid, a podophyllotoxin and/or a taxane.

139. The pharmaceutical formulation of embodiment 135, wherein the vinca alkaloid is vincristine, vinblastine, vinorelbine and/or vindesine.

140. The pharmaceutical formulation of embodiment 135, wherein the podophyllotoxin is etoposide and/or teniposide.

141. The pharmaceutical formulation of embodiment 135, wherein the taxane is docetaxel and/or ortataxel.

142. The pharmaceutical formulation of embodiment 135, wherein the topoisomerase is a type (topoisomerase inhibitor or a type II topoisomerase inhibitor.

143. The pharmaceutical formulation of embodiment 135, wherein the type I topoisomerase inhibitor is a camptothecin.

144. The pharmaceutical formulation of embodiment 135, wherein the camptothecin is exatecan, irinotecan, lurtotecan, topotecan, BNP 1350, CKD 602, DB 67 (AR67) and/or ST 1481.

145. The pharmaceutical formulation of embodiment 135, wherein the type II topoisomerase inhibitor is epipodophyllotoxin.

146. The pharmaceutical formulation of embodiment 135, wherein the epipodophyllotoxin is, without limitation, amsacrine, etoposid, etoposide phosphate and/or teniposide.

147. The pharmaceutical formulation of embodiment 135, wherein the cytotoxic antibiotic is an actinomycin, an anthracenedione, an anthracycline, thalidomide, dichloroacetic acid, nicotinic acid, 2-deoxyglucose and/or chlofazimine.

148. The pharmaceutical formulation of embodiment 135, wherein the actinomycin is actinomycin D, bacitracin, colistin (polymyxin E) and/or polymyxin B.

149. The pharmaceutical formulation of embodiment 135, wherein the antracenedione is mitoxantrone and/or pixantrone.

150. The pharmaceutical formulation of embodiment 135, wherein the anthracycline is bleomycin, doxorubicin (Adriamycin), daunorubicin (daunomycin), epirubicin, idarubicin, mitomycin, plicamycin and/or valrubicin.

151. The pharmaceutical formulation of embodiment 135, wherein the statin is atorvastatin, fluvastin, lovastatin, pitavastatin, pravastatin, rosuvastatin and/or simvastatin.

152. The pharmaceutical formulation of embodiment 135, wherein the treatment of diabetes is a biguanide, a thiazolidinedione, a secretagogue, an alpha-glucosidase inhibitor and/or a peptide analog.

153. The pharmaceutical formulation of embodiment 135, wherein the biguanide is metformin, phenformin and/or buformin.

154. The pharmaceutical formulation of embodiment 135, wherein the thiazolidinedione is rosiglitazone, pioglitazone and/or troglitazone.

155. The pharmaceutical formulation of embodiment 135, wherein the secretagogue is a sulfonylurea, a nonsulfonylurea and/or a meglitinide.

156. The pharmaceutical formulation of embodiment 135, wherein the sulfonylurea is tolbutamide, acetohexamide, tolazamide, chlorpropamide, glipzide, glyburide, glimepiride, gliclazide, glycopyramide and/or gliquidone.

157. The pharmaceutical formulation of embodiment 135, wherein the meglitinide is repaglinide and/or nateglinide.

158. The pharmaceutical formulation of embodiment 135, wherein the alpha-glucosidase inhibitor is miglitol, acarbose and/or voglibose.

159. The pharmaceutical formulation of embodiment 135, wherein the peptide analog is an injectable incretin mimetic, an injectable glucagon-like peptide analog and/or agonist, a gastric inhibitory peptide analog, a dipeptidyl peptidase-4 inhibitor and/or an injectable Amylin analogue.

160. The pharmaceutical formulation of embodiment 135, wherein the glucagon-like peptide analog and/or agonist is exenatide, liraglutide and/or taspoglutide.

161. The pharmaceutical formulation of embodiment 135, wherein the dipeptidyl peptidase-4 inhibitor is vildagliptin, sitagliptin, saxagliptin, linagliptin, allogliptin and/or septagliptin.

162. The pharmaceutical formulation of embodiment 135, wherein the injectable Amylin analogue is pramlintide.

163. The pharmaceutical formulation of embodiment 135, wherein the cancer therapeutic is cinnamon and/or thiamine.

164. The pharmaceutical formulation of embodiment 135, wherein the Peroxisome proliferator-activated receptor gamma is rosiglitazone, troglitazone, pioglitazone, netoglitazone, rivoglitazone and/or ciglitazone.

165. The pharmaceutical formulation of embodiment 135, wherein the PPAR-r3 agonist is endurobol and/or GW0742.

166. The pharmaceutical formulation of embodiment 135, wherein the antibiotic is isoniazid, rifampicin, pyrazinamide and/or ethambutol.

167. The pharmaceutical formulation of embodiment 135, wherein the antihelminthic is abamectin, an aminoacetonitriles, a benzimadazole, diethylcaramazine, ivermectin, levamisole, niclosamide, an octadepsipeptides, phosphoric acid (metrifonate), praziquantel, a spiroindoles, suramin and/or pyrantel pamoate.

168. The pharmaceutical formulation of embodiment 135, wherein the aminoacetonitrile is monepantel.

169. The pharmaceutical formulation of embodiment 135, wherein the benzimidazole is albendazole, fenbendazole, aflubendazole, thiabendazole and triclabendazole.

170. The pharmaceutical formulation of embodiment 135, wherein the flubendazole is mebendazole.

171. The pharmaceutical formulation of embodiment 135, wherein the octadepsipeptide is emodepside.

172. The pharmaceutical formulation of embodiment 135, wherein the spiroindole is dequantel.

173. The pharmaceutical formulation of embodiment 135, wherein the anti-malarial therapeutic is amodiaquine, an artemisinin, atovaquone, chloroquine, clindamycin, doxycycline, halofantrine, mefloquine, primaquine, proguanil, pyrimethamine, a quinine and related agent, rufigallol, and/or a sulphonamide.

174. The pharmaceutical formulation of embodiment 135, wherein the artemisinin is artemether, artesunate and/or dihydroartemisinin.
175. The pharmaceutical formulation of embodiment 135, wherein the quinine and related agent is quinimax and/or quinidine.
176. The pharmaceutical formulation of embodiment 135, wherein the sulfonamide is sulfadoxine and/or sulfamethoxypyridazine.
177. The pharmaceutical formulation of embodiment 135, wherein the food additive and/or vitamin is tributerin, vitamin C, vitamin 812, vitamin D, resveratrol and/or coenzyme Q12.
178. The pharmaceutical formulation of embodiment 135, wherein the glucose intake inhibitor is a GLUT-1 receptor inhibitor.
179. The pharmaceutical formulation of embodiment 135, wherein the lipid intake inhibitor is an LDL receptor inhibitor, an SR-81 inhibitor, an SR-82 inhibitor and/or a SR-83/CD36 (thrombospondin) receptor inhibitor.
180. The pharmaceutical formulation of any of embodiments 136-179, wherein an individual is administered one or more of the cancer therapeutics.
181. The pharmaceutical composition of any of the proceeding embodiments, wherein a pharmaceutical composition includes a pharmaceutically acceptable solvent, a pharmaceutically acceptable stabilizing agent, a pharmaceutically acceptable carrier and/or a pharmaceutically acceptable component.
182. The pharmaceutical composition of any proceeding embodiment, wherein a cancer therapeutic is capable of reducing the number of cancer cells or tumor size in an individual suffering from a cancer by, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment.
183. The pharmaceutical composition of any proceeding embodiment, wherein a cancer therapeutic is capable of reducing the number of cancer cells or tumor size in an individual suffering from a cancer by, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to 70%, about 50% to 70% as compared to a patient not receiving the same treatment.
184. The pharmaceutical composition of any of the preceding embodiments, wherein a cancer therapeutic has a half-life of one hour.
185. The pharmaceutical composition of any of the preceding embodiments, wherein the dosing of a cancer therapeutic is daily.
186. The pharmaceutical composition of any of the preceding embodiments, wherein a cancer therapeutic has a half-life of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months and/or four months.
187. The pharmaceutical composition of any of the preceding embodiments, wherein a cancer therapeutic is administered to an individual for a period of time followed by a separate period of time.
188. The pharmaceutical composition of any of the preceding embodiments, wherein a cancer therapeutic is administered for a first period and a second period following the first period, with administration stopped during the second period, followed by a third period where administration of the cancer therapeutic is started and then a fourth period following the third period where administration is stopped.
189. The pharmaceutical composition of any of the preceding embodiments, wherein a cancer therapeutic is administered for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.
190. The pharmaceutical composition of any of the preceding embodiments, wherein a first cancer therapeutic s administered to an individual and at a later date, a second cancer therapeutic is administered to the same individual
191. The pharmaceutical composition of any of the preceding embodiments, wherein a first cancer therapeutic is administered to an individual at the same time as a second cancer therapeutic is administered to the individual.
192. The pharmaceutical composition of any of the preceding embodiments, wherein the pharmaceutical composition is a liquid, a sold and/or a semi-solid.
193. The pharmaceutical composition of embodiment 192, wherein, the pharmaceutical composition is provided to an individual in a capsule, tablet, pill, lozenge, powder and/or granule.
194. The pharmaceutical composition of embodiment 192, wherein the pharmaceutical composition is inhaled.
195. The pharmaceutical composition of embodiment 134, wherein the pharmaceutical composition is formulated in an oil-in-water emulsion.
196. The pharmaceutical composition of embodiment 195, wherein the oil is a vegetable oil, an animal fat and/or a mineral oil.
197. The pharmaceutical composition of any of embodiments 134-180, wherein the pharmaceutical composition is released in a controlled release profile over time.
198. The pharmaceutical composition of any of embodiments 134-180, wherein the pharmaceutical composition is provided in an extended release cancer therapeutic delivery form.
199. The pharmaceutical composition of any of embodiments 134-180, wherein the pharmaceutical composition is provided in a sustained release cancer therapeutic deliver form.
200. The pharmaceutical composition of embodiment 199, wherein the sustained release cancer therapeutic delivery platform releases a cancer therapeutic with substantially zero order release kinetics over a period of about 7 days after administration, about 15 days after administration, about 30 days after administration, about 45 days after administration, about 60 days after administration, about 75 days after administration and/or about 90 days after administration.

201. The pharmaceutical composition of embodiment 199, wherein the sustained release cancer therapeutic delivery platform releases a cancer therapeutic with substantially zero order release kinetics over a period of at least 7 days after administration, at least 15 days after administration, at least 30 days after administration, at least 45 days after administration, at least 60 days after administration, at least 75 days after administration, or at least 90 days after administration.
202. The pharmaceutical composition of embodiment 199, wherein the sustained release cancer therapeutic delivery platform releases a cancer therapeutic with substantially first order release kinetics over a period of about 7 days after administration, about 15 days after administration, about 30 days after administration, about 45 days after administration, about 60 days after administration, about 75 days after administration, or about 90 days after administration.
203. The pharmaceutical composition of embodiment 199, wherein the sustained release cancer therapeutic delivery platform releases a cancer therapeutic with substantially first order release kinetics over a period of at least 7 days after administration, at least 15 days after administration, at least 30 days after administration, at least 45 days after administration, at least 60 days after administration, at least 75 days after administration, or at least 90 days after administration.
204. The pharmaceutical composition of embodiment 199, wherein a cancer therapeutic delivery platform releases a cancer therapeutic with substantially zero order release kinetics over a period of about 1 day after administration, about 2 days after administration, about 3 days after administration, about 4 days after administration, about 5 days after administration, or about 6 days after administration.
205. The pharmaceutical composition of embodiment 199, wherein a cancer therapeutic delivery platform releases a cancer therapeutic with substantially zero order release kinetics over a period of, e.g., at most 1 day after administration, at most 2 days after administration, at most 3 days after administration, at most 4 days after administration, at most 5 days after administration, or at most 6 days after administration.
206. The pharmaceutical composition of embodiment 199, wherein a cancer therapeutic delivery platform releases a cancer therapeutic disclosed herein with substantially first order release kinetics over a period of about 1 day after administration, about 2 days after administration, about 3 days after administration, about 4 days after administration, about 5 days after administration, or about 6 days after administration.
207. The pharmaceutical composition of embodiment 199, wherein a cancer therapeutic delivery platform releases a cancer therapeutic disclosed herein with substantially first order release kinetics over a period of at most 1 day after administration, at most 2 days after administration, at most 3 days after administration, at most 4 days after administration, at most 5 days after administration, or at most 6 days after administration.
208. The pharmaceutical composition of any proceeding embodiment, wherein the concentration of a cancer therapeutic is at least 0.00001 mg/ml, at least 0.0001 mg/ml, at least 0.001 mg/ml, at least 0.01 mg/ml, at least 0.1 mg/ml, at least 1 mg/ml, at least 10 mg/ml, at least 25 mg/ml, at least 50 mg/ml, at least 100 mg/ml, at least 200 mg/ml, at least 500 mg/ml, at least 700 mg/ml, at least 1,000 mg/ml, or at least 1,200 mg/ml.
209. The pharmaceutical composition of any proceeding embodiment, wherein the concentration of a cancer therapeutic is at most 1,000 mg/ml, at most 1,100 mg/ml, at most 1,200 mg/ml, at most 1,300 mg/ml, at most 1,400 mg/ml, at most 1,500 mg/ml, at most 2,000 mg/ml, at most 2,000 mg/ml, or at most 3,000 mg/ml.
210. The pharmaceutical composition of any proceeding embodiment, wherein the concentration of a cancer therapeutic is about 0.00001 mg/ml to about 3,000 mg/ml, about 0.0001 mg/ml to about 3,000 mg/ml, about 0.01 mg/ml to about 3,000 mg/ml, about 0.1 mg/ml to about 3,000 mg/ml, about 1 mg/ml to about 3,000 mg/ml, about 250 mg/ml to about 3,000 mg/ml, about 500 mg/ml to about 3,000 mg/ml, about 750 mg/ml to about 3,000 mg/ml, about 1,000 mg/ml to about 3,000 mg/ml, about 100 mg/ml to about 2,000 mg/ml, about 250 mg/ml to about 2,000 mg/ml, about 500 mg/ml to about 2,000 mg/ml, about 750 mg/ml to about 2,000 mg/ml, about 1,000 mg/ml to about 2,000 mg/ml, about 100 mg/ml to about 1,500 mg/ml, about 250 mg/ml to about 1,500 mg/ml, about 500 mg/ml to about 1,500 mg/ml, about 750 mg/ml to about 1,500 mg/ml, about 1,000 mg/ml to about 1,500 mg/ml, about 100 mg/ml to about 1,200 mg/ml, about 250 mg/ml to about 1,200 mg/ml, about 500 mg/ml to about 1,200 mg/ml, about 750 mg/ml to about 1,200 mg/ml, about 1,000 mg/ml to about 1,200 mg/ml, about 100 mg/ml to about 1,000 mg/ml, about 250 mg/ml to about 1,000 mg/ml, about 500 mg/ml to about 1,000 mg/ml, about 750 mg/ml to about 1,000 mg/ml, about 100 mg/ml to about 750 mg/ml, about 250 mg/ml to about 750 mg/ml, about 500 mg/ml to about 750 mg/ml, about 100 mg/ml to about 500 mg/ml, about 250 mg/ml to about 500 mg/ml, about 0.00001 mg/ml to about 0.0001 mg/ml, about 0.00001 mg/ml to about 0.001 mg/ml, about 0.00001 mg/ml to about 0.01 mg/ml, about 0.00001 mg/ml to about 0.1 mg/ml, about 0.00001 mg/ml to about 1 mg/ml, about 0.001 mg/ml to about 0.01 mg/ml, about 0.001 mg/ml to about 0.1 mg/ml, about 0.001 mg/ml to about 1 mg/ml, about 0.001 mg/ml to about 10 mg/ml, or about 0.001 mg/ml to about 100 mg/ml.
211. The pharmaceutical composition of any of embodiments 134-180, wherein a cancer therapeutic is formulated in one fat.
212. The pharmaceutical composition of any of embodiments 134-180, wherein a cancer therapeutic is formulated in two fats.
213. The pharmaceutical composition of any of embodiments 134-180, wherein a cancer therapeutic is formulated in three fats, four fats, five fats, six fats or seven or more fats.
214. The pharmaceutical composition of any of embodiments 134-180, wherein a cancer therapeutic is formulated in a fat that is a liquid.
215. The pharmaceutical composition of any of embodiments 134-180, wherein a cancer therapeutic is formulated in at fat that is a solid.
216. The pharmaceutical composition of any of embodiments 134-180, wherein a cancer therapeutic is formulated in two or more fats that are liquids.
217. The pharmaceutical composition of any of embodiments 134-180, wherein a cancer therapeutic is formulated in two or more fats that are solids.
218. The pharmaceutical composition of any of embodiments 134-180, wherein a cancer therapeutic is formulated in two or more fats, wherein at least one fat is a solid and at least one fat is a liquid.

219. The pharmaceutical composition of any proceeding embodiment, wherein the concentration of a cancer therapeutic is at least 0.00001 mg/ml, at least 0.0001 mg/ml, at least 0.001 mg/ml, at least 0.01 mg/ml, at least 0.1 mg/ml, at least 1 mg/ml, at least 10 mg/ml, at least 25 mg/ml, at least 50 mg/ml, at least 100 mg/ml, at least 200 mg/ml, at least 500 mg/ml, at least 700 mg/ml, at least 1,000 mg/ml, or at least 1,200 mg/ml.

220. The pharmaceutical composition of any proceeding embodiment, wherein the concentration of a cancer therapeutic is at most 1,000 mg/ml, at most 1,100 mg/ml, at most 1,200 mg/ml, at most 1,300 mg/ml, at most 1,400 mg/ml, at most 1,500 mg/ml, at most 2,000 mg/ml, at most 2,000 mg/ml, or at most 3,000 mg/ml.

221. The pharmaceutical composition of any proceeding embodiment, wherein the concentration of a cancer therapeutic is about 0.00001 mg/ml to about 3,000 mg/ml, about 0.0001 mg/ml to about 3,000 mg/ml, about 0.01 mg/ml to about 3,000 mg/ml, about 0.1 mg/ml to about 3,000 mg/ml, about 1 mg/ml to about 3,000 mg/ml, about 250 mg/ml to about 3,000 mg/ml, about 500 mg/ml to about 3,000 mg/ml, about 750 mg/ml to about 3,000 mg/ml, about 1,000 mg/ml to about 3,000 mg/ml, about 100 mg/ml to about 2,000 mg/ml, about 250 mg/ml to about 2,000 mg/ml, about 500 mg/ml to about 2,000 mg/ml, about 750 mg/ml to about 2,000 mg/ml, about 1,000 mg/ml to about 2,000 mg/ml, about 100 mg/ml to about 1,500 mg/ml, about 250 mg/ml to about 1,500 mg/ml, about 500 mg/ml to about 1,500 mg/ml, about 750 mg/ml to about 1,500 mg/ml, about 1,000 mg/ml to about 1,500 mg/ml, about 100 mg/ml to about 1,200 mg/ml, about 250 mg/ml to about 1,200 mg/ml, about 500 mg/ml to about 1,200 mg/ml, about 750 mg/ml to about 1,200 mg/ml, about 1,000 mg/ml to about 1,200 mg/ml, about 100 mg/ml to about 1,000 mg/ml, about 250 mg/ml to about 1,000 mg/ml, about 500 mg/ml to about 1,000 mg/ml, about 750 mg/ml to about 1,000 mg/ml, about 100 mg/ml to about 750 mg/ml, about 250 mg/ml to about 750 mg/ml, about 500 mg/ml to about 750 mg/ml, about 100 mg/ml to about 500 mg/ml, about 250 mg/ml to about 500 mg/ml, about 0.00001 mg/ml to about 0.0001 mg/ml, about 0.00001 mg/ml to about 0.001 mg/ml, about 0.00001 mg/ml to about 0.01 mg/ml, about 0.00001 mg/ml to about 0.1 mg/ml, about 0.00001 mg/ml to about 1 mg/ml, about 0.001 mg/ml to about 0.01 mg/ml, about 0.001 mg/ml to about 0.1 mg/ml, about 0.001 mg/ml to about 1 mg/ml, about 0.001 mg/ml to about 10 mg/ml, or about 0.001 mg/ml to about 100 mg/ml.

222. The pharmaceutical composition of any of embodiments 134-180, wherein the composition is a liquid, semi-solid or a solid formulation 223. The pharmaceutical composition of any of embodiments 134-180, wherein the therapeutic results in a cancer cell not being able to uptake sufficient quantities of glucose or other energy source resulting in the cell entering apoptosis and eventually dying.

224. The pharmaceutical composition of any of embodiments 134-180, wherein the cancer therapeutic results in a cell not being able to uptake sufficient quantities of a lipid, other fat and/or cholesterol, preventing the cancer cell from dividing and forming a progeny cancer cell.

EXAMPLES

Example 1

A patient comprising a 49 year old woman was diagnosed by her physician with advanced metastatic breast cancer. The metastatic breast cancer consisted of tumors, including several found in both lungs. The physician prescribed a standard set of cancer therapeutics in an attempt to reduce or maintain the tumors. The patient did not tolerate the cancer therapeutics that were administered that consisted of Taxol and capecitabine. The physician placed the patient on a paliative care regime and provided the patient with several doses of the aromatase inhibitor, letrazole. Following this treatment, the patient was administered a CAT scan, which revealed that her tumors were progressing, including one tumor in a lung that had grown by 50% in three months. The patient was next administered a treatment consisting of artemether at a dose of 40 mg OD, presented in a lipid filled capsule comprising tributyrin and G43. A CAT scan given to the patient several months after administration of artemether found that all tumor growth had stopped and the breast cancer did not progress in the patient during the period of artemether administration.

Example 2

A patient comprising a 50 year old woman was diagnosed by her physician with extensive metastaic breast cancer. The patient presented with tumors in brain liver and lungs. The patient also presented with symptoms that included shortness of breath and a persistent cough. The patient informed the physician that she would not take part in a standard chemotherapy treatment protocol. The physician informed the patient that she would only live for about three months survival. The patient was instead administered artemether at a dose of 40 mg OD, presented as a lipid filled capsule comprising tributyrin and G43. As a result of the treatment, the symptoms the patient suffered from, including, shortness of breath and a persistent cough diminished over the weeks following treatment with arthemether. The patient continues to survive, six months following the initial diagnosis.

Example 3

A patient comprising a 53 year old male was diagnosed with prostate cancer by his physician with several tumors in the prostate. The physician prescribed a hormone therapeutic formulated in a lipid formulation comprising tributyrin and G43. The patent was administered the therapeutic over a six month period, with a reduction in the size of the tumors. After several more months of treatment, the cancer was determined to be in remission Example 4

A patient comprising a 41 year old male was diagnosed with pancreatic cancer by his physician which had metastasized into the brain and liver. The physician prescribed chemotherapy, comprising a mixture of cancer therapeutics, including Gemzar, Tarceva and Avastin formulated in a lipid formulation given as a liquid intravenously. The progression of the cancer slowed over time and several of the tumors were reduced in size. The patient who was given a three month life span lived for an additional four years following initiation of treatment.

Example 5

A patient comprising a 37 year old female was diagnosed with acute myeloid leukemia by her physician which had metastasized. The physician prescribed chemotherapy, comprising a 40 mg OD of arthemether formulated in a lipid formulation comprising tributyrin and G43. The progression of the cancer slowed over time. The patient continues to live and their health is improving.

Example 6

A patient comprising a 71 year old woman was diagnosed by her physician with advanced metastatic breast cancer. The metastatic breast cancer consisted of tumors, including several found in both lungs. The physician prescribed a standard set of cancer therapeutics in an attempt to reduce or maintain the tumors. The patient did not tolerate the cancer therapeutics that were administered that consisted of Taxol and capecitabine. The physician placed the patient on a paliative care regime and provided the patient with several doses of the aromatase inhibitor, letrazole. Following this treatment, the patient was administered a CAT scan, which revealed that her tumors were progressing, including one tumor in a lung that had grown by 50% in three months. The patient was next administered a treatment consisting of artemether at a dose of 40 mg OD, presented in a lipid filled capsule comprising tributyrin and G43. A CAT scan given to the patient several months after administration of artemether found that all tumor growth had stopped and the breast cancer did not progress in the patient during the period of artemether administration.

Example 7

A patient comprising a 70 year old female was diagnosed with primary peritoneal cancer by her physician with several tumors in her peritoneum that included small tumors attached to her large intestine. The female was on chemotherapy and did not see either a reduction in her Cancer Antigen 125 ("CA") test or in the size or number of tumors. The female began taking a combination of Metformin, Lipitor and Mebendazole purchased from a pharmacy. The patient was administered the therapeutic combination over a six month period, and during that time period, experienced a reduction in the size of the tumors. After several more months of treatment, the cancer was determined to be in remission.

Example 8

A patient comprising a 45 year old male was diagnosed with pancreatic cancer by his physician, which had metastasized into his brain and liver. The physician prescribed chemotherapy, comprising a mixture of cancer therapeutics, including Gemzar, Tarceva and Avastin formulated in a lipid formulation given as a liquid intravenously. The progression of the cancer slowed over time and several of the tumors were reduced in size but the patient became progressively sicker. The chemotherapy was supplemented with Arthemether, Simvastin, Metformin, Mebendazole and Tributyrin. Following initiation of the treatment with these four drugs, the patient, began to become physically stronger.

Example 9

To assess the effect of Artesunate in combination with several other therapeutics, MCF-7 cells were treated with different concentrations of these therapeutic compounds either once or through repeated dosing. The percentage of survival was calculated based on the LDH contents of cells.

Protocol followed:

Day −1: Seeding Cells in Wells of Plate 1. 100 ul of cells suspension ($3\times10^4$ cells/ml) were added to each well (3000 cells/well), with a total of 5 plates were seeded.
2. Plates were left at room temperature in the hood for 1 hour before being placed in the incubator.
3. Some wells were left with no cells as background control.

Day 0: Treatment 50 ul of each therapeutic treatment was added to wells already containing 100 ul of the cell suspension at the doses indicated in the template below for Sodium Butyrate, through similar concentrations were used for Resveratrol, Daidzein and Equol:

|  |  | Artesunate | | | | | | | | | | | |
|---|---|---|---|---|---|---|---|---|---|---|---|---|---|
|  |  | 1000 ng/ml | 500 ng/ml | 250 ng/ml | 125 ng/ml | 62.5 ng/ml | 0 | 1000 ng/ml | 500 ng/ml | 250 ng/ml | 125 ng/ml | 62.5 ng/ml | 0 |
| Sodium Butyrate | 4 mM | | | | | | | | | | | | |
|  | 2 mM | | | | | | | | | | | | |
|  | 1 mM | | | | | | | | | | | | |
|  | 0.5 mM | | | | | | | | | | | | |
|  | 0.25 mM | | | | | | | | | | | | |
|  | 0.125 mM | | | | | | | | | | | | |
|  | 0 | | Cells in CM | | Cells in Vehic. Cells in Vehicle | | | Cells in MMC | | | Cells in Vehic. Vehicle | | |

Preparation of Artesunate for Therapeutic Treatment
  Using an analytical balance, Artesunate was weighed straight into a 1.5 ml screw cap tube.
  The appropriate volume of 100% Ethanol was added to Artesunate to obtain a concentration of 10 mg/ml.
  This was further diluted in 100% Ethanol to 1 mg/ml (1:10).
  4 ug/ml was obtained by diluting 1 mg/ml (1:250) in complete medium. Further double decreasing dilutions were carried out in complete medium containing 0.4% Ethanol.

Preparation of Sodium Butyrate Dilutions for Therapeutic Treatment
  Using an analytical balance, Sodium Butyrate was weighed straight into a 15 ml falcon tube.
  The appropriate volume of complete medium was added to Sodium Butyrate to obtain a concentration of 100 mM.
  This was further diluted in complete medium to 16 mM (1:6.25). Further double decreasing dilutions were carried out in complete medium.

Preparation of Resveratrol Dilutions for Therapeutic Treatment
- Using an analytical balance, Sodium Butyrate was weighed straight into a 15 ml falcon tube.
- The appropriate volume of complete medium was added to Sodium Butyrate to obtain a concentration of 100 mM.
- This was further diluted in complete medium to 16 mM (1:6.25). Further double decreasing dilutions were carried out in complete medium.

Preparation of Daidzein Dilutions for Therapeutic Treatment
- Using an analytical balance, Sodium Butyrate was weighed straight into a 15 ml falcon tube.
- The appropriate volume of complete medium was added to Sodium Butyrate to obtain a concentration of 100 mM.
- This was further diluted in complete medium to 16 mM (1:6.25). Further double decreasing dilutions were carried out in complete medium.

Preparation of Equol Dilutions for Therapeutic Treatment
- Using an analytical balance, Sodium Butyrate was weighed straight into a 15 ml falcon tube.
- The appropriate volume of complete medium was added to Sodium Butyrate to obtain a concentration of 100 mM.
- This was further diluted in complete medium to 16 mM (1:6.25). Further double decreasing dilutions were carried out in complete medium.

Preparation of Controls
- 2 mg of MMC were resuspended in 4 ml of sterile water to obtain a stock at 0.5 mg/ml. A second dilution of MMC was carried out by diluting 0.5 mg/ml in complete medium to 0.1 mg/ml (1:5).
- Complete medium was prepared at 0.4% Ethanol 4. Once the treatments were ready, 50 ul/well of Artesunate was added to the plates. Next, 50 ul of Sodium Butyrate, Resveratrol, Daidzein or Equol were added to the wells already containing 100 ul of cells suspension plus 50 ul of Artesunate.

5. 50 ul of complete medium at 0.4% Ethanol and 50 ul of just complete medium were added to the corresponding control wells already containing either 100 ul of cells (positive control) or just 100 ul of complete medium (background control)

6. 100 ul of MMC at 100 ug/ml was added to the corresponding wells already containing 100 ul of cells in complete medium as a negative control and finally, plates were placed in the incubator.

Day 1: Re-Dosing and LDH-24 h 7. 24 h after treatment of cells with a the aforementioned therapeutics, two of the plates were re-dosed with the same treatments described above, while another two plates were left incubating as they were and the remaining plate was used to measure the percent of survival by LDH through the following method:
- Media was removed from the wells by using a multichannel pipette.
- Wells were washed with 200 ul/well of PBS previously warmed at 37° C.
- 100 ul of Titron 1× in PBS previously warmed at 37° C. were added to the wells. Subsequently, the plate was placed at 37° C. in the dark for 45 min.
- 50 ul from each well was transferred to a non sterile 96-well plate.
- 50 ul of LDH substrate were added to each well of the non sterile plate already containing 50 ul/well of lysed cells and the plates were then incubating at room temperature in the dark for 30 min.
- 50 ul of Stop solution was added to each well and then the plate was read at 492 nm.

Day 2: Re-Dosing, LDH-48 h and LDH-Re-Dosing at 24 h

8. After 48 h of cells treatment, one of the 2 plates that had been re-dosed after 24 h was re-dosed again (treatments were prepared as described above for re-dosing). One of the 2 plates that had been treated just once will remain as it was in the incubator. The remaining 2 plates were used to measure the % of survival by LDH after 48 h of single treatment and after re-dosing at 24 h (LDH assay was performed as described above).

Day 3: LDH-72 h and LDH-Re-Dosing at 24 h and at 48 h

After 72 h of cells treatment, there were just 2 plates left in the incubator. They were used to measure the % of survival by LDH after 72 h of single treatment and after re-dosing at 24 h and 48 h (LDH assay was performed as described above).

Figure 2:
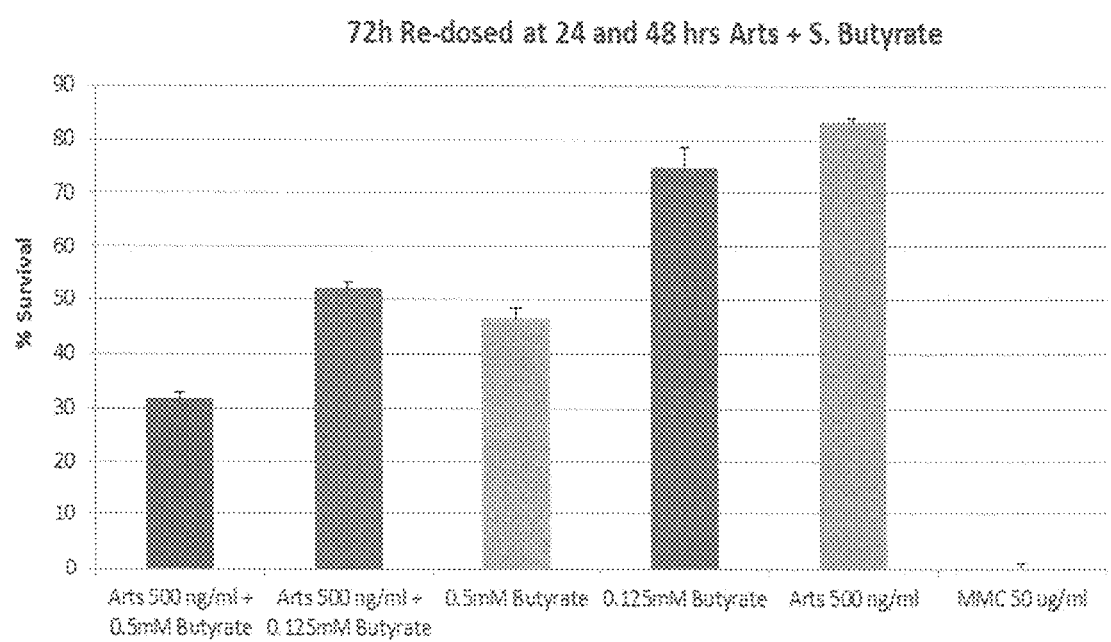
FIG. 2 shows the results for samples assessed 72 hours after wells containing MCF-7 cells (or no cells in a control) were administered multiple doses (at 24 and 48 hours) of Artesunate and/or Sodium Butyrate.

In FIGS. 1 and 2, the results are provided for samples assessed 72 hours after wells containing MCF-7 cells (or no cells in a control) were administered either a single or a multiple dose of Artesunate and/or Sodium Butyrate. As seen in both figures, Artesunate and Sodium Butyrate individually decreased the survival of MCF-7 cells dosed once or multiple times with one or the other therapeutic treatment. When Artesunate and Sodium Butyrate were administered in combination to the MCF-7 cells, the percent of cells that survived was less than when Artesunate and Sodium Butyrate were administered individually. (see FIGS. 1 and 2). Further, the percent of cells decreased even more as the dose of Sodium Butyrate administered with Artesunate was increased. (see FIGS. 1 and 2).

Figure 3:
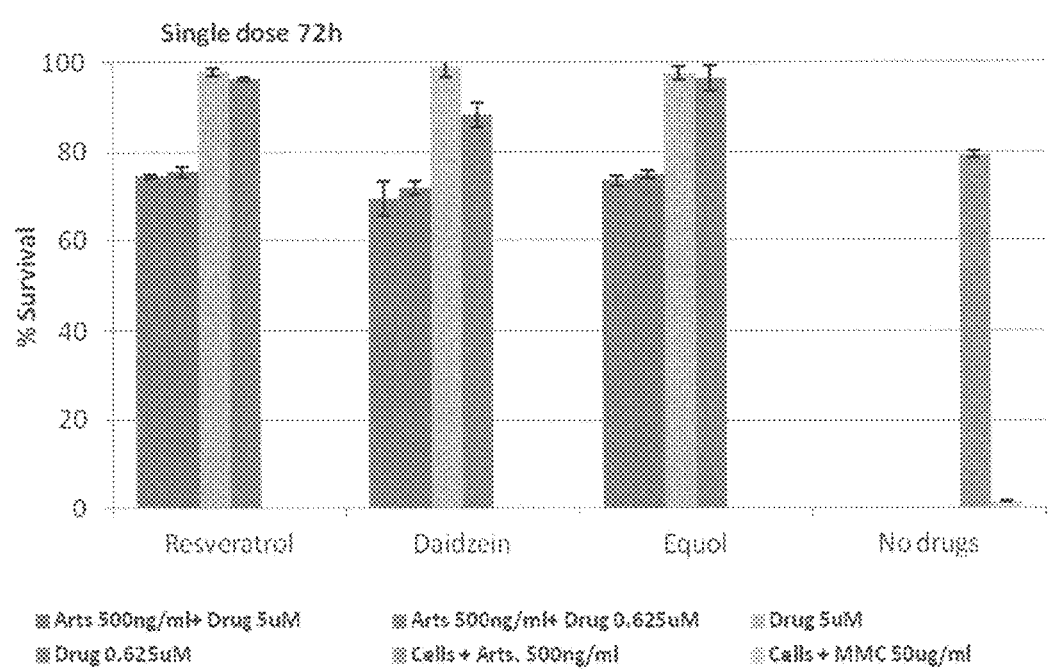
FIG. 3 shows the results for samples assessed 72 hours after wells containing MCF-7 cells (or no cells in a control) were administered a single dose of Artesunate and/or Resveratrol, Daidzein or Equol or no drug (far right panel).
Figure 4:
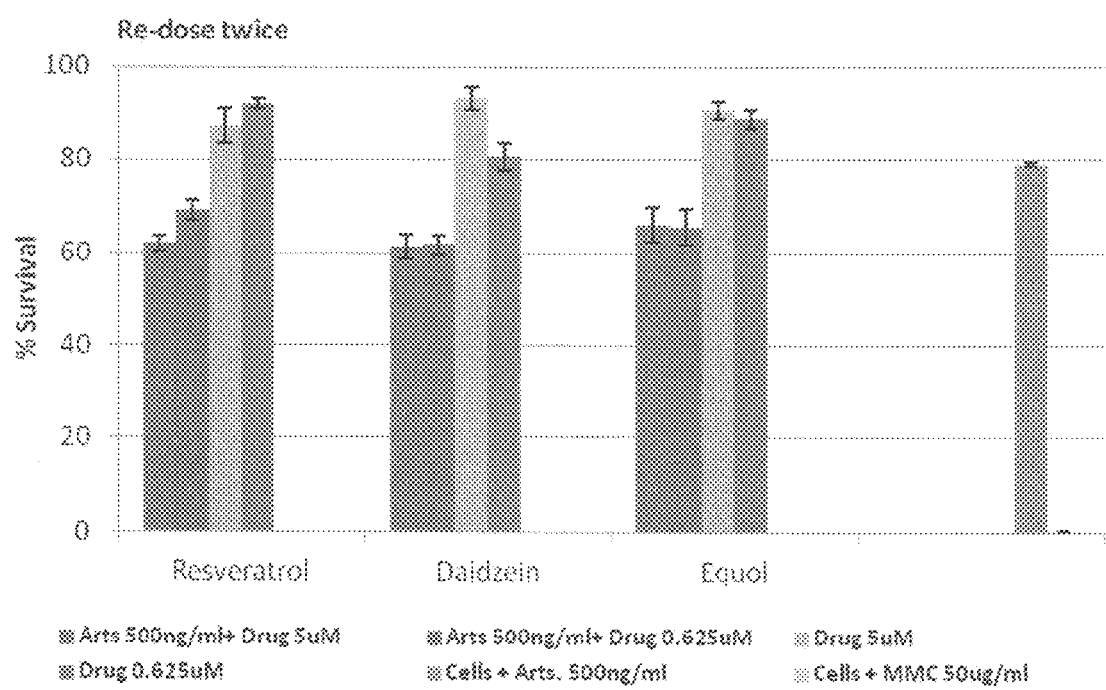
FIG. 4 shows the results for samples assessed 72 hours after wells containing MCF-7 cells (or no cells in a control) were administered multiple doses of Artesunate and/or Resveratrol, Daidzein or Equol or no drug (far right panel).

In FIGS. 3 and 4, the results are provided for samples assessed 72 hours after wells containing MCF-7 cells (or no cells in a control) were administered either a single or a multiple dose of Artesunate and/or Resveratrol, Daidzein or Equol. As seen in both figures, Artesunate decreased the survival of MCF-7 cells dosed once or multiple times with the therapeutic treatment, while Resveratrol, Daidzein and Equol when dosed singly had only minimal effect on the percent of survival of MCF-7 cells, with the percent of survival decreasing marginally when these therapeutic treatments were administered more than once to the cultured cells. When Artesunate and Resveratrol, Daidzein or Equol were administered in combination to the MCF-7 cells, the percent of cells that survived was less than when Artesunate Resveratrol, Daidzein or Equol were administered individually. (see FIGS. 1 and 2). Further, the percent of cells decreased even more as the dose of Resveratrol, Daidzein or Equol administered with Artesunate was increased and as the dose of Resveratrol, Daidzein or Equol administered with Artesunate was increased. (see FIGS. 1 and 2).

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of treating a cancer, the method comprising administering one or more cancer therapeutics to an individual with the cancer, wherein the one or more cancer therapeutics include
   a) a first cancer therapeutic that is a therapeutically effective does of an anti-diabetic drug;
   b) a second cancer therapeutic that is a therapeutically effective dose of a statin; and
   c) a third cancer therapeutic that is a therapeutically effective dose of a glycolysis inhibitor.

2. The method according to claim 1, wherein the anti-diabetic drug is a biguanide, a thiazolidinedione, a secretagogue, an alpha-glucosidase inhibitor and/or a peptide analog, a cinnamon, a thiamine or any combination thereof.

3. The method according to claim 2, wherein the biguanide is a metformin, a phenformin and/or a buformin.

4. The method according to claim 1, wherein the statin is an atorvastatin, a fluvastin, a lovastatin, a pitavastatin, a pravastatin, a rosuvastatin, a simvastatin or any combination thereof.

5. The method according to claim 1, wherein the glycolysis inhibitor includes a hexokinase inhibitor, a phosphoglucose isomerase inhibitor, a fructosebisphosphate inhibitor, a triosephosphate isomerase inhibitor, a glyceraldehyde phosphate dehydrogenase inhibitor, a phosphoglycerate kinase inhibitor, a phosphoglycerate mutase inhibitor, an enolase inhibitor and/or a pyruvate kinase inhibitor, an anti-helminthic agent, an anti-malarial agent, an antibiotic or any combination thereof.

6. The method according to claim 5, wherein the anti-helminthic agent includes an abamectin, an aminoacetonitriles, a benzimidazole, a diethylcarbamazine, an ivermectin, a levamisole, niclosamide, an octadepsipeptides, a phosphoric acid, a praziquantel, a spiroindoles, a suramin, a pyrantel pamoate or any combination thereof.

7. The method according to claim 6, wherein the benzimidazole is an albendazole, a fenbendazole, a flubendazole, a thiabendazole or a triclabendazole.

8. The method according to claim 7, wherein the flubendazole is a mebendazole.

9. The method according to claim 5, wherein the antimalarial agent includes an amodiaquine, an artemisinin, an atovaquone, a chloroquine, a clindamycin, a doxycycline, a halofantrine, a mefloquine, a primaquine, a proguanil, a pyrimethamine, a quinine, a rufigallol, a sulphonamide or any combination thereof.

10. The method according to claim 9, wherein the artemisinin is an arteether, an artelinate, an artelinic acid, an artemether, an artemotil, an artemisinin, an artenimol, an arterolane, an artesunate, a dihydroartemisinin and/or a dihydroartemisinin methyl ether.

11. The method according to claim 5, wherein the therapeutically effective dose of the anti-diabetic drug is in an amount of 1 mg/kg/day to about 40 mg/kg/day, the therapeutically effective dose of the statin is in an amount of 0.01 mg/kg/day to about 10 mg/kg/day, the therapeutically effective dose of the anti-helminthic agent is in an amount of 0.01 mg/kg/day to about 10 mg/kg/day and the therapeutically effective dose of the anti-malarial agent is in an amount of 0.01 mg/kg/day to about 10 mg/kg/day.

12. The method according to claim 5, wherein the one or more cancer therapeutics comprise an anti-diabetic drug, a statin, an anti-helminthic agent and an anti-malaria agent.

13. The method according to claim 1, further comprising administering a fourth cancer therapeutic that is a therapeutically effective dose of a therapeutic that is a glucose intake inhibitor.

14. The method according to claim 13, wherein the glucose intake inhibitor includes a GLUT-1 receptor inhibitor.

15. The method according to claim 14, wherein the GLUT-1 receptor inhibitor is Vitamin C.

16. The method according to claim 1, further comprising administering a fourth cancer therapeutic that is a therapeutically effective dose of a therapeutic that is a lipid intake inhibitor.

17. The method according to claim 16, wherein the lipid intake inhibitor includes an LDL receptor inhibitor, an SR-81 inhibitor, an SR-82 inhibitor, a SR-83/CD36receptor inhibitor or any combination thereof.

18. The method according to claim 17, wherein the LDL receptor inhibitor is Vitamin D.

19. The method according to claim 1, wherein the one or more cancer therapeutics comprise metformin, atorvastatin, mebendazole and doxycycline.

20. The method according to claim 1, done in conjunction with a chemotherapy, a radiation therapy, a surgery, an immunotherapy, or a freezing a tumor.

21. The method according to claim 1, wherein the cancer is a brain cancer, a bladder cancer, a breast cancer, a colon cancer, a rectal cancer, an endometrial cancer, a kidney cancer, a renal cancer, a leukemia, a lung cancer, a melanoma, a non-Hodgkins lymphoma, a pancreatic cancer, a prostate cancer, a stomach cancer or a thyroid cancer.

22. The method according to claim 1, wherein the one or more cancer therapeutics comprise an anti-diabetic drug, a statin, an anti-helminthic agent and an anti-malaria agent.

23. The method according to claim 1, wherein the one or more cancer therapeutics comprise a biguanide, a statin, a benzimidazole and a doxycycline.

* * * * *